United States Patent
Miyake et al.

(10) Patent No.: US 12,275,710 B2
(45) Date of Patent: Apr. 15, 2025

(54) COMPOUND, CURING AGENT COMPOSITION, RESIN COMPOSITION, COATING COMPOSITION AND RESIN CURED PRODUCT

(71) Applicant: ASAHI KASEI KABUSHIKI KAISHA, Tokyo (JP)

(72) Inventors: Nobuhisa Miyake, Tokyo (JP); Masakazu Yamauchi, Tokyo (JP); Hiroshi Inada, Tokyo (JP); Yusuke Ebe, Tokyo (JP); Masaaki Shinohata, Tokyo (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 1025 days.

(21) Appl. No.: 17/053,840

(22) PCT Filed: May 15, 2019

(86) PCT No.: PCT/JP2019/019293
§ 371 (c)(1),
(2) Date: Nov. 9, 2020

(87) PCT Pub. No.: WO2019/221173
PCT Pub. Date: Nov. 21, 2019

(65) Prior Publication Data
US 2021/0238141 A1    Aug. 5, 2021

(30) Foreign Application Priority Data

| May 15, 2018 | (JP) | 2018-094174 |
| Jan. 29, 2019 | (JP) | 2019-013633 |
| Jan. 29, 2019 | (JP) | 2019-013634 |
| Jan. 29, 2019 | (JP) | 2019-013635 |
| Jan. 29, 2019 | (JP) | 2019-013636 |

(51) Int. Cl.
| *C08G 18/09* | (2006.01) |
| *C07D 229/00* | (2006.01) |
| *C08G 18/71* | (2006.01) |
| *C08G 18/79* | (2006.01) |
| *C08G 18/80* | (2006.01) |
| *C08L 75/04* | (2006.01) |
| *C09D 175/04* | (2006.01) |

(52) U.S. Cl.
CPC ......... *C07D 229/00* (2013.01); *C08G 18/095* (2013.01); *C08G 18/71* (2013.01); *C08G 18/711* (2013.01); *C08G 18/797* (2013.01); *C08G 18/8064* (2013.01); *C08L 75/04* (2013.01); *C09D 175/04* (2013.01)

(58) Field of Classification Search
CPC .. C08G 18/797; C08G 18/8064; C08G 18/71; C08G 18/711; C08G 18/095
See application file for complete search history.

(56) References Cited

U.S. PATENT DOCUMENTS

| 5,008,363 | A | 4/1991 | Mallon et al. |
| 5,393,839 | A | 2/1995 | Iwamoto |
| 6,121,406 | A | 9/2000 | Imashiro et al. |
| 6,124,398 | A | 9/2000 | Imashiro et al. |
| 2008/0200619 | A1 | 8/2008 | Bosman |
| 2011/0021679 | A1 | 1/2011 | Takahashi et al. |
| 2013/0143458 | A1 | 6/2013 | Avtomonov et al. |
| 2013/0144006 | A1* | 6/2013 | Derksen ............... C08G 18/797 528/65 |
| 2016/0264709 | A1 | 9/2016 | Smith |
| 2017/0253688 | A1* | 9/2017 | Yamauchi .......... C08G 18/7887 |
| 2018/0148533 | A1 | 5/2018 | Yamashita et al. |

FOREIGN PATENT DOCUMENTS

| CN | 101213236 A | 7/2008 |
| CN | 102985456 A | 3/2013 |
| CN | 103119084 A | 5/2013 |
| CN | 107099019 A | 8/2017 |
| EP | 0515161 A1 | 11/1992 |
| GB | 1356851 A | 6/1974 |
| GB | 1523962 A | 9/1978 |
| JP | 51-101918 A | 9/1976 |
| JP | 04-222814 A | 8/1992 |
| JP | 04-342713 A | 11/1992 |
| JP | 06-206978 A | 7/1994 |
| JP | 10-316930 A | 12/1998 |
| JP | 2000-007958 A | 1/2000 |
| JP | 2002-371246 A | 12/2002 |
| JP | 2008-156517 A | 7/2008 |
| JP | 4309976 B2 | 8/2009 |
| JP | 2009-235278 A | 10/2009 |
| JP | 6170272 B1 | 7/2017 |
| JP | 2018-062633 A | 4/2018 |
| WO | 2008/009669 A1 | 1/2008 |
| WO | 2011/120928 A2 | 10/2011 |
| WO | 2012/015295 A1 | 2/2012 |

OTHER PUBLICATIONS

Chemical Abstract Registry No. 538-75-0, indexed in the Registry file on STN CAS Online Nov. 16, 1984. (Year: 1984).*
Third Party Submission (with partial translation) issued in corresponding Japanese Patent Application No. JP2020-519889, dated Dec. 1, 2020.

(Continued)

*Primary Examiner* — Michael L Leonard
(74) *Attorney, Agent, or Firm* — Morgan, Lewis & Bockius LLP

(57) ABSTRACT

A compound having an uretonimine group contains, as a structural unit, a carbodiimide compound derived from at least one of an aliphatic diisocyanate and an aromatic diisocyanate, and also contains an isocyanate compound as a structural unit, wherein the residue obtained by removing an isocyanate group from the isocyanate compound and the residue obtained by removing a carbodiimide group from the carbodiimide compound are different.

18 Claims, No Drawings

(56) References Cited

OTHER PUBLICATIONS

Written Opinion issued in corresponding International Patent Application No. PCT/JP2019/019293, dated Aug. 6, 2019.
Partial Supplementary European Search Report issued in corresponding European Patent Application No. 19803911.7, dated Sep. 22, 2021.
International Search Report issued in corresponding International Patent Application No. PCT/JP2019/019293, dated Aug. 6, 2019.

* cited by examiner

ND, CURING AGENT
COMPOSITION, RESIN COMPOSITION,
COATING COMPOSITION AND RESIN
CURED PRODUCT

TECHNICAL FIELD

The present invention relates to a novel compound having an uretonimine group, a carbodiimide compound and a method for producing the same, and a curing agent composition, a resin composition, a coating composition and a resin cured product containing these compounds.

Priority is claimed on Japanese Patent Application No. 2018-094174, filed May 15, 2018, Japanese Patent Application No. 2019-013633, Japanese Patent Application No. 2019-013634, Japanese Patent Application No. 2019-013635 and Japanese Patent Application No. 2019-013636, all filed Jan. 29, 2019, the contents of which are incorporated herein by reference.

BACKGROUND ART

In the production of automobiles, it is said that the coating processes account for about ⅓ of total energy consumption, and therefore from the viewpoints of environmental impact and reducing production costs, measures such as lowering the temperature during coating film baking and reducing the number of coating steps are being developed. In particular, carboxylic acids (or carboxyl groups) contained in the main agent tend to lower the water resistance of the coating film, and it is therefore desirable that these carboxylic acids are consumed during the baking of the coating film. Furthermore, as the temperature during coating film baking is lowered, it is necessary that the carboxylic acid consumption reaction occurs in low-temperature environments of 80° C. or the like. On the other hand, favorable storage stability of the coating material composition in temperature environments near 40° C. is also required. Carbodiimide compound are attracting much attention as potential compounds that satisfy these conditions.

A carbodiimide group can be produced by inducing a decarboxylation condensation reaction of two isocyanate groups in the presence of a catalyst. Patent Document 1 discloses a carbodiimide-based crosslinking agent in which the terminal isocyanate groups are terminated with hydrophilic groups containing a polyethylene oxide repeating unit. This carbodiimide-based crosslinking agent is described as having excellent water solubility or water dispersibility. Further, Patent Document 2 discloses a carbodiimide compound in which the terminal isocyanate groups are terminated with hydrophilic groups containing a polyalkylene oxide repeating unit. This carbodiimide compound is described as being able to improve the water resistance, solvent resistance and adhesion when converted to a coating film, while exhibiting similar pot life to conventional compositions when used in a coating material composition.

On the other hand, an uretonimine group is a linkage formed by adding one more isocyanate group to a carbodiimide group formed by bonding together two isocyanate groups. Uretonimine groups are known to dissociate at low temperature to regenerate an isocyanate group, and electrodeposition coating materials, resin compositions for coating materials and water-dispersed compositions and the like which use blocked isocyanate compounds or uretonimine group-containing compounds that utilize this property have been proposed (for example, see Patent Documents 3 and 4).

PRIOR ART LITERATURE

Patent Documents

Patent Document 1: Japanese Unexamined Patent Application, First Publication No. Hei 10-316930
Patent Document 2: Japanese Unexamined Patent Application, First Publication No. 2009-235278
Patent Document 3: Japanese Patent (Granted) Publication No. 4309976
Patent Document 4: Japanese Patent (Granted) Publication No. 6170272

SUMMARY OF INVENTION

Problems to be Solved by the Invention

However, conventionally proposed carbodiimide compounds having introduced hydrophilic groups at the terminals, such as the compounds disclosed in Patent Documents 1 and 2, have room for improvement in terms of storage stability in temperature environments near 40° C. when used in water-based resin compositions.

Further, although the dispersibility is excellent when used in a water-based resin composition, when used in a resin composition containing a hydrophobic solvent, there is room for improvement in the storage stability in temperature environments near 40° C.

Further, because the variety of readily available isocyanates is not particularly large, the structures of conventionally proposed uretonimine group-containing compounds are substantially limited. Furthermore, because use of an uretonimine depends on the reaction characteristics of the dissociation into a carbodiimide compound and an isocyanate compound, application of an uretonimine group-containing compound to a coating material or the like does not necessarily yield the desired characteristics.

Further, conventionally proposed uretonimine group-containing compounds still have room for improvement in terms of the storage stability when used in a water-based resin composition.

The present invention has been developed in light of the above circumstances, and provides a novel carbodiimide compound and a curing agent composition containing the carbodiimide compound that exhibits excellent storage stability when used as a resin composition. Further, the present invention also provides a resin composition, a coating material composition and a resin cured product that use the curing agent composition.

Further, in light of the above circumstances, the present invention also provides a novel compound having a uretonimine group and a method for producing the same, as well as a curing agent composition that contains this compound and exhibits excellent storage stability when used as a resin composition. Furthermore, the present invention also provides a resin composition, a coating material composition and a resin cured product that use the curing agent composition.

Means for Solving the Problems

In other words, the present invention includes the aspects described below.

(1) A compound having an uretonimine group, the compound containing, as a structural unit, a carbodiimide compound derived from at least one of an aliphatic diisocyanate and an aromatic diisocyanate, and also containing an isocyanate compound as a structural unit, wherein the residue obtained by removing an isocyanate group from the isocyanate compound and the residue obtained by removing a carbodiimide group from the carbodiimide compound are different.

(2) The compound according to (1), represented by general formula (1) shown below.

[Chemical formula 1]

$Q^1\text{-}X^1\text{—}Y^1\text{-}Q^2$ (1)

(In general formula (1), $X^1$ represents a group containing at least one group represented by general formula (1-1) shown below. In those cases where $X^1$ contains two or more groups represented by general formula (1-1) shown below, the plurality of groups represented by general formula (1-1) shown below may be the same or different. $Y^1$ is a group represented by general formula (1-2) shown below. Each of $Q^1$ and $Q^2$ independently represents a hydrogen atom, a group represented by general formula (1-3) shown below, a group represented by general formula (1-4) shown below, or a group represented by general formula (1-5) shown below.)

[Chemical formula 2]

\*—$X^2$—$Z^1$—\* (1-1)

\*—$Y^2$—\* (1-2)

\*—NCO (1-3)

\*—$Z^2$—$Q^3$ (1-4)

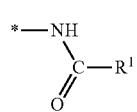
(1-5)

(In general formula (1-1) to general formula (1-5), each asterisk represents a bonding site. Each of $X^2$ and $Y^2$ independently represents a residue obtained by removing two isocyanate groups from at least one diisocyanate among an aliphatic diisocyanate and an aromatic diisocyanate. $Q^3$ represents a hydrogen atom or a monovalent organic group of at least 1 but not more than 15 carbon atoms. $Z^1$ is a group represented by general formula (1-a) shown below or a group represented by general formula (1-b) shown below. $Z^2$ is a group represented by general formula (1-a) shown below, a group represented by general formula (1-b) shown below, a group represented by general formula (1-c) shown below, or a group represented by general formula (1-d) shown below. $X^2$ contains at least one group represented by general formula (1-b) shown below. $R^1$ represents a residue obtained by removing the hydrogen atom from a terminal hydroxyl group of a monofunctional polyalkylene oxide poly ether alcohol.)

[Chemical formula 3]

\*—N=C=N—\* (1-a)

(1-b)

(1-c)

(1-d)

(In general formula (1-a), general formula (1-b), general formula (1-c) and general formula (1-d), each asterisk represents a bonding site. $Y^{11}$ represents a residue obtained by removing one isocyanate group from an isocyanate compound.)

(3) The compound according to (1) or (2), wherein in a spectrum measured by infrared spectroscopy, the ratio of the absorbance attributable to carbodiimide groups relative to the absorbance attributable to uretonimine groups and urethane groups is at least 0 but less than 1.5.

(4) The compound according to (2), wherein the monofunctional polyalkylene oxide poly ether alcohol is a polyethylene glycol monoalkyl ether, a polypropylene glycol monoalkyl ether, or a copolymer thereof.

(5) The compound according to (2) or (4), wherein $R^1$ is a group represented by general formula (II-1) shown below or a group represented by general formula (II-2) shown below.

[Chemical formula 4]

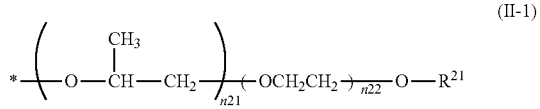
(II-1)

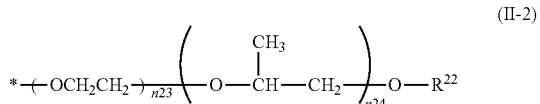
(II-2)

(In general formula (II-1), each of n21 and n22 independently represents an integer of at least 1 but not more than 30. $R^{21}$ represents an alkyl group of at least 1 but not more than 12 carbon atoms that may contain a carbonyl group.

In general formula (II-2), each of n23 and n24 independently represents an integer of at least 1 but not more than 30. $R^{22}$ represents an alkyl group of at least 1 but not more than 12 carbon atoms that may contain a carbonyl group.

Each asterisk represents a bonding site.)

(6) The compound according to any one of (2), (4) or (5), wherein $X^1$ is a group containing one or more of at least one type of group selected from the group consisting of groups represented by general formula (III-1-1) shown below, groups represented by general formula (III-2-1) shown below, groups represented by general formula (III-2-2) shown below, groups represented by general formula (III-3-1) shown below, groups represented by general formula (III-5-1) shown below, groups represented by general formula (III-6-1) shown below, groups represented by general formula (VI-1-1) shown below, groups represented by general formula (VI-2-1) shown below, and groups represented by general formula (VI-3-1) shown below, and $Y^1$ is a group represented by general formula (III-1) shown below, a group represented by general formula (III-2) shown below, a group represented by general formula (III-3) shown below, a group represented by general formula (III-5) shown below, a group represented by general formula (III-6) shown below, a group represented by general formula (VI-1) shown below, a group represented by general formula (VI-2) shown below, or a group represented by general formula (VI-3) shown below.

[Chemical formula 5]

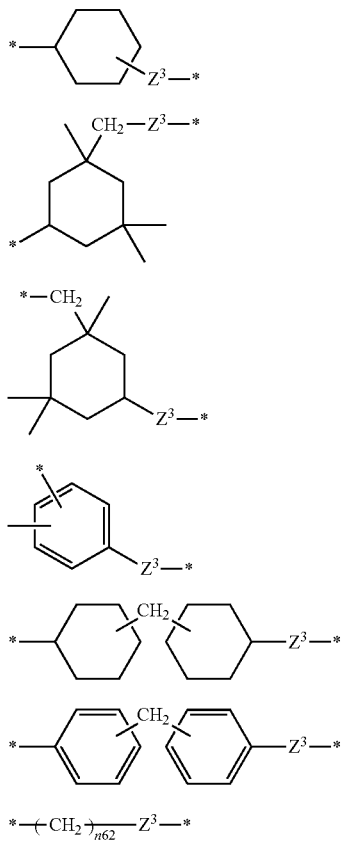

(III-1-1)

(III-2-1)

(III-2-2)

(III-3-1)

(III-5-1)

(III-6-1)

(VI-1-1)

(VI-2-1)

(VI-3-1)

(In the formulas, each asterisk represents a bonding site. Further, n62 represents an integer of at least 1 but not more than 10. $Z^3$ represents a group represented by general formula (1-a) shown above or a group represented by general formula (1-b) shown above.)

[Chemical formula 6]

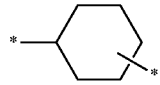
(III-1)

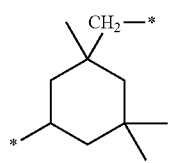
(III-2)

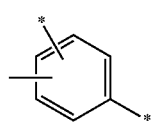
(III-3)

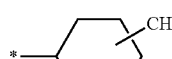
(III-5)

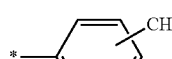
(III-6)

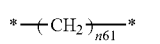
(VI-1)

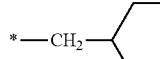
(VI-2)

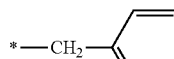
(VI-3)

(In the formulas, each asterisk represents a bonding site. Further, n61 represents an integer of at least 1 but not more than 10.)

(7) The compound according to (5) or (6), wherein $X^2$ and $Y^2$ are groups represented by general formula (VI) shown below.

[Chemical formula 7]

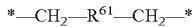
(VI)

(In general formula (VI), $R^{61}$ represents an alkylene group of at least 1 but not more than 18 carbon atoms or an arylene group of at least 6 but not more than 18 carbon atoms. The alkylene group and the arylene group may each have at least one functional group selected from the group consisting of an isocyanurate group, allophanate group, biuret group, uretdione group, iminooxadiazinedione group and urethane group. Each asterisk represents a bonding site.)

(8) The compound according to (7), wherein each of $X^2$ and $Y^2$ independently represents at least one group selected from the group consisting of groups represented by general formula (VI-1) shown below, groups represented by general formula (VI-2) shown below and groups represented by general formula (VI-3) shown below.

[Chemical formula 8]

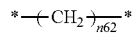
(VI-1)

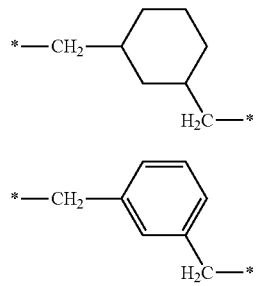
(VI-2)

(VI-3)

(In the formulas, each asterisk represents a bonding site. In general formula (VI-1), n61 represents an integer of at least 1 but not more than 10.)

(9) The compound according to any one of (1) to (8), wherein the carbodiimide compound is a carbodiimide compound derived from an aliphatic diisocyanate, and the isocyanate compound is an aliphatic isocyanate compound.

(10) The compound according to (9), wherein among the carbon atom that is bonded to the uretonimine group in the residue obtained by removing an isocyanate group from the isocyanate compound, and the carbon atom that is bonded to the uretonimine group in the residue obtained by removing a carbodiimide group from the carbodiimide compound,
one of the carbon atoms is a primary carbon atom or a primary carbon atom to which an electron-withdrawing group is bonded, and the other carbon atom is a secondary carbon atom, or
one of the carbon atoms is a primary carbon atom to which an electron-withdrawing group is bonded, and the other carbon atom is a primary carbon atom to which an electron-withdrawing group is not bonded.

(11) The compound according to (2), wherein the isocyanate compound is at least one of an isocyanate derived from an amino acid and a trifunctional or higher isocyanate.

(12) The compound according to (11), wherein the trifunctional or higher isocyanate is a trifunctional isocyanate.

(13) The compound according to (12), wherein the trifunctional isocyanate is a compound represented by general formula (1-B)-3c shown below.

[Chemical formula 9]

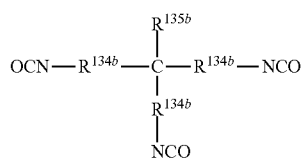
(1-B)-3c (In general formula (1-B)-3c, each of the plurality of $R^{134b}$ groups independently represents a single bond, or a divalent hydrocarbon group of at least 1 but not more than 20 carbon atoms that may contain at least one group selected from the group consisting of an ether group and an ester group. $R^{135b}$ represents a hydrogen atom or a monovalent hydrocarbon group of at least 1 but not more than 12 carbon atoms.)

(14) The compound according to (11), wherein the isocyanate having a group derived from an amino acid is an isocyanate having a group represented by formula (5) shown below.

[Chemical formula 10]

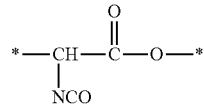
(5)

(In formula (5), each asterisk represents a bonding site.

(15) A carbodiimide compound, represented by general formula (2) shown below.

[Chemical formula 11]

$Q^{21}$-$X^{21}$—$Y^{21}$-$Q^{22}$ (2)

(In general formula (2), $X^{21}$ is a group containing at least one group represented by general formula (2-1) shown below. In those cases where $X^{21}$ contains two or more groups represented by general formula (2-1) shown below, the plurality of groups represented by general formula (2-1) shown below may be the same or different. $Y^{21}$ is a group represented by general formula (1-2) shown below. Each of $Q^{21}$ and $Q^{22}$ independently represents a hydrogen atom, a group represented by general formula (1-3) shown below, a group represented by general formula (1-4) shown below, or a group represented by general formula (1-5) shown below.)

[Chemical formula 12]

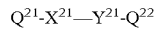
(2-1)

(In general formula (2-1), $X^{22}$ represents a residue obtained by removing two isocyanate groups from at least one diisocyanate among an aliphatic diisocyanate and an aromatic diisocyanate.)

[Chemical formula 13]

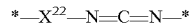 (1-2)

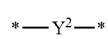 (1-3)

 (1-4)

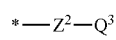 (1-5)

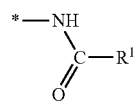

(In general formula (1-2) to general formula (1-5), each asterisk represents a bonding site. $Y^2$ represents a residue obtained by removing two isocyanate groups from at least one diisocyanate among an aliphatic diisocyanate and an aromatic diisocyanate. $Q^3$ represents a hydrogen atom or a monovalent organic group of at least 1 but not more than 15 carbon atoms. $Z^2$ is a group represented by general formula (1-a) shown below, a group represented by general formula (1-c) shown below, or a group represented by general formula (1-d) shown below. $R^1$ represents a residue obtained by removing the hydrogen atom from a terminal hydroxyl group of a monofunctional polyalkylene oxide polyether alcohol.)

[Chemical formula 14]

*—N=C=N—*  (1-a)

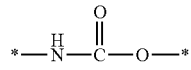  (1-c)

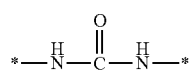  (1-d)

(In general formula (1-a), general formula (1-c) and general formula (1-d), each asterisk represents a bonding site.)

(16) The compound according to (15), wherein
$X^{21}$ is a group containing one or more of at least one type of group selected from the group consisting of groups represented by general formula (III-1-2) shown below, groups represented by general formula (III-2-3) shown below, groups represented by general formula (III-2-4) shown below, groups represented by general formula (III-3-2) shown below, groups represented by general formula (III-5-2) shown below, groups represented by general formula (III-6-2) shown below, groups represented by general formula (VI-1-2) shown below, groups represented by general formula (VI-2-2) shown below, and groups represented by general formula (VI-3-2) shown below, and
$Y^{21}$ is a group represented by general formula (III-1) shown below, a group represented by general formula (III-2) shown below, a group represented by general formula (III-3) shown below, a group represented by general formula (III-5) shown below, a group represented by general formula (III-6) shown below, a group represented by general formula (VI-1) shown below, a group represented by general formula (VI-2) shown below, or a group represented by general formula (VI-3) shown below.

[Chemical formula 15]

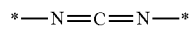 (III-1-2)

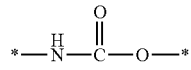 (III-2-3)

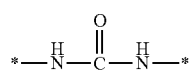 (III-2-4)

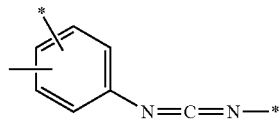 (III-3-2)

 (III-5-2)

 (III-6-2)

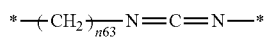 (VI-1-2)

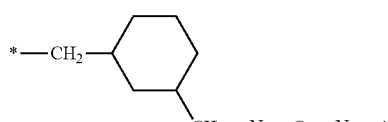 (VI-2-2)

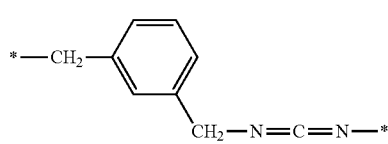 (VI-3-2)

(In the formulas, each asterisk represents a bonding site. Further, n63 represents an integer of at least 1 but not more than 10.)

[Chemical formula 16]

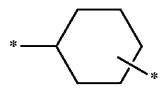 (III-1)

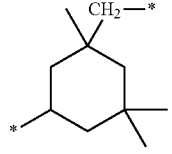 (III-2)

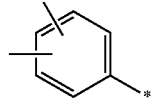 (III-3)

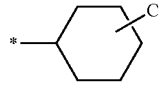 (III-5)

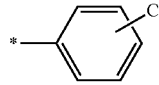 (III-6)

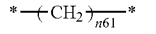 (VI-1)

-continued

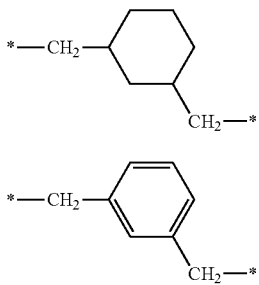

(VI-2)

(VI-3)

(In the formulas, each asterisk represents a bonding site. Further, n61 represents an integer of at least 1 but not more than 10.)

(17) The compound according to (16), wherein each of $X^{22}$ and $Y^{21}$ independently represents a group represented by general formula (VI) shown below.

[Chemical formula 17]

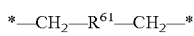

(VI)

(In general formula (VI), $R^{61}$ represents an alkylene group of at least 1 but not more than 18 carbon atoms or an arylene group of at least 6 but not more than 18 carbon atoms. The alkylene group and the arylene group may each have at least one functional group selected from the group consisting of an isocyanurate group, allophanate group, biuret group, uretdione group, iminooxadiazinedione group and urethane group. Each asterisk represents a bonding site.)

(18) The compound according to (17), wherein each of $X^{22}$ and $Y^{21}$ independently represents at least one group selected from the group consisting of groups represented by general formula (VI-1) shown below, groups represented by general formula (VI-2) shown below and groups represented by general formula (VI-3) shown below.

[Chemical formula 18]

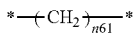

(VI-1)

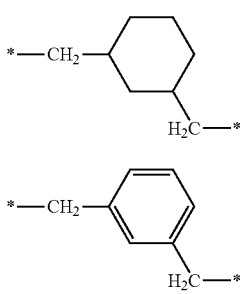

(VI-2)

(VI-3)

(In the formulas, each asterisk represents a bonding site. In general formula (VI-1), n61 represents an integer of at least 1 but not more than 10.)

(19) A method for producing the compound according to (2), the method including:
producing a compound having an uretonimine group represented by general formula (1) shown above by reacting a carbodiimide compound represented by general formula (2) shown below and an isocyanate compound represented by general formula (3) shown below.

[Chemical formula 19]

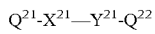

$Q^{21}\text{-}X^{21}\text{—}Y^{21}\text{-}Q^{22}$ (2)

(In general formula (2), $X^{21}$ is a group containing at least one group represented by general formula (2-1) shown below. In those cases where $X^{21}$ contains two or more groups represented by general formula (2-1) shown below, the plurality of groups represented by general formula (2-1) shown below may be the same or different. $Y^{21}$ is a group represented by general formula (1-2) shown below. Each of $Q^{21}$ and $Q^{22}$ independently represents a hydrogen atom, a group represented by general formula (1-3) shown below, a group represented by general formula (1-4) shown below, or a group represented by general formula (1-5) shown below.)

[Chemical formula 20]

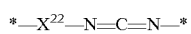

*—$X^{22}$—N=C=N—* (2-1)

(In general formula (2-1), $X^{22}$ represents a residue obtained by removing two isocyanate groups from at least one diisocyanate among an aliphatic diisocyanate and an aromatic diisocyanate.)

[Chemical formula 21]

 (1-2)

*—$Y^2$—*

 (1-3)

*—NCO

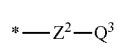 (1-4)

*—$Z^2$—$Q^3$

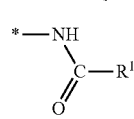 (1-5)

(In general formula (1-2) to general formula (1-5), each asterisk represents a bonding site. $Y^2$ represents a residue obtained by removing two isocyanate groups from at least one diisocyanate among an aliphatic diisocyanate and an aromatic diisocyanate. $Q^3$ represents a hydrogen atom or a monovalent organic group of at least 1 but not more than 15 carbon atoms. $Z^2$ is a group represented by general formula (1-a) shown below, a group represented by general formula (1-c) shown below, or a group represented by general formula (1-d) shown below. $R^1$ represents a residue obtained by removing the hydrogen atom from a terminal hydroxyl group of a monofunctional polyalkylene oxide polyether alcohol.)

[Chemical formula 22]

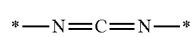 (1-a)

*—N=C=N—*

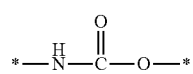 (1-c)

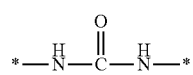 (1-d)

(In general formula (1-a), general formula (1-c) and general formula (1-d), each asterisk represents a bonding site.)

[Chemical formula 23]

$$R^3-NCO \qquad (3)$$

(In general formula (3), $R^3$ represents a residue obtained by removing one isocyanate group from an isocyanate compound.)

(20) A curing agent composition, containing the compound according to any one of (1) to (18).

(21) A resin composition, containing the curing agent composition according to (20) and a compound having a carboxyl group.

(22) A coating material composition, containing the resin composition according to (21).

(23) A resin cured product, obtained by curing the coating material composition according to (22).

Effects of the Invention

The compound of an aspect described above is able to provide a novel compound having a uretonimine group. The curing agent composition described above is able to provide a curing agent composition that contains this compound and exhibits excellent storage stability when used in a resin composition. The resin composition of an aspect described above contains the above curing agent composition, and exhibits excellent storage stability.

The compound of an aspect described above is able to provide a novel carbodiimide compound. The curing agent composition described above is able to provide a curing agent composition that contains this compound and exhibits excellent storage stability when used in a resin composition. The resin composition of an aspect described above contains the above curing agent composition, and exhibits excellent storage stability.

EMBODIMENTS FOR CARRYING OUT THE INVENTION

Embodiments for carrying out the present invention (hereafter referred to as "embodiments of the present invention") are described below in detail. The following embodiments of the present invention are provided as examples for describing the present invention, but the present invention is not limited to the following embodiments. The present invention can also be carried out by appropriate modification of the following embodiments within the scope of the invention.

<<Uretonimine group-Containing Compound>>

A compound of this embodiment of the present invention has an uretonimine group. Further, a compound of this embodiment of the present invention is a compound having an uretonimine group containing, as a structural unit, a carbodiimide compound derived from at least one of an aliphatic diisocyanate and an aromatic diisocyanate, and also containing an isocyanate compound as a structural unit. Furthermore, the residue obtained by removing an isocyanate group from the isocyanate compound and the residue obtained by removing a carbodiimide group from the carbodiimide compound are different.

In the compound of this embodiment of the present invention, by appropriate adjustment of the degree of steric hindrance between the residue obtained by removing an isocyanate group from the isocyanate compound and the residue obtained by removing a carbodiimide group from the carbodiimide compound, the balance between bonding and dissociation of the isocyanate compound and the carbodiimide compound can be adjusted, and a combination of superior storage stability and curability at low temperatures such as 80° C. can be achieved. Further, by controlling the degree of steric hindrance mentioned above, the productivity of the compound of this embodiment of the present invention can be improved. Specifically, in those cases where, for example, at least one of the carbon atoms among the carbon atom adjacent to the isocyanate group in the isocyanate compound and the carbon atom adjacent to the carbodiimide group in the carbodiimide compound is either a primary carbon atom to which an electron-withdrawing group is bonded or a secondary carbon atom, the dissociability of the isocyanate compound and the carbodiimide compound can be further improved, and the curability at low temperatures such as 80° C. can be further improved. On the other hand, in those cases where, for example, at least one carbon atom among the carbon atom adjacent to the isocyanate group in the isocyanate compound and the carbon atom adjacent to the carbodiimide group in the carbodiimide compound is a primary carbon atom to which an electron-withdrawing group is not bonded, the bonding between the isocyanate compound and the carbodiimide compound can be further enhanced, enabling the storage stability to be further improved.

This type of compound having an uretonimine group is preferably a compound represented by general formula (1) shown below.

[Chemical formula 24]

$$Q^1\text{-}X^1-Y^1\text{-}Q^2 \qquad (1)$$

In general formula (1), $X^1$ represents a group containing at least one group represented by general formula (1-1) shown below. In those cases where $X^1$ contains two or more groups represented by general formula (1-1) shown below, the plurality of groups represented by general formula (1-1) shown below may be the same or different. Further, $X^1$ may contain at least one but not more than 100 of the groups represented by general formula (1-1) shown below. $Y^1$ is a group represented by general formula (1-2) shown below. Each of $Q^1$ and $Q^2$ independently represents a hydrogen atom, a group represented by general formula (1-3) shown below, a group represented by general formula (1-4) shown below, or a group represented by general formula (1-5) shown below.

[Chemical formula 25]

 (1-1)

 (1-2)

 (1-3)

 (1-4)

 (1-5)

In general formula (1-1) to general formula (1-5), each asterisk represents a bonding site. Each of $X^2$ and $Y^2$ independently represents a residue obtained by removing two isocyanate groups from at least one diisocyanate among an aliphatic diisocyanate and an aromatic diisocyanate. $Q^3$ represents a hydrogen atom or a monovalent organic group of at least 1 but not more than 15 carbon atoms. $Z^1$ is a group represented by general formula (1-a) shown below or a group represented by general formula (1-b) shown below. $Z^2$ is a group represented by general formula (1-a) shown below, a group represented by general formula (1-b) shown below, a group represented by general formula (1-c) shown below, or a group represented by general formula (1-d) shown below. $X^2$ contains at least one group represented by general formula (1-b) shown below. $R^1$ represents a residue obtained by removing the hydrogen atom from a terminal hydroxyl group of a monofunctional polyalkylene oxide poly ether alcohol.

[Chemical formula 26]

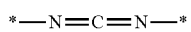
(1-a)

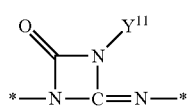
(1-b)

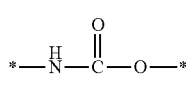
(1-c)

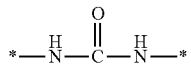
(1-d)

In general formula (1-a), general formula (1-b), general formula (1-c) and general formula (1-d), each asterisk represents a bonding site. $Y^{11}$ represents a residue obtained by removing one isocyanate group from an isocyanate compound.

[$X^2$ and $Y^2$]

Each of $X^2$ and $Y^2$ independently represents a residue obtained by removing two isocyanate groups from at least one diisocyanate among an aliphatic diisocyanate and an aromatic diisocyanate. Among the various possibilities, each of $X^2$ and $Y^2$ is preferably an aliphatic hydrocarbon group of at least 1 but not more than 22 carbon atoms, or an aromatic hydrocarbon group of at least 6 but not more than 22 carbon atoms. Specific examples include linear hydrocarbon groups, groups derived from unsubstituted alicyclic hydrocarbons, groups derived from alkyl-substituted cyclohexanes, groups derived from dialkyl-substituted cyclohexanes, groups derived from trialkyl-substituted cyclohexanes, monoalkyl-substituted benzenes, dialkyl-substituted benzenes, and groups derived from aromatic hydrocarbons.

Examples of the linear hydrocarbon groups include methylene, dimethylene, trimethylene, tetramethylene, pentamethylene, hexamethylene and octamethylene groups.

Examples of unsubstituted alicyclic hydrocarbons that can yield divalent groups include cyclopentane, cyclohexane, cycloheptane, cyclooctane and bis(cyclohexyl)alkanes.

Examples of alkyl-substituted cyclohexanes that can yield divalent groups include methylcyclohexane (each of the isomers), ethylcyclohexane (each of the isomers), propylcyclohexane (each of the isomers), butylcyclohexane (each of the isomers), pentylcyclohexane (each of the isomers), and hexylcyclohexane (each of the isomers).

Examples of dialkyl-substituted cyclohexanes that can yield divalent groups include dimethylcyclohexane (each of the isomers), diethylcyclohexane (each of the isomers), and dibutylcyclohexane (each of the isomers).

Examples of trialkyl-substituted cyclohexanes that can yield divalent groups include 1,5,5-trimethylcyclohexane, 1,5,5-triethylcyclohexane, 1,5,5-tripropylcyclohexane (each of the isomers), and 1,5,5-tributylcyclohexane (each of the isomers).

Examples of monoalkyl-substituted benzenes that can yield divalent groups include toluene, ethylbenzene and propylbenzene.

Examples of dialkyl-substituted benzenes that can yield divalent groups include xylene, diethylbenzene and dipropylbenzene.

Examples of aromatic hydrocarbons that can yield divalent groups include diphenylalkanes and benzene.

For this type of $X^2$ or $Y^2$ group, a group represented by formula (III-1) shown below, a group represented by formula (III-2) shown below, a group represented by formula (III-3) shown below, a group represented by formula (III-5) shown below, a group represented by formula (III-6) shown below, a group represented by general formula (VI-1) shown below, a group represented by general formula (VI-2) shown below, or a group represented by general formula (VI-3) shown below is particularly preferred.

In other words, $X^1$ is preferably a group containing one or more of at least one type of group selected from the group consisting of groups represented by general formula (III-1-1) shown below, groups represented by general formula (III-2-1) shown below, groups represented by general formula (III-2-2) shown below, groups represented by general formula (III-3-1) shown below, groups represented by general formula (III-5-1) shown below, groups represented by general formula (III-6-1) shown below, groups represented by general formula (VI-1-1) shown below, groups represented by general formula (VI-2-1) shown below, and groups represented by general formula (VI-3-1) shown below.

[Chemical formula 27]

(III-1-1)

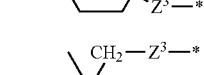
(III-2-1)

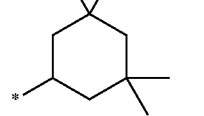
(III-2-2)

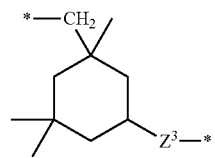
(III-3-1)

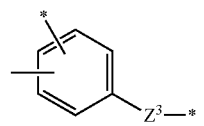

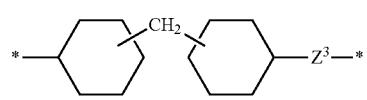
(III-5-1)

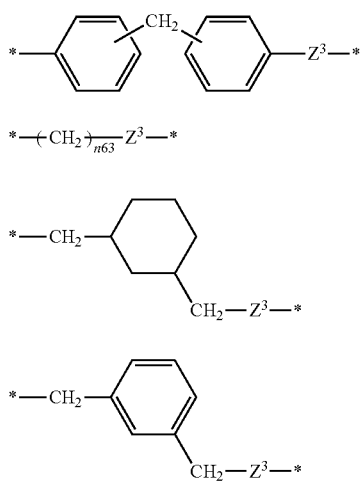

In the formulas, each asterisk represents a bonding site. Further, n62 represents an integer of at least 1 but not more than 10. $Z^3$ represents a group represented by general formula (1-a) shown above or a group represented by general formula (1-b) shown above.

Further, $Y^1$ is preferably a group represented by general formula (III-1) shown below, a group represented by general formula (III-2) shown below, a group represented by general formula (III-3) shown below, a group represented by general formula (III-5) shown below, a group represented by general formula (III-6) shown below, a group represented by general formula (VI-1) shown below, a group represented by general formula (VI-2) shown below, or a group represented by general formula (VI-3) shown below.

[Chemical formula 28]

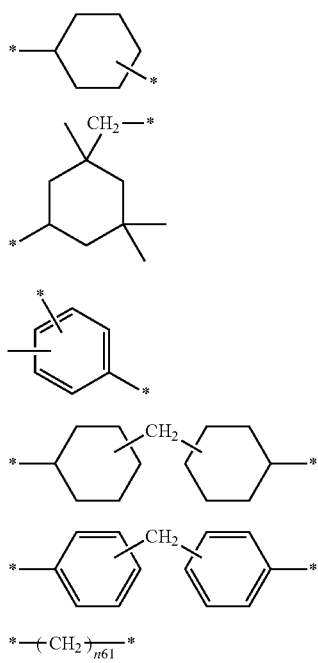

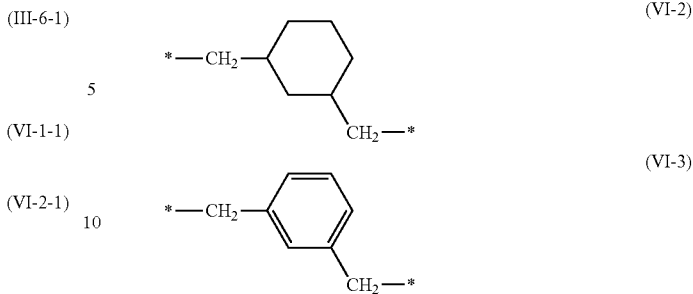

In the formulas, each asterisk represents a bonding site. Further, n61 represents an integer of at least 1 but not more than 10.

[$Q^3$]

In general formula (1-4), $Q^3$ represents a hydrogen atom or a monovalent organic group of at least 1 but not more than 15 carbon atoms. Among the various possibilities, $Q^3$ is preferably an aliphatic hydrocarbon group of at least 1 but not more than 12 carbon atoms, or an aromatic hydrocarbon group of at least 6 but not more than 12 carbon atoms.

Examples of preferred aliphatic groups include a methyl group, ethyl group, propyl group, butyl group, pentyl group, hexyl group, heptyl group, octyl group, nonyl group, decyl group, dodecyl group, cyclopentyl group, cyclohexyl group, cyclooctyl group, methylcyclohexyl group, dimethylcyclohexyl group, ethylcyclohexyl group, diethylcyclohexyl group, and butylcyclohexyl group.

Examples of preferred aromatic groups include a phenyl group, naphthyl group, methylphenyl group, dimethylphenyl group, ethylphenyl group, diethylphenyl group, butylphenyl group, diphenyl group, and phenylmethylphenyl group.

<Preferred Uretonimine Group-Containing Compounds>

Among the various possibilities, the carbodiimide compound included as a structural unit in a compound (1) of an embodiment of the present invention is preferably a carbodiimide compound derived from an aliphatic diisocyanate.

Further, the isocyanate compound included as a structural unit in the compound of an embodiment of the present invention is preferably an aliphatic isocyanate compound.

Moreover, in the compound (1) of an embodiment of the present invention, it is preferable that among the carbon atom that is bonded to the uretonimine group in the residue obtained by removing an isocyanate group from the isocyanate compound, and the carbon atom that is bonded to the uretonimine group in the residue obtained by removing a carbodiimide group from the carbodiimide compound, one of the carbon atoms is a primary carbon atom or a primary carbon atom to which an electron-withdrawing group is bonded, and the other carbon atom is a secondary carbon atom. Alternatively, it is preferable that one of the carbon atoms is a primary carbon atom to which an electron-withdrawing group is bonded, and the other carbon atom is a primary carbon atom to which an electron-withdrawing group is not bonded.

In the case of a primary carbon atom to which an electron-withdrawing group is bonded or a secondary carbon atom, the dissociability of the isocyanate compound and the carbodiimide compound can be further improved, and the curability at low temperatures such as 80° C. can be further improved. On the other hand, in the case of a primary carbon atom to which an electron-withdrawing group is bonded, the bonding between the isocyanate compound and the carbodiimide compound can be further enhanced, enabling the storage stability to be further improved. Consequently, by using the above combinations, the bonding and dissociability between the isocyanate compound and the carbodiimide compound can be controlled, and a combination of favorable storage stability and good curability at low temperatures such as 80° C. can be achieved.

Here, an "electron-withdrawing group" means a substituent that withdraws an electron from a reaction center (or has the effect of lowering the electron density), and specific examples include a halogen atom, nitro group (—$NO_2$), cyano group (—CN), carboxyl group (—COOH), alkoxycarbonyl group (—COOR', wherein R' is an arbitrary alkyl group), amide group (—C(=O)—N<), and ketone group (>C=O).

Preferred examples of the compound (1) include compounds represented by general formula (1α) shown below (hereafter sometimes referred to as the compound (1α)). The compound (1α) is a compound having at least one uretonimine group.

[Chemical formula 29]

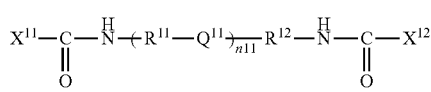

(1α)

(In general formula (1α), n11 represents an integer of at least 1 but not more than 100. Each of $X^{11}$ and $X^{12}$ independently represents a residue obtained by removing the hydrogen atom from a terminal hydroxyl group of a monofunctional polyalkylene oxide polyether alcohol. $Q^{11}$ represents a group represented by formula (1-a) shown below (hereafter sometimes referred to as "group (1-a)") or a group represented by general formula (1-b) shown below (hereafter sometimes referred to as "group (1-b)"). When n11 is 1, $Q^{11}$ is a group represented by general formula (1-b) shown below, and when n11 is 2 or greater, the plurality of Q11 groups may be the same or different. Each of $R^{11}$ and $R^{12}$ independently represents a residue obtained by removing two isocyanate groups from a diisocyanate.)

[Chemical formula 30]

*—N=C=N—* (1-a)

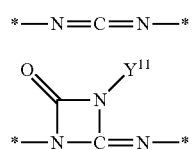

(1-b)

(In the formulas, each asterisk represents a bonding site. In general formula (1-b), $Y^{11}$ represents a residue obtained by removing one isocyanate group from an isocyanate compound. The diisocyanate mentioned above and this isocyanate compound are different compounds.)

Furthermore, in a spectrum measured by infrared spectroscopy, the compound (1α) has a ratio of the absorbance attributable to carbodiimide groups relative to the absorbance attributable to uretonimine groups and urethane groups that is at least 0 but less than 1.5, preferably at least 0 but not more than 1.4, more preferably at least 0 but not more than 1.0, and even more preferably at least 0 but not more than 0.5.

By ensuring that this ratio of the absorbance attributable to carbodiimide groups relative to the absorbance attributable to uretonimine groups and urethane groups falls within the above range, a more satisfactory amount of uretonimine groups is formed in the compound (1α), and the storage stability when used in a resin composition is more favorable.

It is generally known that in a spectrum measured by infrared spectroscopy, the absorbance attributable to the stretching vibration of uretonimine groups and urethane groups appears near 1720 $cm^{-1}$, whereas the absorbance attributable to the stretching vibration of carbodiimide groups appears near 2120 $cm^{-1}$.

The structure of the compound (1α) is described below in further detail.

[n11]

The integer n11 represents the number of repeating units of the structural unit —$R^{11}$-$Q^{11}$-, and is an integer of at least 1 but not more than 100.

[$X^{11}$ and $X^{12}$]

Each of $X^{11}$ and $X^{12}$ independently represents a residue obtained by removing the hydrogen atom from a terminal hydroxyl group of a monofunctional polyalkylene oxide polyether alcohol. As a result of including $X^{11}$ and $X^{12}$, the compound (1α) has excellent water dispersibility in water-based solvents. $X^{11}$ and $X^{12}$ may be the same or different, but are preferably the same in terms of ease of production.

(Monofunctional Polyalkylene Oxide Poly Ether Alcohol)

The monofunctional polyalkylene oxide poly ether alcohol used in the formation of $X^{11}$ and $X^{12}$ is a compound represented by general formula (IV) shown below.

[Chemical formula 31]

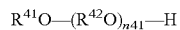

$R^{41}O$—$(R^{42}O)_{n41}$—H    (IV)

(In general formula (IV), $R^{41}$ represents an alkyl group of at least 1 but not more than 30 carbon atoms or an aryl group of at least 6 but not more than 30 carbon atoms that may contain a carbonyl group. $R^{42}$ represents an alkylene group of at least 1 but not more than 5 carbon atoms. Further, n41 is an integer of at least 1 but not more than 60.)

—$R^{41}$

The number of carbon atoms in the alkyl group that may contain a carbonyl group for $R^{41}$ is at least 1 but not more than 30, and from the viewpoint of improving the hydrophilicity of the polyisocyanate, the number of carbon atoms is preferably at least 1 but not more than 20, more preferably at least 1 but not more than 15, and even more preferably at least 1 but not more than 12.

The number of carbon atoms in the aryl group that may contain a carbonyl group for $R^{41}$ is at least 6 but not more than 30, and from the viewpoint of improving the hydrophilicity of the polyisocyanate, the number of carbon atoms is preferably at least 6 but not more than 20, more preferably at least 6 but not more than 15, and even more preferably at least 6 but not more than 12.

The alkyl group for $R^{41}$ may be chain-like or cyclic. The chain-like alkyl group may be either linear or branched. Examples of linear alkyl groups include a methyl group, ethyl group, n-propyl group, n-butyl group, n-pentyl group, n-hexyl group, n-heptyl group, n-octyl group, n-nonyl group, n-decyl group, n-undecyl group and n-dodecyl group. Examples of branched alkyl groups include an isopropyl group, isobutyl group, sec-butyl group, tert-butyl group, isopentyl group and isohexyl group. Examples of cyclic alkyl groups include a cyclopropyl group, cyclobutyl group, cyclopentyl group and cyclohexyl group.

Examples of the aryl group for $R^{41}$ include a phenyl group, naphthyl group, anthranyl group, and phenanthryl group.

Furthermore, the aryl group may have at least one hydrocarbon group selected from the group consisting of alkyl groups, alkenyl groups and aryl groups as a substituent. Examples of aryl groups having a substituent include a tolyl group, xylyl group, biphenyl group, styryl group and styrylphenyl group.

Furthermore, examples of alkyl groups and aryl groups containing a carbonyl group include groups represented by general formula (IVa) shown below (hereafter sometimes referred to as "group (IVa)").

[Chemical formula 32]

(IVa)

(In general formula (IVa), $R^{43}$ represents an alkyl group of at least 1 but not more than 29 carbon atoms or an aryl group of at least 6 but not more than 29 carbon atoms. The asterisk represents a bonding site.)

Examples of the alkyl group or aryl group for $R^{43}$ include alkyl groups of at least 1 but not more than 29 carbon atoms and aryl groups of at least 6 but not more than 29 carbon atoms among the groups exemplified above for $R^{41}$.

Among the various possibilities, $R^{41}$ is preferably a chain-like alkyl group that may contain a carbonyl group, more preferably a linear alkyl group that may contain a carbonyl group, even more preferably a linear alkyl group of at least 1 but not more than 12 carbon atoms that may contain a carbonyl group, and particularly preferably a methyl group or ethyl group.

$R^{42}$

The alkylene group of at least 1 but not more than 5 carbon atoms for $R^{42}$ may be chain-like or cyclic. The chain-like alkylene group may be either linear or branched. Examples of linear alkylene groups include a methylene group, ethylene group, trimethylene group, tetramethylene group and pentamethylene group. Examples of branched alkylene groups include a 1-methylethylene group (propylene group), 1-methyltrimethylene group, 2-methyltrimethylene group, 1,1-dimethylethylene group, 1-methyltetramethylene group and 2-methyltetramethylene group. Examples of cyclic alkylene groups include a cyclopropylene group, cyclobutylene group and cyclopentylene group.

Among these possibilities, $R^{42}$ is preferably a chain-like alkylene group, more preferably a linear alkylene group, even more preferably a linear alkylene group of at least 1 but not more than 3 carbon atoms, and particularly preferably a methylene group or ethylene group.

n41

Moreover, n41 represents the average number of alkylene oxide repeating units, and is an integer of at least 1 but not more than 60. The lower limit for the value of n41 is 1, preferably 2, and more preferably 5. On the other hand, the upper limit for the value of n41 is 60, preferably 40, and more preferably 30.

In other words, n41 is at least 1 but not more than 60, preferably at least 2 but not more than 40, and more preferably at least 5 but not more than 30.

By ensuring that n41 falls within the above range, the water dispersibility of the compound (1α) is more favorable.

The value of n41 can be calculated, for example, by proton nuclear magnetic resonance (NMR) spectroscopy, using the compound (1α) as a sample. Specifically, by comparing the integral of the relative intensity corresponding with the alkylene group and the integral of the relative intensity corresponding with the alkyl group, the average number of alkylene oxide repeating units in the compound (1α) can be calculated.

Examples of these types of monofunctional polyalkylene oxide poly ether alcohols include polymethylene glycol monoalkyl ethers, polyethylene glycol monoalkyl ethers, polyethylene glycol phenyl ether, polyethylene glycol alkylphenyl ethers, polyethylene glycol phenylphenyl ether, polyethylene glycol styrylphenyl ether, polyethylene glycol naphthyl ether, polypropylene glycol monoalkyl ethers, and copolymers of these compounds. Examples of the polyethylene glycol monoalkyl ethers include polyethylene glycol monomethyl ether, polyethylene glycol monoethyl ether, polyethylene glycol monopropyl ether, polyethylene glycol monobutyl ether and polyethylene glycol monolauryl ether. Examples of the polypropylene glycol monoalkyl ethers include polypropylene glycol monomethyl ether, polypropylene glycol monoethyl ether, polypropylene glycol monopropyl ether and polypropylene glycol monobutyl ether.

Examples of the copolymers include poly(oxyethylene-oxypropylene) (formed using at least one of random and block polymerization) glycol monomethyl ether, poly(oxyethylene-oxypropylene) (formed using at least one of random and block polymerization) glycol monobutyl ether, and poly(oxyethylene-oxytetramethylene) (formed using at least one of random and block polymerization) glycol polybutylene glycol monomethyl ether. Furthermore, nonionic surfactants and the like having a group containing two or more aromatic rings such as a (mono, di, tri, tetra or penta)-styrenated phenyl group, mono (di or tri)-styryl-methylphenyl group, tribenzylphenyl group, or β-naphthyl group may also be used as the monofunctional polyalkylene oxide poly ether alcohol. One of these monofunctional polyalkylene oxide polyether alcohols may be used alone, or a combination of two or more compounds may be used.

Among the various possibilities, the monofunctional polyalkylene oxide polyether alcohol is preferably a polyethylene glycol monomethyl ether, polypropylene glycol monomethyl ether, polyethylene glycol monobutyl ether, polypropylene glycol monobutyl ether, poly(oxyethylene-oxypropylene) (formed using at least one of random and block polymerization) glycol monomethyl ether, or poly(oxyethylene-oxypropylene) (formed using at least one of random and block polymerization) glycol monobutyl ether.

The lower limit for the molecular weight of the monofunctional polyalkylene oxide poly ether alcohol is preferably 50, more preferably 100, even more preferably 150, and particularly preferably 200. On the other hand, the upper limit for the molecular weight is preferably 3,000, more preferably 2,500, even more preferably 2,000, and particularly preferably 1,500.

In other words, the molecular weight of the monofunctional polyalkylene oxide polyether alcohol is preferably at least 50 but not more than 3,000, more preferably at least 100 but not more than 2,500, even more preferably at least 150 but not more than 2,000, and particularly preferably at least 200 but not more than 1,500.

Provided the molecular weight falls within the above range, the water dispersibility of the compound (1α) is more favorable.

In other words, examples of preferred $X^{11}$ and $X^{12}$ groups include groups represented by general formula (II-1) shown below (hereafter sometimes referred to as "group (II-1)") and groups represented by general formula (II-2) shown below (hereafter sometimes referred to as "group (II-2)"). By including a group (II-1) or group (II-2), the compound (1α) adopts a structure in which the main skeleton having a hydrophobic uretonimine group, a weakly hydrophilic propylene oxide repeating unit, and a strongly hydrophilic ethylene oxide repeating unit are bonded in sequence from the center of the molecule toward the terminals, and this enables more stable dispersion in water, and enables the penetration of carboxylic acids and alcohols into the uretonimine group to be controlled more effectively in water-based solvents. Further, in the group (II-1) or the group (II-2), the ethylene oxide repeating units and the propylene oxide repeating units may be formed by block polymerization or random polymerization.

[Chemical formula 33]

$$*\!\!\left(\!\!-\text{O}-\underset{|}{\overset{\text{CH}_3}{\text{CH}}}-\text{CH}_2\!\!-\!\!\right)_{\!n21}\!\!\left(\!\!-\text{OCH}_2\text{CH}_2\!\!-\!\!\right)_{\!n22}\!\!\text{O}-\text{R}^{21} \quad \text{(II-1)}$$

$$*\!\!-\!\!\left(\!\!-\text{OCH}_2\text{CH}_2\!\!-\!\!\right)_{\!n23}\!\!\left(\!\!-\text{O}-\underset{|}{\overset{\text{CH}_3}{\text{CH}}}-\text{CH}_2\!\!-\!\!\right)_{\!n24}\!\!\text{O}-\text{R}^{22} \quad \text{(II-2)}$$

(In general formula (II-1), each of n21 and n22 independently represents an integer of at least 1 but not more than 30. $R^{21}$ is an alkyl group of at least 1 but not more than 12 carbon atoms that may contain a carbonyl group.

In general formula (II-2), each of n23 and n24 independently represents an integer of at least 1 but not more than 30. $R^{22}$ is an alkyl group of at least 1 but not more than 12 carbon atoms that may contain a carbonyl group.

Each asterisk represents a bonding site.)
n21, n22, n23 and n24

Each of n21 and n24 independently represents a number of propylene oxide repeating units, whereas each of n22 and n23 independently represents a number of ethylene oxide repeating units. Each of n21, n22, n23 and n24 independently represents at least 1 but not more than 30, preferably at least 1 but not more than 20, more preferably at least 2 but not more than 15, and even more preferably at least 5 but not more than 10. By ensuring that n21, n22, n23 and n24 fall within the above range, the penetration of carboxylic acids and alcohols into the uretonimine group can be controlled more effectively in water-based solvents.

Further, the ratio of n21 relative to n22 (n21/n22) can be set, for example, to at least 0.8 but not more than 1.2, but is preferably 1.0.

Furthermore, the ratio of n24 relative to n23 (n24/n23) can be set, for example, to at least 0.8 but not more than 1.2, but is preferably 1.0.

By ensuring that the ratios n21/n22 and n24/n23 fall within the above range, the penetration of carboxylic acids and alcohols into the uretonimine group can be controlled more effectively in water-based solvents.
$R^{21}$ and $R^{22}$ Examples of the alkyl group that may contain a carbonyl group for $R^{21}$ and $R^{22}$ include the same groups as the alkyl groups of at least 1 but not more than 12 carbon atoms among the groups exemplified above for $R^{41}$. Of these, groups, $R^{21}$ is preferably an alkyl group of at least 1 but not more than 8 carbon atoms, more preferably a chain-like alkyl group of at least 1 but not more than 6 carbon atoms, and even more preferably a linear alkyl group of at least 1 but not more than 4 carbon atoms.

Examples of more preferred $X^{11}$ and $X^{12}$ groups include groups represented by general formula (II-1-1) shown below (hereafter sometimes referred to as "group (II-1-1)"), groups represented by general formula (II-1-2) shown below (hereafter sometimes referred to as "group (II-1-2)"), groups represented by general formula (II-2-1) shown below (hereafter sometimes referred to as "group (II-2-1)"), and groups represented by general formula (II-2-2) shown below (hereafter sometimes referred to as "group (II-2-2)").

[Chemical formula 34]

$$*\!\!\left(\!\!-\text{O}-\underset{|}{\overset{\text{CH}_3}{\text{CH}}}-\text{CH}_2\!\!-\!\!\right)_{\!n211}\!\!\left(\!\!-\text{OCH}_2\text{CH}_2\!\!-\!\!\right)_{\!n212}\!\!\text{O}-\text{CH}_3 \quad \text{(II-1-1)}$$

$$*\!\!\left(\!\!-\text{O}-\underset{|}{\overset{\text{CH}_3}{\text{CH}}}-\text{CH}_2\!\!-\!\!\right)_{\!n213}\!\!\left(\!\!-\text{OCH}_2\text{CH}_2\!\!-\!\!\right)_{\!n214}\!\!\text{O}-\text{C}_4\text{H}_9 \quad \text{(II-1-2)}$$

$$*\!\!-\!\!\left(\!\!-\text{OCH}_2\text{CH}_2\!\!-\!\!\right)_{\!n221}\!\!\left(\!\!-\text{O}-\underset{|}{\overset{\text{CH}_3}{\text{CH}}}-\text{CH}_2\!\!-\!\!\right)_{\!n222}\!\!\text{O}-\text{CH}_3 \quad \text{(II-2-1)}$$

$$*\!\!-\!\!\left(\!\!-\text{OCH}_2\text{CH}_2\!\!-\!\!\right)_{\!n223}\!\!\left(\!\!-\text{O}-\underset{|}{\overset{\text{CH}_3}{\text{CH}}}-\text{CH}_2\!\!-\!\!\right)_{\!n224}\!\!\text{O}-\text{C}_4\text{H}_9 \quad \text{(II-2-2)}$$

(In general formula (II-1-1), each of n211 and n212 independently represents an integer of at least 1 but not more than 30.

In general formula (II-1-2), each of n213 and n214 independently represents an integer of at least 1 but not more than 30.

In general formula (II-2-1), each of n221 and n222 independently represents an integer of at least 1 but not more than 30.

In general formula (II-2-2), each of n223 and n224 independently represents an integer of at least 1 but not more than 30.
[$R^{11}$ and $R^{12}$]

Each of $R^{11}$ and $R^{12}$ independently represents a residue obtained by removing two isocyanate groups from a diisocyanate, namely a divalent hydrocarbon group. $R^{11}$ and $R^{12}$ may be the same or different, but are preferably the same in terms of ease of production.

The divalent hydrocarbon group is preferably an aliphatic hydrocarbon group of at least 1 but not more than 22 carbon atoms or an aromatic hydrocarbon group of at least 6 but not more than 22 carbon atoms. Specific examples include linear hydrocarbon groups, unsubstituted alicyclic hydrocarbon groups (cycloalkylene groups), alkyl-substituted alicyclic hydrocarbon groups, dialkyl-substituted alicyclic hydrocarbon groups, trialkyl-substituted alicyclic hydrocarbon groups, groups obtained by bonding a linear hydrocarbon group and a trialkyl-substituted alicyclic hydrocarbon group, unsubstituted aromatic hydrocarbon groups, monoalkyl-substituted arylene groups, and dialkyl-substituted arylene groups.

Examples of the linear hydrocarbon groups include a methylene group, ethylene group, trimethylene group, tetramethylene group, pentamethylene group, hexamethylene group and octamethylene group.

Examples of the unsubstituted alicyclic hydrocarbon groups include a cyclopentylene group, cyclohexylene group, cycloheptylene group, cyclooctylene group, and alkylenebis(cyclohexylene) groups. Examples of the alkylenebis(cyclohexylene) groups include a methylenebis(cyclohexylene) group and an ethylenebis(cyclohexylene) group.

Examples of the alkyl-substituted alicyclic hydrocarbon groups include a methylcyclopentylene group, ethylcyclopentylene group, methylcyclohexylene group (each of the isomers), ethylcyclohexylene group (each of the isomers), propylcyclohexylene group (each of the isomers), butylcyclohexylene group (each of the isomers), pentylcyclohexylene group (each of the isomers), and hexylcyclohexylene group (each of the isomers).

Examples of the dialkyl-substituted alicyclic hydrocarbon groups include a dimethylcyclohexylene group (each of the isomers), diethylcyclohexylene group (each of the isomers), and dibutylcyclohexylene group (each of the isomers).

Examples of the trialkyl-substituted alicyclic hydrocarbon groups include a 1,5,5-trimethylcyclohexylene group, 1,5,5-triethylcyclohexylene group, 1,5,5-tripropylcyclohexylene group (each of the isomers), and 1,5,5-tributylcyclohexylene group (each of the isomers).

Examples of the groups obtained by bonding a linear hydrocarbon group and a trialkyl-substituted alicyclic hydrocarbon group include groups represented by formula (III-2) shown below (hereafter sometimes referred to as "group (III-2)").

[Chemical formula 35]

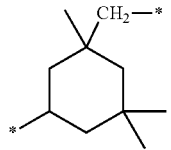

(III-2)

Examples of the unsubstituted aromatic hydrocarbon groups include a phenylene group and diphenylalkane-diyl groups.

Examples of the monoalkyl-substituted arylene groups include a toluene-diyl group, ethylphenylene group, and propylphenylene group.

Examples of the dialkyl-substituted arylene groups include a xylene-diyl group, diethylphenylene group, dipropylphenylene group, and tetramethylxylylene group.

Among the various possibilities, each of $R^{11}$ and $R^{12}$ is preferably an alkylenebis(cyclohexylene) group, group (III-2), diphenylalkane-diyl group, toluene-diyl group or tetramethylxylylene group, and is more preferably a group represented by formula (III-1) shown below (hereafter sometimes referred to a "group (III-1)"), a group (III-2), a group represented by formula (III-3) shown below (hereafter sometimes referred to a "group (III-3)"), a group represented by formula (III-4) shown below (hereafter sometimes referred to a "group (III-4)"), a group represented by formula (III-5) shown below (hereafter sometimes referred to a "group (III-5)"), or a group represented by formula (III-6) shown below (hereafter sometimes referred to a "group (III-6)").

[Chemical formula 36]

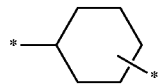
(III-1)

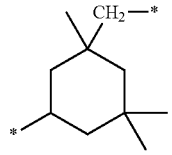
(III-2)

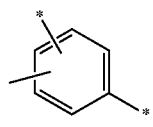
(III-3)

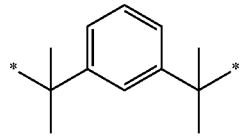
(III-4)

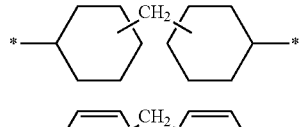
(III-5)

(III-6)

(In the formulas, each asterisk represents a bonding site.)

Further, among the various possibilities, a group (VI) is preferred as $R^{11}$ and $R^{12}$.

[Chemical formula 37]

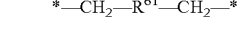

$$*-CH_2-R^{61}-CH_2-* \quad (VI)$$

(In general formula (VI), $R^{61}$ represents an alkylene group of at least 1 but not more than 18 carbon atoms, or an arylene group of at least 6 but not more than 18 carbon atoms. The alkylene group and the arylene group may each have at least one functional group selected from the group consisting of an isocyanurate group, allophanate group, biuret group, uretdione group, iminooxadiazinedione group and urethane group. Each asterisk represents a bonding site.)

($R^{61}$)

The alkylene group of at least 1 but not more than 18 carbon atoms for $R^{61}$ may be chain-like or cyclic. The chain-like alkylene group may be either linear or branched. Examples of linear alkylene groups include a methylene group, ethylene group, trimethylene group, tetramethylene group, pentamethylene group, hexamethylene group, heptamethylene group, and octamethylene group. Examples of branched alkylene groups include a 1-methylethylene group (propylene group), 1-methyltrimethylene group, 2-methyltrimethylene group, 1,1-dimethylethylene group, 1-methyltetramethylene group and 2-methyltetramethylene group. Examples of cyclic alkylene groups include a cyclopropylene group, cyclobutylene group, cyclopentylene group, cyclohexylene group, cycloheptylene group and cyclooctylene group.

Examples of the arylene group of at least 6 but not more than 18 carbon atoms for $R^{61}$ include a phenylene group and a naphthalene-diyl group.

Of the various possibilities, $R^{61}$ is preferably an ethylene group, trimethylene group, tetramethylene group, cyclohexylene group or phenylene group.

Preferred examples of the group (VI) include groups represented by general formula (VI-1) shown below (hereafter sometimes referred to a "group (VI-1)"), groups represented by general formula (VI-2) shown below (hereafter sometimes referred to a "group (VI-2)"), and groups represented by general formula (VI-3) shown below (hereafter sometimes referred to a "group (VI-3)").

[Chemical formula 38]

(VI-1)

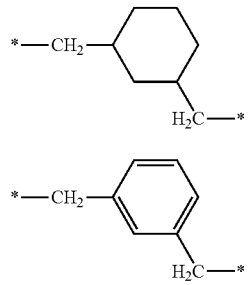

(In the formulas, each asterisk represents a bonding site. In general formula (VI-1), n61 represents an integer of at least 3 but not more than 10.)

Preferred examples of the group (VI-1) include a trimethylene group, tetramethylene group, pentamethylene group and hexamethylene group, and among these groups, a tetramethylene group, pentamethylene group or hexamethylene group is particularly preferred.

Further, in those cases where each of $R^{11}$ and $R^{12}$ is an alkylene group or arylene group having at least one functional group selected from the group consisting of an isocyanurate group, allophanate group, biuret group, uretdione group, iminooxadiazinedione group and urethane group, $R^{11}$ and $R^{12}$ are residues obtained by removing two isocyanate groups from a polyisocyanate derived from a diisocyanate. Among the various possibilities, the polyisocyanate is preferably a polyisocyanate having an isocyanurate group.

An "isocyanurate group" is a functional group obtained by reacting three isocyanate groups, and is a group represented by formula (VII-1) shown below.

An "allophanate group" is a functional group obtained by reacting the hydroxyl group of an alcohol and an isocyanate group, and is a group represented by formula (VII-2) shown below.

In general, a "biuret group" is a functional group obtained by reacting three isocyanate groups and a biuretizing agent, and is a group represented by formula (VII-3) shown below.

In general, an "uretdione group" is a functional group obtained by reacting two isocyanate groups, and is a group represented by formula (VII-4) shown below.

In general, an "iminooxadiazinedione group" is a functional group obtained by reacting three isocyanate groups, and is a group represented by formula (VII-5) shown below.

In general, a "urethane group" is a functional group obtained by reacting one isocyanate group and one hydroxyl group, and is a group represented by formula (VII-6) shown below.

[Chemical formula 39]

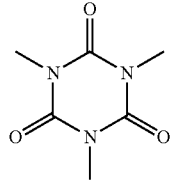

(VII-1)

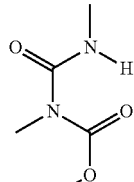

(VII-2)

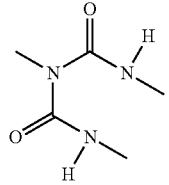

(VII-3)

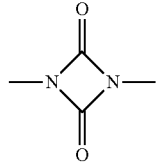

(VII-4)

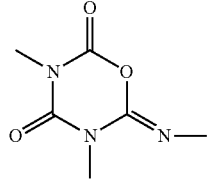

(VII-5)

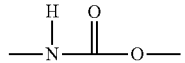

(VII-6)

$Q^{11}$ is the group (1-a) or the group (1-b). The group (1-a) is a carbodiimide group. The group (1-b) is an uretonimine group formed by reacting a carbodiimide group and the isocyanate group of an isocyanate compound.

When n11 is 1, $Q^{11}$ is the group (1-b), and when n11 is 2 or greater, the plurality of $Q^{11}$ groups may be the same or different, but from the viewpoint of the storage stability when used in a resin composition, the group (1-b) and the group (1-a) preferably exist in amounts that yield a ratio, in a spectrum measured by infrared spectroscopy, of the absorbance attributable to carbodiimide groups relative to the absorbance attributable to uretonimine groups and urethane groups that falls within the range described above.

[Chemical formula 40]

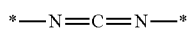

(1-a)

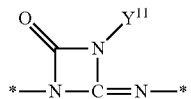

(1-b)

(In the formulas, each asterisk represents a bonding site. In general formula (1-b), $Y^{11}$ represents a residue obtained by removing one isocyanate group from an isocyanate compound. The diisocyanate mentioned above and this isocyanate compound are different compounds.)

($Y^{11}$)

$Y^{11}$ represents a residue obtained by removing one isocyanate group from an isocyanate compound.

The isocyanate compound used in the formation of the uretonimine group containing $Y^{11}$ is a compound having at least one isocyanate group, and may be any such compound that is different from the diisocyanate used in the formation of $R^{11}$ and $R^{12}$ described above.

Further, $Y^{11}$ may also be a residue obtained by removing one isocyanate group from an isocyanate compound having a group derived from an amino acid, wherein the isocyanate compound having a group derived from an amino acid is an isocyanate compound having a group represented by formula (5) shown below.

[Chemical formula 41]

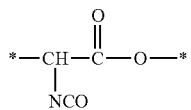

(5)

(In general formula (5), each asterisk represents a bonding site.)

The isocyanate compound used in the formation of the uretonimine group containing $Y^{11}$ is preferably at least one isocyanate compound selected from among isocyanates derived from an amino acid and trifunctional or higher isocyanates.

In other words, $Y^{11}$ is preferably at least one of a residue obtained by removing one isocyanate group from an isocyanate compound having a group derived from an amino acid, and a residue obtained by removing one isocyanate group from a trifunctional or higher isocyanate compound. The trifunctional or higher isocyanate compound is preferably a trifunctional isocyanate.

Examples of the isocyanate compound used in the formation of the uretonimine group containing $Y^{11}$ include compounds represented by general formula (I-B) shown below (hereafter sometimes referred to as "compound (I-B)"), and polyisocyanates obtained by polymerizing a diisocyanate monomer or triisocyanate monomer. Examples of the polyisocyanate include hexamethylene diisocyanate (hereafter sometimes abbreviated as HDI) based polyisocyanates and isophorone diisocyanate (hereafter sometimes abbreviated as IPDI) based polyisocyanates. Examples of the HDI-based polyisocyanates include biuret polyisocyanates and isocyanurate polyisocyanates.

[Chemical formula 42]

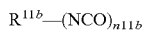

(I-B)

(In general formula (I-B), n11b represents an integer of 1 or greater. $R^{11b}$ is an organic group having a valence of n11b.)

[Compound (I-B)]

(n11b)

In general formula (I-B), if consideration is given to ease of production and ease of handling, then n11b is preferably an integer of at least 1 but not more than 5, and more preferably an integer of at least 1 but not more than 3.

($R^{11b}$)

In general formula (I-B), $R^{11b}$ is preferably an organic group of at least 3 but not more than 85 carbon atoms, and more preferably an organic group of at least 3 but not more than 30 carbon atoms. The organic group for $R^{11}$ is an aliphatic hydrocarbon group, an aromatic hydrocarbon group, or a group obtained by bonding an aliphatic hydrocarbon group and an aromatic hydrocarbon group. Specific examples of $R^{31}$ include cyclic hydrocarbon groups, acyclic hydrocarbon groups, groups in which an acyclic hydrocarbon group is bonded to at least one cyclic group, and groups in which one of these groups is covalently bonded to a specific non-metal atom. Examples of the cyclic groups include cyclic hydrocarbon groups, heterocyclic groups, heterocyclic spiro groups, and hetero-crosslinked cyclic groups. Examples of the alicyclic hydrocarbon groups include monocyclic hydrocarbon groups, condensed polycyclic hydrocarbon groups, crosslinked cyclic hydrocarbon groups, spiro hydrocarbon groups, linked ring hydrocarbon groups, and cyclic hydrocarbon groups having side chains. Examples of the above non-metal atom include carbon, oxygen, nitrogen, sulfur and silicon.

1. Monofunctional Isocyanate Compounds

In the compound (I-B), in the case of monofunctional isocyanate compounds in which n11b is 1 (namely, compounds having one isocyanate group in each molecule), preferred examples of the compound (I-B) include compounds represented by general formula (I-B)-1a shown below (hereafter sometimes referred to as "compound (I-B)-1a") and compounds represented by general formula (I-B)-1b shown below (hereafter sometimes referred to as "compound (I-B)-1b").

These compounds are merely examples of preferred compounds (I-B), and preferred examples of the compound (I-B) are not limited to these compounds.

[Chemical formula 43]

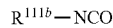

(I-B)-1a

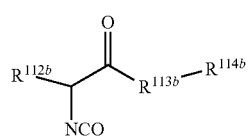

(I-B)-1b (In general formula (I-B)-1a, $R^{111b}$ represents a hydrocarbon group of at least 3 but not more than 85 carbon atoms.

In general formula (I-B)-1b, $R^{113b}$ represents an oxygen atom or a secondary amino group (—NH—). $R^{112b}$ represents a hydrogen atom, an aliphatic hydrocarbon group of at least 1 but not more than 10 carbon atoms, or an aromatic hydrocarbon group of at least 6 but not more than 10 carbon atoms. The aliphatic hydrocarbon group of at least 1 but not more than 10 carbon atoms and the aromatic hydrocarbon group of at least 6 but not more than 10 carbon atoms for $R^{112b}$ may also contain at least one atom selected from the group consisting of a sulfur atom, an oxygen atom and halogen atoms. $R^{114b}$ represents a monovalent aliphatic hydrocarbon group of at least 1 but not more than 10 carbon atoms, or a monovalent aromatic hydrocarbon group of at least 6 but not more than 10 carbon atoms.

The compound (I-B)-1b is a compound having an α-amino acid skeleton.

In an α-amino acid, the bonding mode of the amino group and the carboxyl group or the like to the α-carbon can adopt two different three dimensional modes, and these modes are differentiated as the D- and L-stereoisomers. The amino acid (and compound having an amino acid skeleton) used in the production of the above compound (I-B)-1b may be the D-isomer, the L-isomer, or a mixture or racemate thereof. Most amino acids that can be obtained industrially at low cost are amino acids produced by fermentation, and are almost all L-isomers, and these amino acids can be used favorably. In this description, the three-dimensional configuration is not shown, indicating that either the D-isomer or L-isomer may be used.

($R^{111b}$)

$R^{111b}$ represents a hydrocarbon group of at least 3 but not more than 85 carbon atoms. The hydrocarbon group for $R^{111b}$ may be an aliphatic hydrocarbon group or an aromatic hydrocarbon group. Examples of the hydrocarbon group for $R^{111b}$ include the same groups as the hydrocarbon groups exemplified above for $R^{11b}$.

($R^{112b}$ and $R^{114b}$)

Specific examples of the monovalent aliphatic hydrocarbon group of at least 1 but not more than 10 carbon atoms for $R^{112b}$ and $R^{114b}$ include a methyl group, ethyl group, propyl group, butyl group, pentyl group, hexyl group and decyl group. Specific examples of the monovalent aromatic hydrocarbon group of at least 6 but not more than 10 carbon atoms for $R^{112b}$ and $R^{114b}$ include a phenyl group, methylphenyl group, ethylphenyl group, butylphenyl group, dimethylphenyl group and diethylphenyl group. Further, the aliphatic hydrocarbon group of at least 1 but not more than 10 carbon atoms and the aromatic hydrocarbon group of at least 6 but not more than 10 carbon atoms for $R^{112b}$ may also contain at least one atom selected from the group consisting of a sulfur atom, an oxygen atom and halogen atoms. When the group contains a sulfur atom or an oxygen atom, a carbon atom that constitutes the aliphatic hydrocarbon group of at least 1 but not more than 10 carbon atoms or the aromatic hydrocarbon group of at least 6 but not more than 10 carbon atoms is substituted with the sulfur atom or oxygen atom.

($R^{113b}$)

$R^{113b}$ represents an oxygen atom (—O—) or a secondary amino group (—NH—). When $R^{113b}$ is an oxygen atom, the oxygen atom forms an ester linkage with the adjacent carbonyl group. Further, when $R^{113b}$ is a secondary amino group (—NH—), the amino group forms an amide linkage with the adjacent carbonyl group.

Preferred examples of the compound (I-B)-1a include cyclohexyl isocyanate and phenyl isocyanate.

Preferred examples of the compound (I-B)-1b include compounds represented by formula (I-B)-1b-1 shown below (hereafter sometimes abbreviated as "compound (I-B)-1b-1"), compounds represented by formula (I-B)-1b-2 shown below (hereafter sometimes abbreviated as "compound (I-B)-1b-2"), compounds represented by formula (I-B)-1b-3 shown below (hereafter sometimes abbreviated as "compound (I-B)-1b-3"), and compounds represented by formula (I-B)-1b-4 shown below (hereafter sometimes abbreviated as "compound (I-B)-1b-4").

These compounds are merely examples of preferred compounds (I-B), and preferred examples of the compound (I-B) are not limited to these compounds.

[Chemical formula 44]

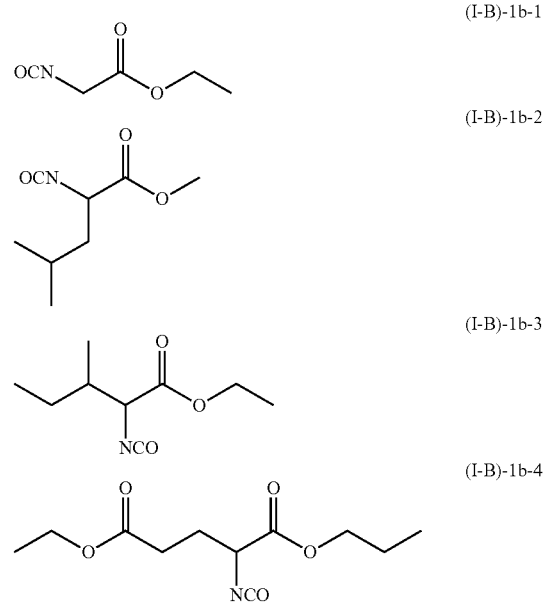

2. Difunctional Isocyanate Compounds

In the compound (I-B), in the case of difunctional isocyanate compounds in which n11b is 2 (namely, compounds having two isocyanate groups in each molecule), preferred examples of the compound (I-B) include compounds represented by general formula (I-B)-2a shown below (hereafter sometimes referred to as "compound (I-B)-2a"), compounds represented by general formula (I-B)-2b shown below (hereafter sometimes referred to as "compound (I-B)-2b"), compounds represented by general formula (I-B)-2c shown below (hereafter sometimes referred to as "compound (I-B)-2c"), and compounds represented by general formula (I-B)-2d shown below (hereafter sometimes referred to as "compound (I-B)-2d").

These compounds are merely examples of preferred compounds (I-B), and preferred examples of the compound (I-B) are not limited to these compounds.

[Chemical formula 45]

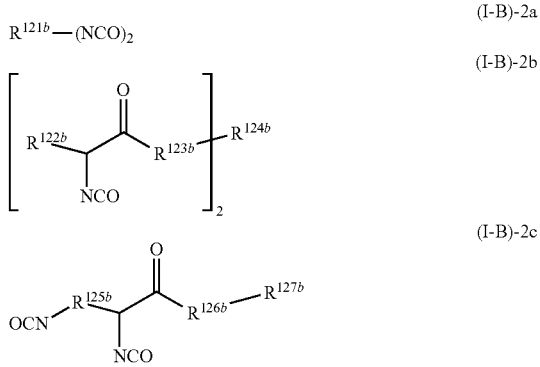

-continued (I-B)-2d

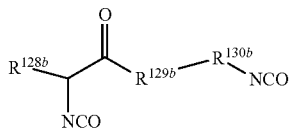

(In general formula (I-B)-2a, $R^{121b}$ is the same as $R^{111b}$ described above.

In general formula (I-B)-2b, $R^{122b}$ is the same as $R^{112b}$ described above. $R^{123b}$ is the same as $R^{113b}$ described above. $R^{124b}$ represents a divalent aliphatic hydrocarbon group of at least 1 but not more than 10 carbon atoms or a divalent aromatic hydrocarbon group of at least 6 but not more than 10 carbon atoms.

In general formula (I-B)-2c, $R^{125b}$ represents an alkylene group of at least 1 but not more than 5 carbon atoms. $R^{126b}$ is the same as $R^{113b}$ described above. $R^{127b}$ is the same as $R^{114b}$ described above.

In general formula (I-B)-2d, $R^{128b}$ is the same as $R^{112b}$ described above. $R^{129b}$ is the same as $R^{113b}$ described above. $R^{130b}$ is the same as $R^{125b}$ described above.)

($R^{124b}$)

Examples of the divalent aliphatic hydrocarbon group of at least 1 but not more than 10 carbon atoms for $R^{124b}$ include a methylene group, ethylene group, trimethylene group, tetramethylene group, pentamethylene group and hexamethylene group. Examples of the divalent aromatic hydrocarbon group of at least 6 but not more than 10 carbon atoms for $R^{124b}$ include a phenylene group and a naphthalene-diyl group.

($R^{125b}$ and $R^{130b}$)

Each of $R^{125b}$ and $R^{130b}$ independently represents a polyalkylene chain of at least 1 but not more than 5 carbon atoms. In other words, $R^{125b}$ and $R^{130b}$ are divalent groups represented by general formula (V) shown below.

—(CH$_2$)$_{n51}$— (V)

In general formula (V), n51 represents an integer of at least 1 but not more than 5.

Examples of the alkylene group of at least 1 but not more than 5 carbon atoms include a methylene group, ethylene group, trimethylene group, tetramethylene group and pentamethylene group.

Specific preferred examples of the compound (I-B)-2a, the compound (I-B)-2b, the compound (I-B)-2c and the compound (I-B)-2d include aliphatic diisocyanates of at least 4 but not more than 30 carbon atoms, alicyclic diisocyanates of at least 8 but not more than 30 carbon atoms, and aromatic diisocyanates of at least 8 but not more than 30 carbon atoms. Specific examples of these diisocyanates include the same compounds as those exemplified below in the section entitled "Carbodiimide Compounds".

Further, preferred examples of the compound (I-B)-2c include compounds represented by formula (I-B)-2c-1 shown below (hereafter sometimes abbreviated as "compound (I-B)-2c-1").

These compounds are merely examples of preferred compounds (I-B), and preferred examples of the compound (I-B) are not limited to these compounds.

[Chemical formula 46]

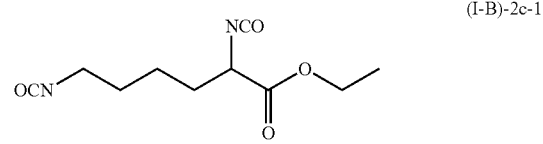

(I-B)-2c-1

3. Trifunctional Isocyanate Compounds

In the compound (I-B), in the case of trifunctional isocyanate compounds in which n31 is 3 (namely, compounds having three isocyanate groups in each molecule), preferred examples of the compound (I-B) include compounds represented by general formula (I-B)-3a shown below (hereafter sometimes referred to as "compound (I-B)-3a"), compounds represented by general formula (I-B)-3b shown below (hereafter sometimes referred to as "compound (I-B)-3b"), and compounds represented by general formula (I-B)-3c shown below (hereafter sometimes referred to as "compound (I-B)-3c").

These compounds are merely examples of preferred compounds (I-B), and preferred examples of the compound (I-B) are not limited to these compounds.

[Chemical formula 47]

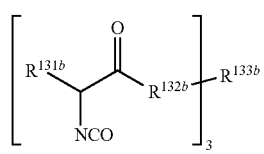

(I-B)-3a

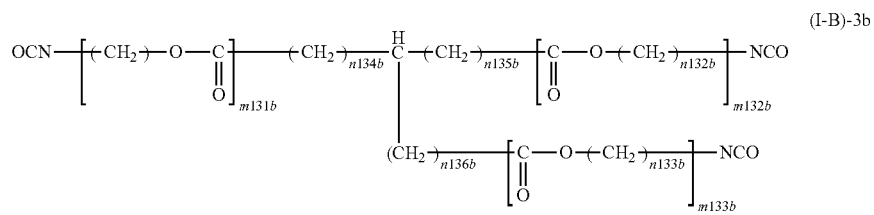

(I-B)-3b

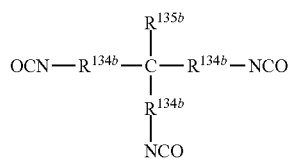

(I-B)-3c (In general formula (I-B)-3a, $R^{111b}$ is the same as $R^{112b}$ described above. $R^{132b}$ is the same as $R^{113b}$ described above. $R^{133b}$ represents a trivalent aliphatic hydrocarbon group of at least 1 but not more than 10 carbon atoms or a trivalent aromatic hydrocarbon group of at least 6 but not more than 10 carbon atoms.

In general formula (I-B)-3b, each of n131b, n132b and n133b independently represents an integer of at least 1 but not more than 4. Further, each of n134b, n135b and n136b independently represents an integer of at least 0 but not more than 5. Moreover, each of m131b, m132b and m133b independently represents 0 or 1.

In general formula (I-B)-3c, each of the plurality of $R^{134b}$ groups independently represents a single bond or a divalent hydrocarbon group of at least 1 but not more than 20 carbon atoms that may contain at least one group selected from the group consisting of an ester group and an ether group. $R^{135b}$ represents a hydrogen atom or a monovalent hydrocarbon group of at least 1 but not more than 12 carbon atoms. The divalent hydrocarbon group of at least 1 but not more than 20 carbon atoms and the hydrocarbon group of at least 1 but not more than 12 carbon atoms may each have a substituent.)

($R^{133b}$)

$R^{133b}$ represents a trivalent aliphatic hydrocarbon group of at least 1 but not more than 10 carbon atoms or a trivalent aromatic hydrocarbon group of at least 6 but not more than 10 carbon atoms.

Examples of the trivalent aliphatic hydrocarbon group of at least 1 but not more than 10 carbon atoms for $R^{133b}$ include a methane-triyl group, ethanetriyl group and propa-netriyl group. Examples of the trivalent aromatic hydrocarbon group of at least 6 but not more than 10 carbon atoms for $R^{133b}$ include a benzenetriyl group and a naphthalenetriyl group.

($R^{134b}$)

Examples of preferred $R^{134b}$ groups include divalent aliphatic hydrocarbon groups of at least 1 but not more than 20 carbon atoms, divalent aromatic hydrocarbon groups of at least 6 but not more than 20 carbon atoms, divalent groups of at least 2 but not more than 20 carbon atoms containing an aliphatic hydrocarbon group and another aliphatic hydrocarbon group bonded together via an ester linkage, divalent groups of at least 2 but not more than 20 carbon atoms containing an aliphatic hydrocarbon group and another aliphatic hydrocarbon group bonded together via an ether linkage, divalent groups of at least 7 but not more than 20 carbon atoms containing an aliphatic hydrocarbon group and an aromatic hydrocarbon group bonded together via an ester linkage, divalent groups of at least 7 but not more than 20 carbon atoms containing an aliphatic hydrocarbon group and an aromatic hydrocarbon group bonded together via an ether linkage, divalent groups of at least 14 but not more than 20 carbon atoms containing an aromatic hydrocarbon group and another aromatic hydrocarbon group bonded together via an ester linkage, and divalent groups of at least 14 but not more than 20 carbon atoms containing an aromatic hydrocarbon group and another aromatic hydrocarbon group bonded together via an ether linkage.

($R^{135b}$)

$R^{135b}$ is preferably an aliphatic hydrocarbon group of at least 1 but not more than 10 carbon atoms or an aromatic hydrocarbon group of at least 6 but not more than 10 carbon atoms. Examples of the aliphatic hydrocarbon group of at least 1 but not more than 10 carbon atoms and the aromatic hydrocarbon group of at least 6 but not more than 10 carbon atoms for $R^{135b}$ include the same groups as those exemplified above for $R^{112b}$ and $R^{114b}$.

Preferred examples of the compound (I-B)-3b include compounds represented by general formula (I-B)-3b1 shown below (hereafter sometimes referred to as "compound (I-B)-3b1").

[Chemical formula 48]

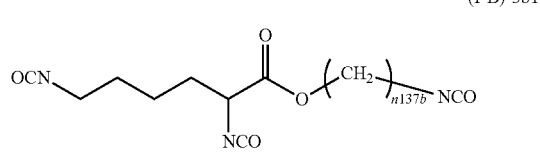

(I-B)-3b1

(In general formula (I-B)-3b1, n137b represents an integer of at least 2 but not more than 4.)

Preferred examples of the compound (I-B)-3b1 include lysine triisocyanate (hereafter sometimes abbreviated as LTI).

Preferred examples of the compound (I-B)-3c include nonane triisocyanate (hereafter sometimes abbreviated as NTI).

These compounds are merely examples of preferred compounds (I-B), and preferred examples of the compound (I-B) are not limited to these compounds.

Among the various possibilities, the compound (I-B) is preferably a trifunctional isocyanate compound, and more preferably the compound (I-B)-3c.

More specific examples of preferred forms of the compound (1) include compounds having a group represented by general formula (1β) shown below, compounds having a group represented by general formula (1γ) shown below, compounds having a group represented by general formula (1δ) shown below, compounds having a group represented by general formula (1ε) shown below, compounds having a

[Chemical formula 50]

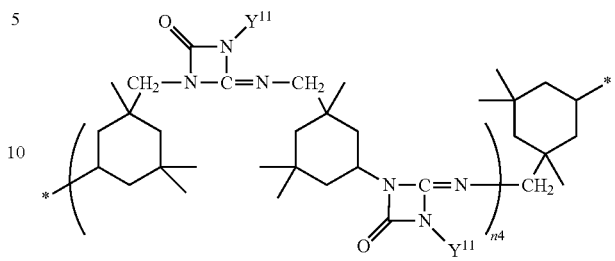

(1γ)

In general formula (1γ), n4 represents an integer of at least 1 but not more than 20. $Y^{11}$ is the same as $Y^{11}$ described above. Each asterisk represents a bonding site with a terminal group.

[Chemical formula 51]

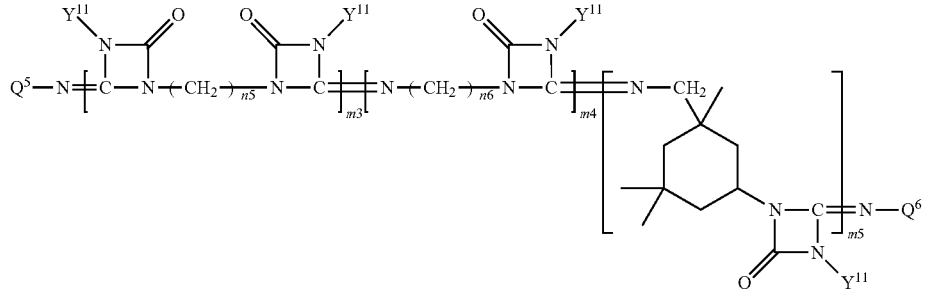

(1δ)

In general formula (1δ), each of n5 and n6 independently represents an integer of at least 1 but not more than 12. Further, m3, m4 and m5 each represent an integer of at least 0 but not more than 20, but are not simultaneously 0. The total of m3+m4+m5 is at least 1 but not more than 20. The values of m3, m4 and m5 represent the numbers of the respective unit components, which may be included in random or block arrangements, with the total number of each unit being represented by m3, m4 and m5 respectively. $Y^{11}$ is the same as $Y^{11}$ described above. Each of $Q^5$ and $Q^6$ represents a monovalent organic group, and is a group represented by formula (1δ-1) shown below or a group represented by formula (1δ-2) shown below.

group represented by general formula (1ζ) shown below, compounds having a group represented by general formula (1η) shown below, compounds having a group represented by general formula (1θ) shown below, compounds having a group represented by general formula (1ι) shown below, and compounds having a group represented by general formula (1κ) shown below.

[Chemical formula 49]

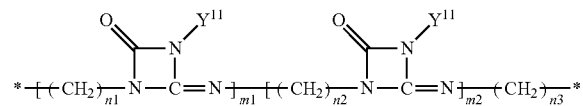

(1β)

In general formula (1β), each of n1, n2 and n3 independently represents an integer of at least 1 but not more than 12. Further, m1 and m2 each independently represent an integer of at least 0 but not more than 10, but are not simultaneously 0. The total of m1+m2 is at least 1 but not more than 20. The values of m1 and m2 represent the numbers of the respective unit components, which may be included in random or block arrangements, with the total number of each unit being represented by m1 and m2 respectively. $Y^{11}$ is the same as $Y^{11}$ described above. Each asterisk represents a bonding site with a terminal group.

[Chemical formula 52]

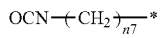

(1δ-1)

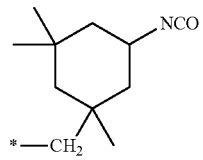

(1δ-2)

In the formulas, n7 represents an integer of at least 1 but not more than 12. Each asterisk represents a bonding site.

[Chemical formula 53]

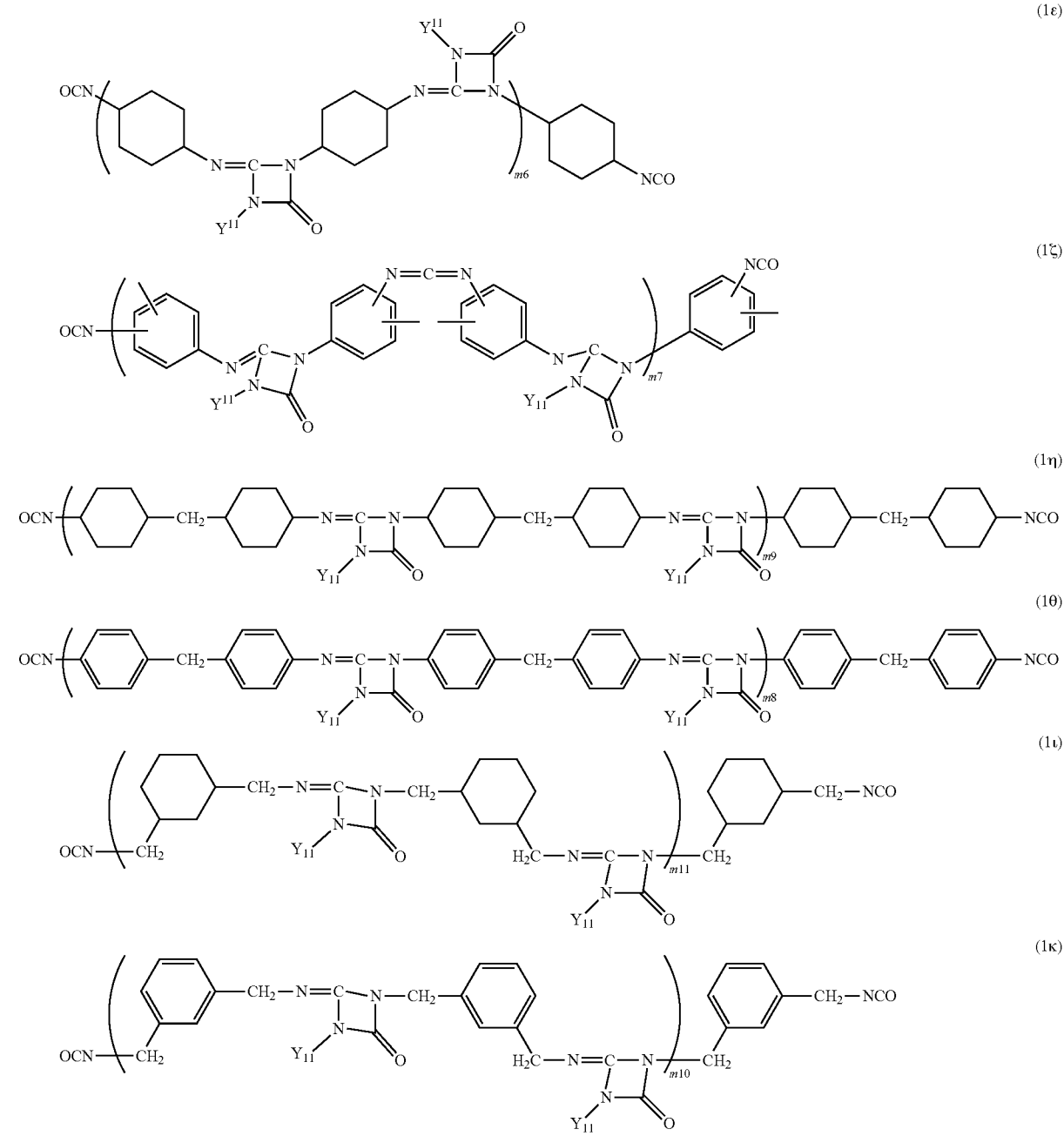

In general formulas (1 ε) to (1κ), each of m6, m7, m8, m9, m10 and m11 independently represents an integer of at least 1 but not more than 12. $Y^{11}$ is the same as $Y^{11}$ described above.

<<Method for Producing Uretonimine Group-Containing Compound>>

The compound of an embodiment of the present invention is produced by reacting a carbodiimide group derived from at least one diisocyanate among an aliphatic diisocyanate and an aromatic diisocyanate, and an isocyanate group derived from an isocyanate compound.

Specifically, the compound is produced by reacting a carbodiimide compound represented by general formula (2) shown below (hereafter sometimes referred to as "carbodiimide compound (2)") and an isocyanate compound represented by general formula (3) shown below (hereafter sometimes referred to as "isocyanate compound (3)").

[Chemical formula 54]

$$Q^{21}\text{-}X^{21}\text{—}Y^{21}\text{-}Q^{22} \quad (2)$$

(In general formula (2), $X^{21}$ is a group containing at least one group represented by general formula (2-1) shown below. In those cases where $X^{21}$ contains two or more groups represented by general formula (2-1) shown below, the plurality of groups represented by general formula (2-1) shown below may be the same or different. $Y^{21}$ is a group represented by general formula (1-2) shown below. Each of $Q^{21}$ and $Q^{22}$ independently represents a hydrogen atom, a group represented by general formula (1-3) shown below, a group represented by general formula (1-4) shown below, or a group represented by general formula (1-5) shown below.)

[Chemical formula 55]

$$*-X^{22}-N=C=N-* \qquad (2\text{-}1)$$

(In general formula (2-1), $X^{22}$ represents a residue obtained by removing two isocyanate groups from at least one diisocyanate among an aliphatic diisocyanate and an aromatic diisocyanate.)

[Chemical formula 56]

$$*-Y^{2}-* \qquad (1\text{-}2)$$

$$*-NCO \qquad (1\text{-}3)$$

$$*-Z^{2}-Q^{3} \qquad (1\text{-}4)$$

$$(1\text{-}5)$$

(In general formula (1-2) to general formula (1-5), each asterisk represents a bonding site. $Y^2$ represents a residue obtained by removing two isocyanate groups from at least one diisocyanate among an aliphatic diisocyanate and an aromatic diisocyanate. $Q^3$ represents a hydrogen atom or a monovalent organic group of at least 1 but not more than 15 carbon atoms. $Z^2$ is a group represented by general formula (1-a) shown below, a group represented by general formula (1-c) shown below, or a group represented by general formula (1-d) shown below. $R^1$ represents a residue obtained by removing the hydrogen atom from a terminal hydroxyl group of a monofunctional polyalkylene oxide polyether alcohol.)

[Chemical formula 57]

$$*-N=C=N-* \qquad (1\text{-}a)$$

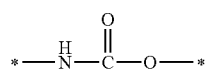
$$(1\text{-}c)$$

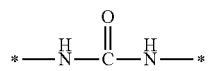
$$(1\text{-}d)$$

(In general formula (1-a), general formula (1-c) and general formula (1-d), each asterisk represents a bonding site.)

[Chemical formula 58]

$$R^3-NCO \qquad (3)$$

(In general formula (3), $R^3$ represents a residue obtained by removing one isocyanate group from an isocyanate compound.)

Details of the carbodiimide compound (2) are described below. Further, examples of the isocyanate compound (3) include the same compounds as the isocyanate compounds (the compound (I-B)) exemplified above in relation to $Y^{11}$.

<Production Method 1 for Compound (1α)>

A method for producing the above compound (1α) is described below as an example of a specific method for producing an uretonimine group-containing compound according to an embodiment of the present invention.

The compound (1α) can be produced, for example, using a production method having a step of reacting a carbodiimide compound and an isocyanate compound to obtain a compound having an uretonimine group (hereafter sometimes referred to as the "uretonimine group-containing compound production step"), and a step of reacting the obtained uretonimine group-containing compound and a monofunctional polyalkylene oxide poly ether alcohol to obtain the compound (1α) (hereafter sometimes referred to as the "compound (1α) production step").

[Uretonimine Group-Containing Compound Production Step]

In the uretonimine group-containing compound production step, a carbodiimide compound and an isocyanate compound are reacted to obtain a compound having an uretonimine group. The reaction for obtaining the compound having an uretonimine group is a conventionally known reaction.

The reaction temperature may be set, for example, to at least 15° C. but not more than 70° C., or may be set to at least 20° C. but not more than 60° C.

The reaction may be performed in the presence of a solvent or in the absence of a solvent. There are no particular limitations on the solvent, and examples include hydrocarbons, ethers, compounds having an amide linkage, sulfoxides, and halogenated hydrocarbons. Examples of the hydrocarbons include benzene, toluene and xylene. Examples of the ethers include tetrahydrofuran (hereafter sometimes abbreviated as THF) and diethyl ether. Examples of the compounds having an amide linkage include N,N-dimethylformamide. Examples of the sulfoxides include dimethylsulfoxide. Examples of the halogenated hydrocarbons include methylene chloride and chlorobenzene. A single solvent may be used alone, or a combination of two or more solvents may be used, and in the case where a combination of two or more solvents is used, the combination and proportions of the solvents may be selected as appropriate.

The amount used of the isocyanate compound may be set to an amount that yields a molar amount of isocyanate groups of the isocyanate compound of at least 0.8-fold but not more than 1.5-fold relative to the molar amount of carbodiimide groups of the carbodiimide compound.

In the uretonimine group-containing compound production step, following completion of the reaction, a conventional technique may be used to conduct a post-treatment as necessary, and the uretonimine group-containing compound may then be collected. In other words, if necessary, a single post-treatment or a combination of two or more post-treatments such as filtration, washing, extraction, pH adjustment, dewatering or concentration may be conducted, and the uretonimine group-containing compound may then be collected by concentration, crystallization, reprecipitation or column chromatography or the like. Further, if necessary, the collected uretonimine group-containing compound may be further purified by using one operation or a combination of two or more operations such as crystallization, reprecipitation, column chromatography, extraction, and stirred washing of the crystals in a solvent.

In the uretonimine group-containing compound production step, following completion of the reaction, the uretonimine group-containing compound may be simply used in the next step without undergoing collection, but in terms of improving the yield of the compound (1α) that represents the target product, the uretonimine group-containing compound is preferably collected using the methods described above.

(Carbodiimide Compound)

Examples of the carbodiimide compound used in the production of the compound of an embodiment of the present invention include compounds represented by general formula (I-A) shown below.

[Chemical formula 59]

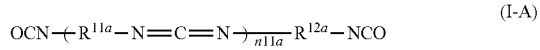

(I-A)

(In general formula (I-A), $R^{11a}$ and $R^{12a}$ are the same as $R^{11}$ and $R^{12}$ respectively described above. Further, n11a is the same as n11 described above.)

The carbodiimide compound may be produced using conventional methods. For example, the carbodiimide compound may be produced by heating a diisocyanate, either in the presence of a solvent or in the absence of a solvent, at a temperature of at least 100° C. but not more than 200° C., using a phospholene oxide or the like as a catalyst. Examples of the solvent include the same solvents as those exemplified above in the section entitled "Uretonimine Group-Containing Compound Production Step". Examples of the catalyst include 1-phenyl-2-phospholene-1-oxide and 3-methyl-1-phenyl-2-phospholene-1-oxide.

Following completion of the reaction, the carbodiimide compound produced in this manner may be collected using the same methods as those described above for the uretonimine group-containing compound production step, and the collected carbodiimide compound may then be further purified using the same methods as those described above.

Diisocyanates

Examples of the diisocyanate used in the production of the carbodiimide compound include aliphatic diisocyanates, alicyclic diisocyanates and aromatic diisocyanates.

Examples of the aliphatic diisocyanates include 1,4-tetramethylene diisocyanate, 1,5-pentamethylene diisocyanate, HDI, 2,2,4-trimethyl-1,6-hexamethylene diisocyanate, and lysine diisocyanate.

Examples of the alicyclic diisocyanates include IPDI, 4,4'-methylenebiscyclohexyl diisocyanate (hereafter sometimes abbreviated as "hydrogenated MDI"), and dimethylcyclohexane diisocyanate (hereafter sometimes abbreviated as "hydrogenated XDI").

Examples of the aromatic diisocyanates include 2,4-tolylene diisocyanate, 2,6-tolylene diisocyanate and mixtures thereof (hereafter sometimes abbreviated as TDIs), diphenylmethane-4,4'-diisocyanate (hereafter sometimes abbreviated as MDI), naphthalene-1,5-diisocyanate hereafter sometimes abbreviated as NDI), 3,3-dimethyl-4,4-diphenylene diisocyanate (hereafter sometimes abbreviated as TODI), crude TDIs, polymethylene polyphenyl diisocyanate, crude MDI, phenylene diisocyanate, xylylene diisocyanate (hereafter sometimes abbreviated as XDI), and tetramethylxylylene diisocyanate (hereafter sometimes abbreviated as TMXDI).

Among these compounds, the diisocyanate is preferably an alicyclic diisocyanate or aromatic diisocyanate, and is more preferably IPDI, hydrogenated MDI, MDI or TMXDI.

Polyisocyanates

Examples of polyisocyanates that may be used in the production of the carbodiimide compound include the same compounds as those exemplified above in the section entitled "$R^{11}$ and $R^{12}$". Among these compounds, polyisocyanates having an isocyanurate group are preferred as the polyisocyanate.

In those cases where a polyisocyanate is used in the production of the carbodiimide compound, the polyisocyanate is preferably used in combination with a diisocyanate. In such cases, the amount used of the polyisocyanate, expressed as a mass ratio relative to the diisocyanate (polyisocyanate/diisocyanate), may be set to a ratio of at least 20/80 but not more than 1/99, or a ratio of at least 15/85 but not more than 5/95.

(Isocyanate Compound)

Examples of the isocyanate compound include the same compounds as those exemplified above in the description of $Y^{11}$ in general formula (1a). Examples of preferred isocyanate compounds include cyclohexyl isocyanate, phenyl isocyanate, the compound (I-B)-1b-1, the compound (I-B)-1b-2, the compound (I-B)-1b-3, the compound (I-B)-1b-4, pentamethylene diisocyanate, HDI, the compound (I-B)-2c-1, NTI, LTI, and HDI-based polyisocyanates.

[Compound (1α) Production Step]

In the compound (1α) production step, the uretonimine group-containing compound and a monofunctional polyalkylene oxide poly ether alcohol are reacted together to obtain the compound (1α).

Specifically, a terminal isocyanate group of the uretonimine group-containing compound and the terminal hydroxyl group of the monofunctional polyalkylene oxide polyether alcohol are reacted, thereby introducing the residue obtained by removing the hydrogen atom from the terminal hydroxyl group of the monofunctional polyalkylene oxide poly ether alcohol at the terminal of the uretonimine group-containing compound to produce the compound (1α).

The reaction temperature may be set, for example, to a temperature of at least 80° C. but not more than 200° C., or a temperature of at least 100° C. but not more than 150° C.

The reaction may be conducted in the presence of a solvent or in the absence of a solvent. Examples of the solvent include the same solvents as those exemplified above in the section entitled "Uretonimine Group-Containing Compound Production Step".

Examples of the monofunctional polyalkylene oxide poly ether alcohol include the same compounds as those exemplified above in the description of the compound (1α). Examples of preferred monofunctional polyalkylene oxide poly ether alcohols include polyethylene glycol monoalkyl ethers, polypropylene glycol monoalkyl ethers, and copolymers of these compounds.

In the compound (1α) production step, following completion of the reaction, the compound (1α) may be collected using the same methods as those described above for the uretonimine group-containing compound production step, and the collected compound (1α) may also be further purified using the same methods as those described above.

The structures of the compound (1α), the uretonimine group-containing compound, the carbodiimide compound and the isocyanate compound and the like can each be confirmed using conventional techniques such as nuclear magnetic resonance (NMR) spectroscopy methods, mass spectrometry methods (MS) and infrared spectroscopy methods (IR).

<Production Method 2 for Compound (1α)>

Furthermore, the compound (1α) can also be produced using a production method having a step of reacting a carbodiimide compound and a monofunctional polyalkylene oxide poly ether alcohol to obtain a hydrophilic carbodiimide compound (hereafter sometimes referred to as the "hydrophilic carbodiimide compound production step"), and a step of reacting the obtained hydrophilic carbodiimide compound and an isocyanate compound to obtain the compound (1α) (hereafter sometimes referred to as the "compound (1α) production step").

Examples of the carbodiimide compound, the monofunctional polyalkylene oxide poly ether alcohol and the isocyanate compound used in the production of the compound (1α) include the same compounds as those exemplified above in the section entitled "Production Method 1 for Compound (1α)".

[Hydrophilic Carbodiimide Compound Production Step]

In the hydrophilic carbodiimide compound production step, the carbodiimide compound and the monofunctional polyalkylene oxide poly ether alcohol are reacted to obtain a hydrophilic carbodiimide compound. Specifically, a terminal isocyanate group of the carbodiimide compound and the terminal hydroxyl group of the monofunctional polyalkylene oxide polyether alcohol are reacted, thereby introducing the residue obtained by removing the hydrogen atom from the terminal hydroxyl group of the monofunctional polyalkylene oxide poly ether alcohol at the terminal of the carbodiimide compound to produce the hydrophilic carbodiimide compound. The reaction for obtaining the hydrophilic carbodiimide compound is a conventionally known reaction.

The reaction temperature may be set, for example, to a temperature of at least 80° C. but not more than 200° C., or a temperature of at least 100° C. but not more than 180° C.

Examples of the monofunctional polyalkylene oxide poly ether alcohol include the same compounds as those exemplified above in the description of the compound (1α). Examples of preferred monofunctional polyalkylene oxide poly ether alcohols include polyethylene glycol monoalkyl ethers, polypropylene glycol monoalkyl ethers, and copolymers of these compounds.

The reaction may be conducted in the presence of a solvent or in the absence of a solvent. Examples of the solvent include, but are not limited to, hydrocarbons, ethers, compounds having an amide linkage, sulfoxides, and halogenated hydrocarbons. Examples of the hydrocarbons include benzene, toluene and xylene. Examples of the ethers include tetrahydrofuran (hereafter sometimes abbreviated as THF) and diethyl ether. Examples of the compounds having an amide linkage include N,N-dimethylformamide. Examples of the sulfoxides include dimethylsulfoxide. Examples of the halogenated hydrocarbons include methylene chloride and chlorobenzene. A single solvent may be used alone, or a combination of two or more solvents may be used, and in the case where a combination of two or more solvents is used, the combination and proportions of the solvents may be selected as appropriate.

In the hydrophilic carbodiimide compound production step, following completion of the reaction, a conventional technique may be used to conduct a post-treatment as necessary, and the hydrophilic carbodiimide compound may then be collected. In other words, if necessary, a single post-treatment or a combination of two or more post-treatments such as filtration, washing, extraction, pH adjustment, dewatering or concentration may be conducted, and the hydrophilic carbodiimide compound may then be collected by concentration, crystallization, reprecipitation or column chromatography or the like. Further, if necessary, the collected hydrophilic carbodiimide compound may be further purified by using one operation or a combination of two or more operations such as crystallization, reprecipitation, column chromatography, extraction, and stirred washing of the crystals in a solvent.

In the hydrophilic carbodiimide compound production step, following completion of the reaction, the hydrophilic carbodiimide compound may be simply used in the next step without undergoing collection, but in terms of improving the yield of the compound (1α) that represents the target product, the hydrophilic carbodiimide compound is preferably collected using the methods described above.

[Compound (1α) Production Step]

In the compound (1α) production step, the obtained hydrophilic carbodiimide compound and an isocyanate compound are reacted together to obtain the compound (1a).

Specifically, the carbodiimide group of the carbodiimide compound and a terminal isocyanate group of the isocyanate compound are reacted, thereby forming an uretonimine group to produce the compound (1α). The reaction for obtaining the compound (1α) is a conventionally known reaction.

The reaction temperature may be set, for example, to a temperature of at least 50° C. but not more than 100° C., or a temperature of at least 60° C. but not more than 90° C.

The reaction may be conducted in the presence of a solvent or in the absence of a solvent. Examples of the solvent include the same solvents as those exemplified above in the section entitled "Hydrophilic Carbodiimide Compound Production Step".

In the compound (1α) production step, following completion of the reaction, the compound (1α) may be collected using the same methods as those described above for the hydrophilic carbodiimide compound production step, and the collected compound (1α) may also be further purified using the same methods as those described above.

The structures of the compound (1α), the hydrophilic carbodiimide compound, the carbodiimide compound, and the isocyanate compound and the like can each be confirmed using conventional techniques such as nuclear magnetic resonance (NMR) spectroscopy methods, mass spectrometry methods (MS) and infrared spectroscopy methods (IR).

<<Carbodiimide Compound>>

The carbodiimide compound of an embodiment of the present invention is a compound represented by general formula (2) shown below.

[Chemical formula 60]

$$Q^{21}\text{-}X^{21}\text{—}Y^{21}\text{-}Q^{22} \qquad (2)$$

(In general formula (2), $X^{21}$ is a group containing at least one group represented by general formula (2-1) shown below. In those cases where $X^{21}$ contains two or more groups represented by general formula (2-1) shown below, the plurality of groups represented by general formula (2-1) shown below may be the same or different. $Y^{21}$ is a group represented by general formula (1-2) shown below. Each of $Q^{21}$ and $Q^{22}$ independently represents a hydrogen atom, a group represented by general formula (1-3) shown below, a group represented by general formula (1-4) shown below, or a group represented by general formula (1-5) shown below.)

[Chemical formula 61]

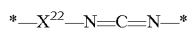

$$\text{*—}X^{22}\text{—}N\!=\!C\!=\!N\text{—*} \qquad (2\text{-}1)$$

(In general formula (2-1), $X^{22}$ represents a residue obtained by removing two isocyanate groups from at least one diisocyanate among an aliphatic diisocyanate and an aromatic diisocyanate.)

[Chemical formula 62]

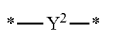 (1-2)

 (1-3)

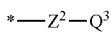 (1-4)

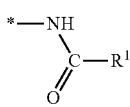 (1-5)

(In general formula (1-2) to general formula (1-5), each asterisk represents a bonding site. $Y^2$ represents a residue obtained by removing two isocyanate groups from at least one diisocyanate among an aliphatic diisocyanate and an aromatic diisocyanate. $Q^3$ represents a hydrogen atom or a monovalent organic group of at least 1 but not more than 15 carbon atoms. $Z^2$ is a group represented by general formula (1-a) shown below, a group represented by general formula (1-c) shown below, or a group represented by general formula (1-d) shown below. $R^1$ represents a residue obtained by removing the hydrogen atom from a terminal hydroxyl group of a monofunctional polyalkylene oxide polyether alcohol.)

[Chemical formula 63]

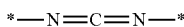 (1-a)

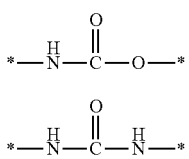 (1-c)

(1-d)

(In general formula (1-a), general formula (1-c) and general formula (1-d), each asterisk represents a bonding site.)

Each of $X^{22}$ and $Y^2$ represents a residue obtained by removing two isocyanate groups from at least one diisocyanate among an aliphatic diisocyanate and an aromatic diisocyanate. An aliphatic hydrocarbon group of at least 1 but not more than 22 carbon atoms or an aromatic hydrocarbon group of at least 6 but not more than 22 carbon atoms is preferred as $X^{22}$ and $Y^2$. Specific examples include the same groups as those exemplified above in relation to $X^2$ and $Y^2$.

Each of these types of $X^{22}$ and $Y^2$ groups is preferably a group represented by formula (III-1) shown above, a group represented by formula (III-2) shown above, a group represented by formula (III-3) shown above, a group represented by formula (III-5) shown above, a group represented by formula (III-6) shown above, a group represented by formula (VI-1) shown above, a group represented by formula (VI-2) shown above, or a group represented by formula (VI-3) shown above.

In other words, $X^{21}$ is preferably a group containing one or more of at least one type of group selected from the group consisting of groups represented by general formula (III-1-2) shown below, groups represented by general formula (III-2-3) shown below, groups represented by general formula (III-2-4) shown below, groups represented by general formula (III-3-2) shown below, groups represented by general formula (III-5-2) shown below, groups represented by general formula (III-6-2) shown below, groups represented by general formula (VI-1-2) shown below, groups represented by general formula (VI-2-2) shown below, and groups represented by general formula (VI-3-2) shown below.

[Chemical formula 64]

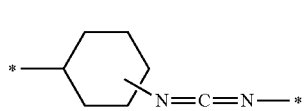 (III-1-2)

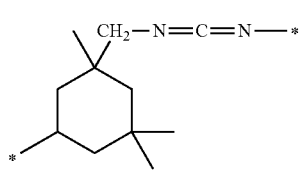 (III-2-3)

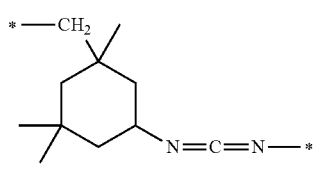 (III-2-4)

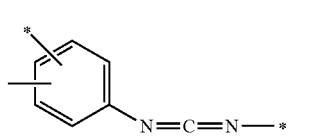 (III-3-2)

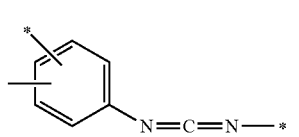 (III-5-2)

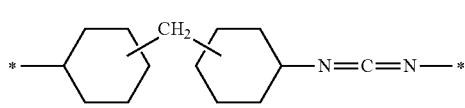 (III-6-2)

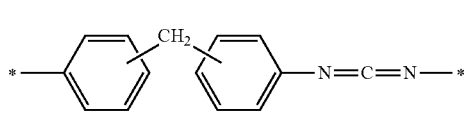 (VI-1-2)

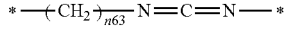 (VI-2-2)

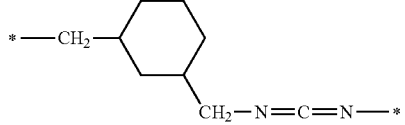 (VI-3-2)

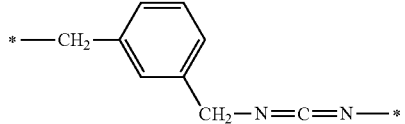

(In the formulas, each asterisk represents a bonding site. Further, n63 represents an integer of at least 1 but not more than 10.)

Furthermore, $Y^{21}$ is preferably a group represented by formula (III-1) shown above, a group represented by formula (III-2) shown above, a group represented by formula (III-3) shown above, a group represented by formula (III-5) shown above, a group represented by formula (III-6) shown above, a group represented by formula (VI-1) shown above, a group represented by formula (VI-2) shown above, or a group represented by formula (VI-3) shown above.

<Preferred Forms of Compound (2)>

Preferred examples of the compound (2) include compounds represented by general formula (2a) shown below (hereafter sometimes referred to as "compound (2a)"). The compound (2a) is a compound having at least one carbodiimide group.

[Chemical formula 65]

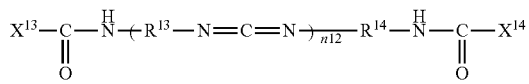

(2α)

(In general formula (2a), n12 represents an integer of at least 1 but not more than 100. Each of $X^{13}$ and $X^{14}$ independently represents a group represented by general formula (II-1) shown below (hereafter sometimes referred to as "group (II-1)") or a group represented by general formula (II-2) shown below (hereafter sometimes referred to as "group (II-2)"). Each of $R^{13}$ and $R^{14}$ independently represents a residue obtained by removing two isocyanate groups from a diisocyanate or a polyisocyanate derived from a diisocyanate.)

[Chemical formula 66]

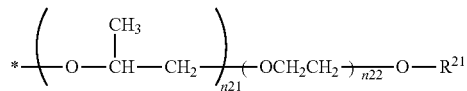

(II-1)

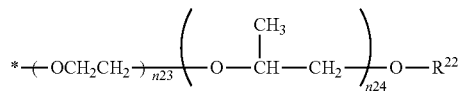

(II-2)

(In general formula (II-1), each of n21 and n22 independently represents an integer of at least 1 but not more than 30. $R^{21}$ represents an alkyl group of at least 1 but not more than 12 carbon atoms that may contain a carbonyl group.

In general formula (II-2), each of n23 and n24 independently represents an integer of at least 1 but not more than 30. $R^{22}$ represents an alkyl group of at least 1 but not more than 12 carbon atoms that may contain a carbonyl group.

Each asterisk represents a bonding site.)

As a result of including the above group (II-1) or the above group (II-2) at the terminals, the compound (2a) exhibits excellent storage stability when used in a resin composition.

The structure of the compound (2a) is described below in further detail.

[n12]

The integer n12 represents the number of repeating carbodiimide groups, and is an integer of at least 1 but not more than 100.

[$X^{13}$ and $X^{14}$]

Each of $X^{13}$ and $X^{14}$ independently represents the above group (II-1) or the above group (II-2). $X^{13}$ and $X^{14}$ may be the same or different, but are preferably the same in terms of ease of production.

The compound (2a) has a structure in which the main skeleton having a hydrophobic carbodiimide group, a weakly hydrophilic propylene oxide repeating unit, and a strongly hydrophilic ethylene oxide repeating unit are bonded in sequence from the center of the molecule toward the terminals, and this enables more stable dispersion in water, and enables the penetration of carboxylic acids and alcohols into the carbodiimide group to be controlled more effectively in water-based solvents. Further, in the group (II-1) or the group (II-2), the ethylene oxide repeating units and the propylene oxide repeating units may be formed by block polymerization or random polymerization.

(n21, n22, n23 and n24)

Each of n21 and n24 independently represents a number of propylene oxide repeating units, whereas each of n22 and n23 independently represents a number of ethylene oxide repeating units. Each of n21, n22, n23 and n24 independently represents at least 1 but not more than 30, preferably at least 1 but not more than 20, more preferably at least 2 but not more than 15, and even more preferably at least 5 but not more than 10. By ensuring that n21, n22, n23 and n24 fall within the above range, the penetration of carboxylic acids and alcohols into the carbodiimide group can be controlled more effectively in water-based solvents.

Further, the ratio of n21 relative to n22 (n21/n22) can be set, for example, to at least 0.8 but not more than 1.2, but is preferably 1.0.

Furthermore, the ratio of n24 relative to n23 (n24/n23) can be set, for example, to at least 0.8 but not more than 1.2, but is preferably 1.0.

By ensuring that the ratios n21/n22 and n24/n23 fall within the above range, the penetration of carboxylic acids and alcohols into the carbodiimide group can be controlled more effectively in water-based solvents.

($R^{21}$ and $R^{22}$)

The alkyl groups for $R^{21}$ and $R^{22}$ may be chain-like or cyclic. The chain-like alkyl group may be either linear or branched. Examples of linear alkyl groups include a methyl group, ethyl group, n-propyl group, n-butyl group, n-pentyl group, n-hexyl group, n-heptyl group, n-octyl group, n-nonyl group, n-decyl group, n-undecyl group and n-dodecyl group. Examples of branched alkyl groups include an isopropyl group, isobutyl group, sec-butyl group, tert-butyl group, isopentyl group and isohexyl group. Examples of cyclic alkyl groups include a cyclopropyl group, cyclobutyl group, cyclopentyl group and cyclohexyl group.

Examples of the alkyl group that may have a carbonyl group for $R^{21}$ and $R^{22}$ include groups represented by general formula (IIa) shown below (hereafter sometimes referred to as "group (IIa)").

[Chemical formula 67]

$$*-C(=O)-R^{23}$$ (IIa)

(In general formula (IIa), $R^{23}$ represents an alkyl group of at least 1 but not more than 11 carbon atoms. The asterisk represents a bonding site.

Examples of the alkyl group for $R^{23}$ include alkyl groups of at least 1 but not more than 11 carbon atoms among those groups exemplified above for $R^{21}$ and $R^{22}$.

Among the various possibilities, $R^{23}$ is preferably an alkyl group of at least 1 but not more than 8 carbon atoms, more preferably a chain-like alkyl group of at least 1 but not more than 6 carbon atoms, and even more preferably a linear alkyl group of at least 1 but not more than 4 carbon atoms.

More preferred $X^{11}$ and $X^{12}$ groups include groups represented by general formula (II-1-1) shown below (hereafter sometimes referred to as "group (II-1-1)"), groups represented by general formula (II-1-2) shown below (hereafter sometimes referred to as "group (II-1-2)"), groups represented by general formula (II-2-1) shown below (hereafter sometimes referred to as "group (II-2-1)"), and groups represented by general formula (II-2-2) shown below (hereafter sometimes referred to as "group (II-2-2)").

[Chemical formula 68]

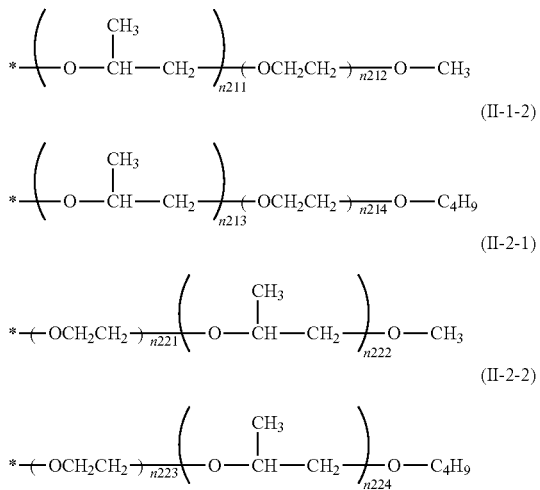

(In general formula (II-1-1), each of n211 and n212 independently represents an integer of at least 1 but not more than 30.

In general formula (II-1-2), each of n213 and n214 independently represents an integer of at least 1 but not more than 30.

In general formula (II-2-1), each of n221 and n222 independently represents an integer of at least 1 but not more than 30.

In general formula (II-2-2), each of n223 and n224 independently represents an integer of at least 1 but not more than 30.

[$R^{13}$ and $R^{14}$]

Each of $R^{13}$ and $R^{14}$ independently represents a residue obtained by removing two isocyanate groups from a diisocyanate or a polyisocyanate derived from a diisocyanate. $R^{13}$ and $R^{14}$ may be the same or different, but are preferably the same in terms of ease of production.

In those cases where $R^{13}$ and $R^{14}$ are residues obtained by removing two isocyanate groups from a diisocyanate, $R^{13}$ and $R^{14}$ are divalent hydrocarbon groups.

The divalent hydrocarbon group is preferably an aliphatic hydrocarbon group of at least 1 but not more than 22 carbon atoms or an aromatic hydrocarbon group of at least 6 but not more than 22 carbon atoms. Specific examples include linear hydrocarbon groups, unsubstituted alicyclic hydrocarbon groups (cycloalkylene groups), alkyl-substituted alicyclic hydrocarbon groups, dialkyl-substituted alicyclic hydrocarbon groups, trialkyl-substituted alicyclic hydrocarbon groups, groups obtained by bonding a linear hydrocarbon group and a trialkyl-substituted alicyclic hydrocarbon group, unsubstituted aromatic hydrocarbon groups, monoalkyl-substituted arylene groups, and dialkyl-substituted arylene groups.

Examples of the linear hydrocarbon groups include a methylene group, ethylene group, trimethylene group, tetramethylene group, pentamethylene group, hexamethylene group and octamethylene group.

Examples of the unsubstituted alicyclic hydrocarbon groups include a cyclopentylene group, cyclohexylene group, cycloheptylene group, cyclooctylene group, and alkylenebis(cyclohexylene) groups. Examples of the alkylenebis(cyclohexylene) groups include a methylenebis(cyclohexylene) group and an ethylenebis(cyclohexylene) group.

Examples of the alkyl-substituted alicyclic hydrocarbon groups include a methylcyclopentylene group, ethylcyclopentylene group, methylcyclohexylene group (each of the isomers), ethylcyclohexylene group (each of the isomers), propylcyclohexylene group (each of the isomers), butylcyclohexylene group (each of the isomers), pentylcyclohexylene group (each of the isomers), and hexylcyclohexylene group (each of the isomers).

Examples of the dialkyl-substituted alicyclic hydrocarbon groups include a dimethylcyclohexylene group (each of the isomers), diethylcyclohexylene group (each of the isomers), and dibutylcyclohexylene group (each of the isomers).

Examples of the trialkyl-substituted alicyclic hydrocarbon groups include a 1,5,5-trimethylcyclohexylene group, 1,5,5-triethylcyclohexylene group, 1,5,5-tripropylcyclohexylene group (each of the isomers), and 1,5,5-tributylcyclohexylene group (each of the isomers).

Examples of the groups obtained by bonding a linear hydrocarbon group and a trialkyl-substituted alicyclic hydrocarbon group include groups represented by formula (III-2) shown below (hereafter sometimes referred to as "group (III-2)").

[Chemical formula 69]

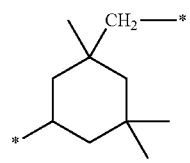

Examples of the unsubstituted aromatic hydrocarbon groups include a phenylene group and diphenylalkane-diyl groups.

Examples of the monoalkyl-substituted arylene groups include a toluene-diyl group, ethylphenylene group, and propylphenylene group.

Examples of the dialkyl-substituted arylene groups include a xylene-diyl group, diethylphenylene group, dipropylphenylene group, and tetramethylxylylene group.

Among the various possibilities, each of $R^{13}$ and $R^{14}$ is preferably an alkylenebis(cyclohexylene) group, the group (III-2), diphenylalkane-diyl group, toluene-diyl group, tetramethylxylylene group, or a group represented by general formula (VI) shown below (hereafter sometimes referred to as "group (VI)"), is more preferably a group represented by formula (III-1) shown below (hereafter sometimes referred to a "group (III-1)"), the group (III-2), a group represented by formula (III-3) shown below (hereafter sometimes referred to a "group (III-3)"), a group represented by formula (III-4) shown below (hereafter sometimes referred to a "group (III-4)"), a group represented by formula (III-5) shown below (hereafter sometimes referred to a "group (III-5)"), a group represented by formula (III-6)

shown below (hereafter sometimes referred to a "group (III-6)"), or the group (VI), and is even more preferably the group (VI).

[Chemical formula 70]

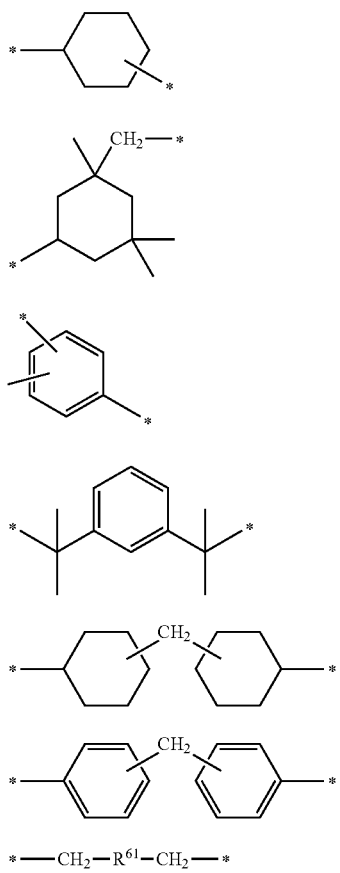

(In the formulas, each asterisk represents a bonding site. In general formula (VI), $R^{61}$ represents an alkylene group of at least 1 but not more than 18 carbon atoms, or an arylene group of at least 6 but not more than 18 carbon atoms.)

($R^{61}$)

Examples of the alkylene group of at least 1 but not more than 18 carbon atoms for $R^{61}$ include groups of at least 1 but not more than 18 carbon atoms among the groups exemplified as the aliphatic hydrocarbon group of at least 1 but not more than 22 carbon atoms in the above description of "$R^{11}$ and $R^{12}$".

Examples of the arylene group of at least 6 but not more than 18 carbon atoms for $R^{61}$ include groups of at least 6 but not more than 18 carbon atoms among the groups exemplified as the aromatic hydrocarbon group of at least 6 but not more than 22 carbon atoms in the above description of "$R^{11}$ and $R^{12}$".

Among the various possibilities, $R^{61}$ is preferably a trimethylene group, tetramethylene group, cyclohexylene group or phenylene group.

Preferred examples of the group (VI) include groups represented by general formula (VI-1) shown below (hereafter sometimes referred to as "group (VI-1)"), groups represented by general formula (VI-2) shown below (hereafter sometimes referred to as "group (VI-2)"), and groups represented by general formula (VI-3) shown below (hereafter sometimes referred to as "group (VI-3)").

[Chemical formula 71]

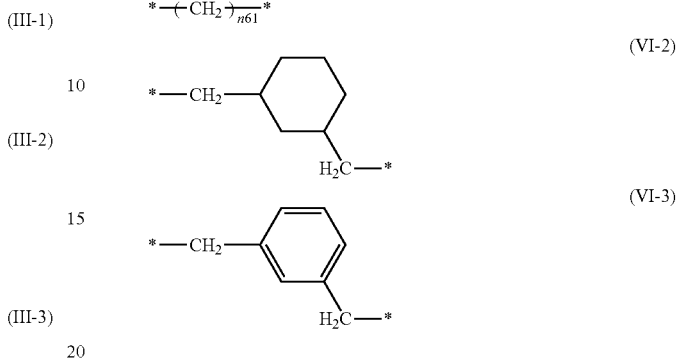

(In the formulas, each asterisk represents a bonding site. In general formula (VI-1), n61 represents an integer of at least 3 but not more than 10.)

Preferred examples of the group (VI-1) include a trimethylene group, tetramethylene group, pentamethylene group and hexamethylene group, and among these, a tetramethylene group, pentamethylene group or hexamethylene group is particularly preferred.

In those cases where $R^{13}$ and $R^{14}$ are residues obtained by removing two isocyanate groups from a polyisocyanate derived from a diisocyanate, the polyisocyanate that gives rise to $R^{13}$ and $R^{14}$ has at least one functional group selected from the group consisting of an isocyanurate group, allophanate group, biuret group, uretdione group, iminooxadiazinedione group and urethane group. Among the various possibilities, the polyisocyanate preferably has an isocyanurate group.

Further, preferred examples of the compound (2) include compounds represented by general formula (2β) shown below (hereafter sometimes referred to as "compound (2β)"). The compound (2β) is a compound having at least one carbodiimide group.

[Chemical formula 72]

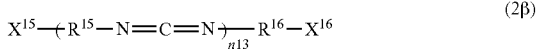

(2β)

(In general formula (2β), n13 represents an integer of at least 1 but not more than 100. Each of $X^{15}$ and $X^{16}$ independently represents a group represented by general formula (VIII) shown below (hereafter sometimes referred to as "group (VIII)"). Each of $R^{15}$ and $R^{16}$ independently represents a residue obtained by removing two isocyanate groups from a diisocyanate or a polyisocyanate derived from a diisocyanate.)

[Chemical formula 73]

(VIII)

(In general formula (VIII), $Y^{81}$ represents a carbodiimide group, a urea group or a urethane group. $R^{81}$ represents a monovalent hydrocarbon group of at least 1 but not more than 12 carbon atoms that may include a carbonyl group or an ester linkage. The asterisk represents a bonding site.)

As a result of including the above group (VIII) at the terminals, the compound (2β) exhibits excellent storage stability, particularly when used in a resin composition containing a hydrophobic solvent.

The structure of the compound (2β) is described below in further detail.

[n13]

The integer n13 represents the number of repeating carbodiimide groups, and is an integer of at least 1 but not more than 100.

[$R^{15}$ and $R^{16}$]

Each of $R^{15}$ and $R^{16}$ independently represents a residue obtained by removing two isocyanate groups from a diisocyanate or a polyisocyanate derived from a diisocyanate. $R^{15}$ and $R^{16}$ may be the same or different, but are preferably the same in terms of ease of production.

In those cases where $R^{15}$ and $R^{16}$ are residues obtained by removing two isocyanate groups from a diisocyanate, $R^{15}$ and $R^{16}$ are divalent hydrocarbon groups.

The divalent hydrocarbon group is preferably an aliphatic hydrocarbon group of at least 1 but not more than 22 carbon atoms or an aromatic hydrocarbon group of at least 6 but not more than 22 carbon atoms. Specific examples include linear hydrocarbon groups, unsubstituted alicyclic hydrocarbon groups (cycloalkylene groups), alkyl-substituted alicyclic hydrocarbon groups, dialkyl-substituted alicyclic hydrocarbon groups, trialkyl-substituted alicyclic hydrocarbon groups, groups obtained by bonding a linear hydrocarbon group and a trialkyl-substituted alicyclic hydrocarbon group, unsubstituted aromatic hydrocarbon groups, monoalkyl-substituted arylene groups, and dialkyl-substituted arylene groups.

Examples of the linear hydrocarbon groups include a methylene group, ethylene group, trimethylene group, tetramethylene group, pentamethylene group, hexamethylene group and octamethylene group.

Examples of the unsubstituted alicyclic hydrocarbon groups include a cyclopentylene group, cyclohexylene group, cycloheptylene group, cyclooctylene group, and alkylenebis(cyclohexylene) groups. Examples of the alkylenebis(cyclohexylene) groups include a methylenebis(cyclohexylene) group and an ethylenebis(cyclohexylene) group.

Examples of the alkyl-substituted alicyclic hydrocarbon groups include a methylcyclopentylene group, ethylcyclopentylene group, methylcyclohexylene group (each of the isomers), ethylcyclohexylene group (each of the isomers), propylcyclohexylene group (each of the isomers), butylcyclohexylene group (each of the isomers), pentylcyclohexylene group (each of the isomers), and hexylcyclohexylene group (each of the isomers).

Examples of the dialkyl-substituted alicyclic hydrocarbon groups include a dimethylcyclohexylene group (each of the isomers), diethylcyclohexylene group (each of the isomers), and dibutylcyclohexylene group (each of the isomers).

Examples of the trialkyl-substituted alicyclic hydrocarbon groups include a 1,5,5-trimethylcyclohexylene group, 1,5,5-triethylcyclohexylene group, 1,5,5-tripropylcyclohexylene group (each of the isomers), and 1,5,5-tributylcyclohexylene group (each of the isomers).

Examples of the groups obtained by bonding a linear hydrocarbon group and a trialkyl-substituted alicyclic hydrocarbon group include groups represented by formula (III-2) shown below (hereafter sometimes referred to as "group (III-2)").

[Chemical formula 74]

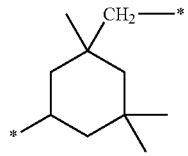

(III-2)

Examples of the unsubstituted aromatic hydrocarbon groups include a phenylene group and diphenylalkane-diyl groups.

Examples of the monoalkyl-substituted arylene groups include a toluene-diyl group, ethylphenylene group, and propylphenylene group.

Examples of the dialkyl-substituted arylene groups include a xylene-diyl group, diethylphenylene group, dipropylphenylene group, and tetramethylxylylene group.

Among the various possibilities, each of $R^{15}$ and $R^{16}$ is preferably an alkylenebis(cyclohexylene) group, group (III-2), diphenylalkane-diyl group, toluene-diyl group, tetramethylxylylene group, or a group represented by general formula (VI) shown below (hereafter sometimes referred to as "group (VI)"), is more preferably a group represented by formula (III-1) shown below (hereafter sometimes referred to a "group (III-1)"), the group (III-2), a group represented by formula (III-3) shown below (hereafter sometimes referred to a "group (III-3)"), a group represented by formula (III-4) shown below (hereafter sometimes referred to a "group (III-4)"), a group represented by formula (III-5) shown below (hereafter sometimes referred to a "group (III-5)"), a group represented by formula (III-6) shown below (hereafter sometimes referred to a "group (III-6)"), or the group (VI), and is even more preferably the group (VI).

[Chemical formula 75]

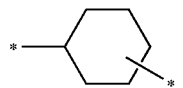

(III-1)

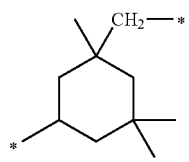

(III-2)

(III-3)

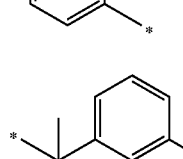

(III-4)

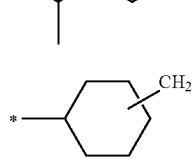

(III-5)

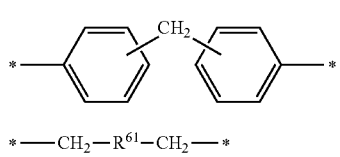

(In the formulas, each asterisk represents a bonding site. In general formula (VI), $R^{61}$ represents an alkylene group of at least 1 but not more than 18 carbon atoms, or an arylene group of at least 6 but not more than 18 carbon atoms.)

($R^{61}$)

Examples of the alkylene group of at least 1 but not more than 18 carbon atoms for $R^{61}$ include groups of at least 1 but not more than 18 carbon atoms among the groups exemplified as the aliphatic hydrocarbon group of at least 1 but not more than 22 carbon atoms in the above description of "$R^{11}$ and $R^{12}$".

Examples of the arylene group of at least 6 but not more than 18 carbon atoms for $R^{61}$ include groups of at least 6 but not more than 18 carbon atoms among the groups exemplified as the aromatic hydrocarbon group of at least 6 but not more than 22 carbon atoms in the above description of "$R^{11}$ and $R^{12}$".

Among the various possibilities, $R^{61}$ is preferably a trimethylene group, tetramethylene group, cyclohexylene group or phenylene group.

Preferred examples of the group (VI) include groups represented by general formula (VI-1) shown below (hereafter sometimes referred to as "group (VI-1)"), groups represented by general formula (VI-2) shown below (hereafter sometimes referred to as "group (VI-2)"), and groups represented by general formula (VI-3) shown below (hereafter sometimes referred to as "group (VI-3)").

[Chemical formula 76]

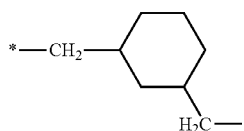

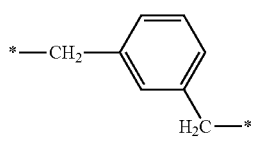

(In the formulas, each asterisk represents a bonding site. In general formula (VI-1), n61 represents an integer of at least 3 but not more than 10.)

Preferred examples of the group (VI-1) include a trimethylene group, tetramethylene group, pentamethylene group and hexamethylene group, and among these, a tetramethylene group, pentamethylene group or hexamethylene group is particularly preferred.

In those cases where $R^{15}$ and $R^{16}$ are residues obtained by removing two isocyanate groups from a polyisocyanate derived from a diisocyanate, the polyisocyanate that gives rise to $R^{15}$ and $R^{16}$ has at least one functional group selected from the group consisting of an isocyanurate group, allophanate group, biuret group, uretdione group, iminooxadiazinedione group and urethane group. Among the various possibilities, the polyisocyanate preferably has an isocyanurate group.

[$X^{15}$ and $X^{16}$]

Each of $X^{15}$ and $X^{16}$ independently represents the group (VIII). $X^{15}$ and $X^{16}$ may be the same or different, but are preferably the same in terms of ease of production.

The compound (2β) has a structure in which the main skeleton has a hydrophobic carbodiimide group and both terminals are hydrophobic groups (VIII), and can therefore be dispersed stably in hydrophobic solvents.

($Y^{81}$)

$Y^{81}$ represents a carbodiimide group (—N=C=N—), a urea group (—NHC(=O)NH—) or a urethane group (—NHC(=O)O—).

($R^{81}$)

The monovalent hydrocarbon group for $R^{81}$ may be an aliphatic hydrocarbon group or an aromatic hydrocarbon group.

The monovalent aliphatic hydrocarbon group (alkyl group) may be chain-like or cyclic. The chain-like aliphatic hydrocarbon group (chain-like alkyl group) may be either linear or branched. Examples of linear alkyl groups include a methyl group, ethyl group, n-propyl group, n-butyl group, n-pentyl group, n-hexyl group, n-heptyl group, n-octyl group, n-nonyl group, n-decyl group, n-undecyl group and n-dodecyl group. Examples of branched alkyl groups include an isopropyl group, isobutyl group, sec-butyl group, tert-butyl group, isopentyl group and isohexyl group. Examples of cyclic alkyl groups include a cyclopropyl group, cyclobutyl group, cyclopentyl group and cyclohexyl group.

The aliphatic hydrocarbon group may have a substituent. Examples of the substituent include aromatic hydrocarbon groups and the like.

Examples of aliphatic hydrocarbon groups having a substituent include a benzyl group, α-methylbenzyl group, and α,α-dimethylbenzyl group.

Examples of monovalent aromatic hydrocarbon groups (aryl groups) include a phenyl group and a naphthyl group.

The aromatic hydrocarbon group may have a substituent. Examples of the substituent include aliphatic hydrocarbon groups and the like.

Examples of aromatic hydrocarbon groups having a substituent include a tolyl group and a xylyl group.

Examples of the hydrocarbon group that may contain a carbonyl group or an ester linkage for $R^{81}$ include groups represented by general formula (VIIIa) shown below (hereafter sometimes referred to as "group (VIIIa)") and groups represented by general formula (VIIIb) shown below (hereafter sometimes referred to as "group (VIIIb)").

[Chemical formula 77]

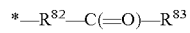

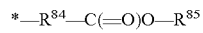

(In general formula (VIIIa) and general formula (VIIIb), each of $R^{82}$ and $R^{84}$ independently represents a single bond or a divalent hydrocarbon group of at least 1 but not more than 10 carbon atoms. Each of $R^{83}$ and $R^{85}$ independently represents a monovalent hydrocarbon group of at least 1 but not more than 11 carbon atoms. The number of carbon atoms x1 in $R^{82}$ and the number of carbon atoms y1 in $R^{83}$ satisfy the relationships 0<y1 and 1≤x1+y1≤11. The number of carbon atoms x2 in $R^{84}$ and the number of carbon atoms y2 in $R^{85}$ satisfy the relationships 0<y2 and 1≤x2+y2≤11. Each asterisk represents a bonding site.)

The divalent hydrocarbon group for $R^{82}$ or $R^{84}$ may be an aliphatic hydrocarbon group or an aromatic hydrocarbon group.

The divalent aliphatic hydrocarbon group (alkylene group) may be chain-like or cyclic. The chain-like aliphatic hydrocarbon group (chain-like alkylene group) may be either linear or branched. Examples of linear alkylene groups include a methylene group, ethylene group, trimethylene group, tetramethylene group, pentamethylene group, and hexamethylene group. Examples of branched alkylene groups include a 1-methylmethane-1,1-diyl group, 1,2-dimethylethylene group, and 1-methylethane-1,1-diyl group. Examples of cyclic alkylene groups include a cyclopropylene group, cyclobutylene group cyclopentylene group, and cyclohexylene group.

Examples of the divalent aromatic hydrocarbon group (arylene group) include a phenylene group and a naphthylene group.

Among the various possibilities, the divalent hydrocarbon group for $R^{82}$ and $R^{84}$ is preferably an alkylene group, more preferably a chain-like alkylene group, and even more preferably a chain-like alkylene group of at least 1 but not more than 3 carbon atoms.

Examples of the monovalent hydrocarbon group for $R^{83}$ and $R^{85}$ include monovalent hydrocarbon groups of at least 1 but not more than 11 carbon atoms among those groups exemplified above for $R^{81}$.

Among these groups, each of $R^{83}$ and $R^{85}$ is preferably an alkyl group of at least 1 but not more than 8 carbon atoms, more preferably a chain-like alkyl group of at least 1 but not more than 6 carbon atoms, and even more preferably a linear alkyl group of at least 1 but not more than 4 carbon atoms.

Among the various possibilities, $R^{81}$ is preferably a monovalent hydrocarbon group of at least 1 but not more than 10 carbon atoms that may include a carbonyl group or an ester linkage, more preferably a monovalent hydrocarbon group of at least 1 but not more than 9 carbon atoms that may include an ester linkage, even more preferably an alkyl group of at least 1 but not more than 6 carbon atoms, and particularly preferably a linear alkyl group of at least 1 but not more than 6 carbon atoms.

The group (VIII) is a group represented by general formula (VIII-1) shown below (hereafter sometimes referred to as "group (VIII-1)"), a group represented by general formula (VIII-2) shown below (hereafter sometimes referred to as "group (VIII-2)"), or a group represented by general formula (VIII-3) shown below (hereafter sometimes referred to as "group (VIII-3)").

[Chemical formula 78]

(VIII-1)

(VIII-2)

(VIII-3)

(In general formula (VIII-1), general formula (VIII-2) and general formula (VIII-3), each of $R^{811}$, $R^{821}$ and $R^{831}$ is independently the same as R81 described above.)

Preferred examples of the group (VIII-1) include groups represented by general formula (VIII-1-1) shown below (hereafter sometimes referred to as "group (VIII-1-1)"), groups represented by general formula (VIII-1-2) shown below (hereafter sometimes referred to as "group (VIII-1-2)"), groups represented by general formula (VIII-1-3) shown below (hereafter sometimes referred to as "group (VIII-1-3)"), groups represented by general formula (VIII-1-4) shown below (hereafter sometimes referred to as "group (VIII-1-4)"), groups represented by general formula (VIII-1-5) shown below (hereafter sometimes referred to as "group (VIII-1-5)"), groups represented by general formula (VIII-1-6) shown below (hereafter sometimes referred to as "group (VIII-1-6)"), groups represented by general formula (VIII-1-7) shown below (hereafter sometimes referred to as "group (VIII-1-7)"), groups represented by general formula (VIII-1-8) shown below (hereafter sometimes referred to as "group (VIII-1-8)"), and groups represented by general formula (VIII-1-9) shown below (hereafter sometimes referred to as "group (VIII-1-9)").

[Chemical formula 79]

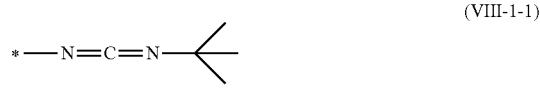
(VIII-1-1)

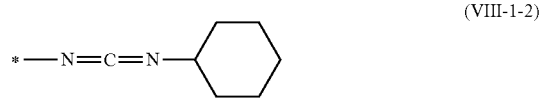
(VIII-1-2)

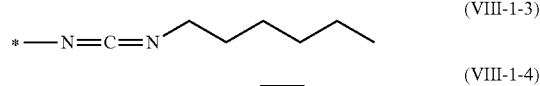
(VIII-1-3)

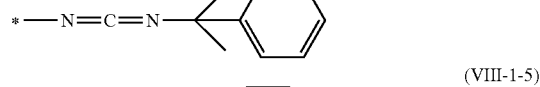
(VIII-1-4)

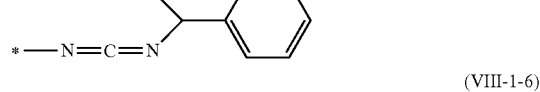
(VIII-1-5)

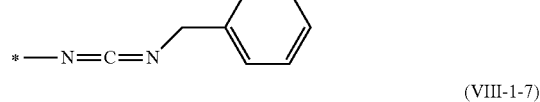
(VIII-1-6)

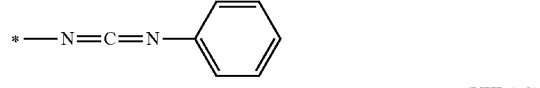
(VIII-1-7)

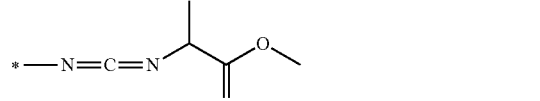
(VIII-1-8)

(VIII-1-9)

(In the above formulas, each asterisk represents a bonding site.)

Preferred examples of the group (VIII-2) include groups represented by general formula (VIII-2-1) shown below (hereafter sometimes referred to as "group (VIII-2-1)"), groups represented by general formula (VIII-2-2) shown below (hereafter sometimes referred to as "group (VIII-2-2)"), groups represented by general formula (VIII-2-3) shown below (hereafter sometimes referred to as "group (VIII-2-3)"), groups represented by general formula (VIII-2-4) shown below (hereafter sometimes referred to as "group (VIII-2-4)"), groups represented by general formula (VIII-2-5) shown below (hereafter sometimes referred to as "group (VIII-2-5)"), groups represented by general formula (VIII-2-6) shown below (hereafter sometimes referred to as "group (VIII-2-6)"), groups represented by general formula (VIII-2-7) shown below (hereafter sometimes referred to as "group (VIII-2-7)"), groups represented by general formula (VIII-2-8) shown below (hereafter sometimes referred to as "group (VIII-2-8)"), and groups represented by general formula (VIII-2-9) shown below (hereafter sometimes referred to as "group (VIII-2-9)").

[Chemical formula 80]

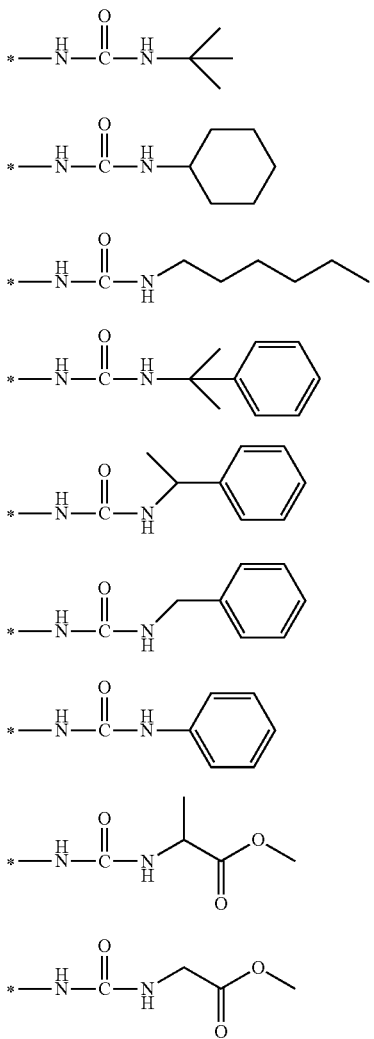

(In the above formulas, each asterisk represents a bonding site.)

Preferred examples of the group (VIII-3) include groups represented by general formula (VIII-3-1) shown below (hereafter sometimes referred to as "group (VIII-3-1)"), groups represented by general formula (VIII-3-2) shown below (hereafter sometimes referred to as "group (VIII-3-2)"), groups represented by general formula (VIII-3-3) shown below (hereafter sometimes referred to as "group (VIII-3-3)"), groups represented by general formula (VIII-3-4) shown below (hereafter sometimes referred to as "group (VIII-3-4)"), groups represented by general formula (VIII-3-5) shown below (hereafter sometimes referred to as "group (VIII-3-5)"), groups represented by general formula (VIII-3-6) shown below (hereafter sometimes referred to as "group (VIII-3-6)"), and groups represented by general formula (VIII-3-7) shown below (hereafter sometimes referred to as "group (VIII-3-7)").

[Chemical formula 81]

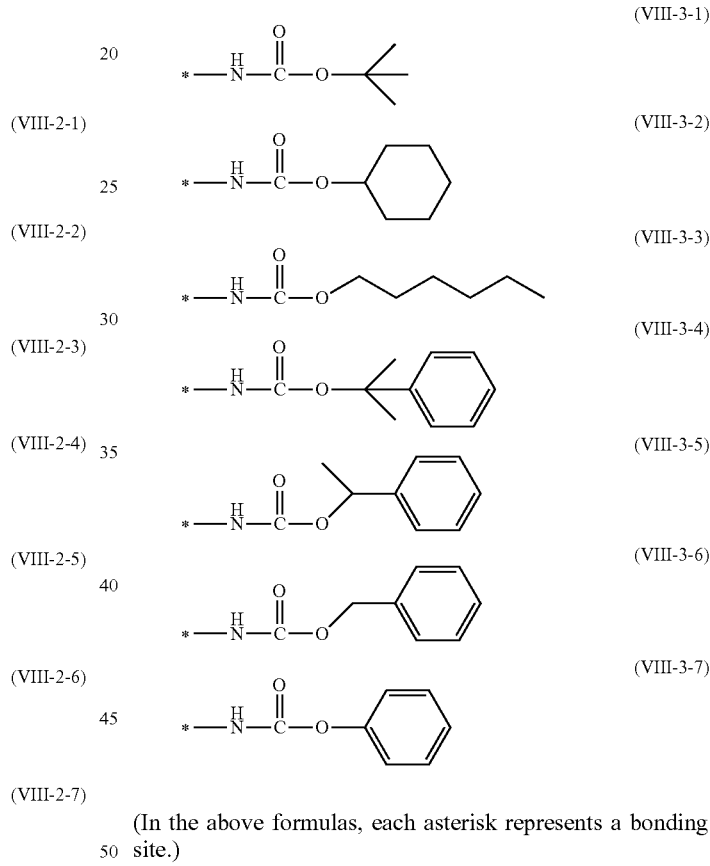

(In the above formulas, each asterisk represents a bonding site.)

<<Method for Producing Carbodiimide Compound>>

The carbodiimide compound of an embodiment of the present invention can be produced, for example, using the method described below.

For example, the compound (2a) described above can be produced by a first production method having a step of subjecting a diisocyanate, a polyisocyanate derived from a diisocyanate, or a combination thereof to a decarboxylation condensation reaction in the presence of a catalyst to obtain a carbodiimide compound having isocyanate groups at the terminals (hereafter sometimes referred to as the "carbodiimide compound A") (hereafter sometimes referred to as the "carbodiimide compound A production step"), and a step of reacting the obtained carbodiimide compound A with a compound represented by general formula (IV) shown below (hereafter sometimes referred to as "compound (IV)") or a compound represented by general formula (IV') shown below (hereafter sometimes referred to as "compound (IV')") to obtain the compound (2α) (hereafter sometimes referred to as the "compound (2α) production step 1").

[Chemical formula 82]

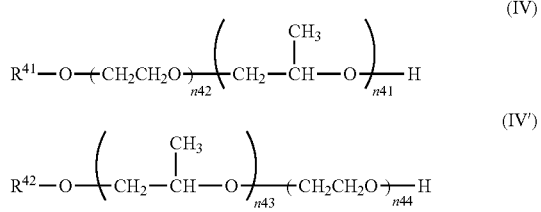

(In general formula (IV), n41 and n42 are the same as n21 and n22 described above. $R^{41}$ is the same as $R^{21}$ described above.

In general formula (IV'), n43 and n44 are the same as n21 and n22 described above. $R^{42}$ is the same as $R^{21}$ described above.)

Alternatively, the compound (2α) can be produced by a second production method having a step of reacting a diisocyanate, a polyisocyanate derived from a diisocyanate, or a combination thereof with the compound (IV) or the compound (IV') to obtain a hydrophilic isocyanate compound (hereafter sometimes referred to as the "hydrophilic isocyanate compound production step"), and a step of subjecting the obtained hydrophilic isocyanate compound to a decarboxylation condensation reaction in the presence of a catalyst to obtain the compound (2α) (hereafter sometimes referred to as the "compound (2α) production step 2").

In the first production method, the formation reaction for the carbodiimide group is performed, and then a hydrophilic group introduction reaction is conducted to obtain the compound (2α). On the other hand, in the second production method, the hydrophilic group introduction reaction is performed, and then the formation reaction for the carbodiimide group is conducted to obtain the compound (2α). In other words, although the reaction sequence is different, the reaction conditions and the raw materials used are the same.
<First Production Method>
[Carbodiimide Compound A Production Step]

In the carbodiimide compound A production step, a diisocyanate, a polyisocyanate derived from a diisocyanate, or a combination thereof is subjected to a decarboxylation condensation reaction in the presence of a catalyst to obtain the carbodiimide compound A. The decarboxylation condensation reaction for obtaining the carbodiimide compound A is a conventionally known reaction.

The reaction temperature may be set, for example, to at least 100° C. but not more than 200° C.

The reaction may be conducted in the presence of a solvent or in the absence of a solvent. There are no particular limitations on the solvent, and examples include hydrocarbons, ethers, compounds having an amide linkage, sulfoxides, and halogenated hydrocarbons. Examples of the hydrocarbons include benzene, toluene and xylene. Examples of the ethers include tetrahydrofuran (hereafter sometimes abbreviated as THF) and diethyl ether. Examples of the compounds having an amide linkage include N,N-dimethylformamide. Examples of the sulfoxides include dimethylsulfoxide. Examples of the halogenated hydrocarbons include methylene chloride and chlorobenzene. A single solvent may be used alone, or a combination of two or more solvents may be used, and in the case where a combination of two or more solvents is used, the combination and proportions of the solvents may be selected as appropriate.

Examples of the catalyst include phospholene oxides. Specific examples of these phospholene oxides include 1-phenyl-2-phospholene-1-oxide and 3-methyl-1-phenyl-2-phospholene-1-oxide.

In the carbodiimide compound A production step, following completion of the reaction, a conventional technique may be used to conduct a post-treatment as necessary, and the carbodiimide compound A may then be collected. In other words, if necessary, a single post-treatment or a combination of two or more post-treatments such as filtration, washing, extraction, pH adjustment, dewatering or concentration may be conducted, and the carbodiimide compound A may then be collected by concentration, crystallization, reprecipitation or column chromatography or the like. Further, if necessary, the collected carbodiimide compound A may be further purified by using one operation or a combination of two or more operations such as crystallization, reprecipitation, column chromatography, extraction, and stirred washing of the crystals in a solvent.

In the carbodiimide compound A production step, following completion of the reaction, the carbodiimide compound A may be simply used in the next step without undergoing collection, but in terms of improving the yield of the compound (2α) that represents the target product, the carbodiimide compound A is preferably collected using the methods described above.
(Diisocyanate)

Examples of the diisocyanate used in the carbodiimide compound A production step include aliphatic diisocyanates, alicyclic diisocyanates and aromatic diisocyanates.

Examples of the aliphatic diisocyanates include 1,4-tetramethylene diisocyanate, 1,5-pentamethylene diisocyanate, HDI, 2,2,4-trimethyl-1,6-hexamethylene diisocyanate, and lysine diisocyanate.

Examples of the alicyclic diisocyanates include IPDI, 4,4'-methylenebiscyclohexyl diisocyanate (hereafter sometimes abbreviated as "hydrogenated MDI"), and dimethylcyclohexane diisocyanate (hereafter sometimes abbreviated as "hydrogenated XDI").

Examples of the aromatic diisocyanates include 2,4-tolylene diisocyanate, 2,6-tolylene diisocyanate and mixtures thereof (hereafter sometimes abbreviated as TDIs), diphenylmethane-4,4'-diisocyanate (hereafter sometimes abbreviated as MDI), naphthalene-1,5-diisocyanate hereafter sometimes abbreviated as NDI), 3,3-dimethyl-4,4-diphenylene diisocyanate (hereafter sometimes abbreviated as TODI), crude TDIs, polymethylene polyphenyl diisocyanate, crude MDI, phenylene diisocyanate, xylylene diisocyanate (hereafter sometimes abbreviated as XDI), and tetramethylxylylene diisocyanate (hereafter sometimes abbreviated as TMXDI).

Among these compounds, the diisocyanate is preferably tetramethylene diisocyanate, pentamethylene diisocyanate, hexamethylene diisocyanate, IPDI, hydrogenated MDI, hydrogenated XDI, MDI, XDI or TMXDI.
(Polyisocyanate)

Examples of polyisocyanates that can be used in the carbodiimide compound A production step include the same compounds as those exemplified above in the section entitled "$R^{13}$ and $R^{14}$". Among these compounds, polyisocyanates having an isocyanurate group are preferred as the polyisocyanate.

In those cases where a polyisocyanate is used in the carbodiimide compound A production step, the polyisocyanate is preferably used in combination with a diisocyanate. In such cases, the amount used of the polyisocyanate, expressed as a mass ratio relative to the diisocyanate (polyisocyanate/diisocyanate), may be set, for example, to a ratio of at least 20/80 but not more than 1/99, or a ratio of at least 15/85 but not more than 5/95.

[Compound (2α) Production Step 1]

In the compound (2α) production step 1, the obtained carbodiimide compound A is reacted with the compound (IV) or the compound (IV') to obtain the compound (2α).

Specifically, the isocyanate terminals of the carbodiimide compound A are reacted with the hydroxyl group at the terminal of the compound (IV) or compound (IV'), thereby introducing residue obtained by removing the hydrogen atom from the terminal hydroxyl group of the compound (IV) or compound (IV') at the terminals of the compound A to produce the compound (2α).

The reaction temperature may be set, for example, to at least 80° C. but not more than 200° C., or to at least 100° C. but not more than 150° C.

The reaction may be conducted in the presence of a solvent or in the absence of a solvent. Examples of the solvent include the same solvents as those exemplified above in the section entitled "Carbodiimide Compound A Production Step".

(Compound (IV) and Compound (IV'))

The compound (IV) is a compound represented by general formula (IV) shown below, and the compound (IV') is a compound represented by general formula (IV') shown below, with each compound being a poly(oxyethyleneoxypropylene) (formed using at least one of random and block polymerization) glycol monoalkyl ether.

[Chemical formula 83]

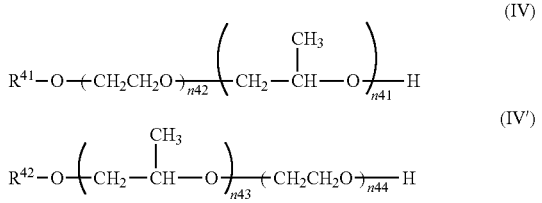

(In general formula (IV), n41 and n42 are the same as n21 and n22 described above. $R^{41}$ is the same as $R^{21}$ described above.

In general formula (IV'), n43 and n44 are the same as n21 and n22 described above. $R^{42}$ is the same as $R^{21}$ described above.

Preferred examples of the compound (IV) include compounds represented by general formula (IV-1) shown below (hereafter sometimes referred to as "compound (IV-1)"), and compounds represented by general formula (IV-2) shown below (hereafter sometimes referred to as "compound (IV-2)").

[Chemical formula 84]

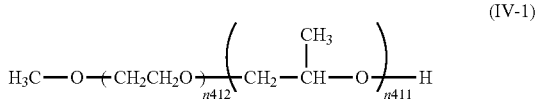

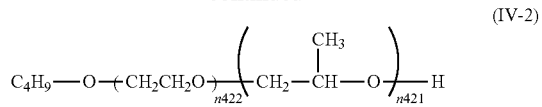

(In general formula (IV-1) and general formula (IV-2), n411, n412, n421 and n422 are the same as n21 and n22 described above.)

Further, preferred examples of the compound (IV') include compounds represented by general formula (IV'-1) shown below (hereafter sometimes referred to as "compound (IV'-1)"), and compounds represented by general formula (IV'-2) shown below (hereafter sometimes referred to as "compound (IV'-2)").

[Chemical formula 85]

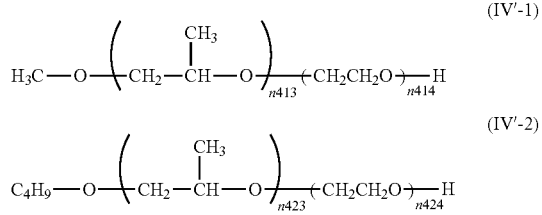

(In general formula (IV'-1) and general formula (IV'-2), n413, n414, n423 and n424 are the same as n21 and n22 described above.)

The lower limit for the molecular weights of the compound (IV) and the compound (IV') is preferably 50, more preferably 100, even more preferably 150, and particularly preferably 200. On the other hand, the upper limit for the molecular weights is preferably 3,000, more preferably 2,500, even more preferably 2,000, and particularly preferably 1,500.

In other words, the molecular weights of the compound (IV) and the compound (IV') are preferably at least 50 but not more than 3,000, more preferably at least 100 but not more than 2,500, even more preferably at least 150 but not more than 2,000, and particularly preferably at least 200 but not more than 1,500.

Provided the molecular weights of the compound (IV) and the compound (IV') fall within the above range, the water dispersibility of the compound (2α) is more favorable.

In the compound (2α) production step 1, following completion of the reaction, the compound (2α) can be collected using the same methods as those described above for the carbodiimide compound A production step, and the collected compound (2α) may then be further purified using the same methods as those described above.

The structures of the compound (2α), the compound (IV), the compound (IV'), the carbodiimide compound A, the diisocyanate and the polyisocyanate and the like can each be confirmed using conventional techniques such as nuclear magnetic resonance (NMR) spectroscopy methods, mass spectrometry methods (MS) and infrared spectroscopy methods (IR).

<Second Production Method>

[Hydrophilic Isocyanate Compound Production Step]

In the hydrophilic isocyanate compound production step, a diisocyanate, a polyisocyanate derived from a diisocyanate, or a combination thereof is reacted with the compound (IV) or the compound (IV') to obtain a hydrophilic isocyanate compound.

Specifically, the terminal isocyanate groups of the diisocyanate or polyisocyanate are reacted with the terminal hydroxyl group of the compound (IV) or compound (IV'), thereby introducing the residue obtained by removing the hydrogen atom from the terminal hydroxyl group of the compound (IV) or compound (IV') at the terminals of the diisocyanate or polyisocyanate to produce the hydrophilic isocyanate compound.

The reaction temperature may be set, for example, to a temperature of at least 80° C. but not more than 200° C., or a temperature of at least 100° C. but not more than 150° C.

The reaction may be conducted in the presence of a solvent or in the absence of a solvent. Examples of the solvent include the same solvents as those exemplified above in the section entitled "Carbodiimide Compound A Production Step".

In the hydrophilic isocyanate compound production step, following completion of the reaction, the hydrophilic isocyanate compound may be simply used in the next step without undergoing collection, but in terms of improving the yield of the compound ($2\alpha$) that represents the target product, the hydrophilic isocyanate compound is preferably collected using the methods described above.

[Compound ($2\alpha$) Production Step 2]

In the compound ($2\alpha$) production step 2, the obtained hydrophilic isocyanate compound is subjected to a decarboxylation condensation reaction in the presence of a catalyst to obtain the compound ($2\alpha$). At this time, a diisocyanate having no introduced hydrophilic groups, a polyisocyanate derived from a diisocyanate, or a combination thereof may also be added. The added diisocyanate or polyisocyanate may be the same as the compound used in the hydrophilic isocyanate compound production step described above, or may be a different compound.

Examples of the catalyst include the same catalysts as those exemplified above in the section entitled "Carbodiimide Compound A Production Step".

The reaction temperature may be set, for example, to a temperature of at least 100° C. but not more than 200° C.

The reaction may be conducted in the presence of a solvent or in the absence of a solvent. Examples of the solvent include the same solvents as those exemplified above in the section entitled "Carbodiimide Compound A Production Step".

In the compound ($2\alpha$) production step 2, following completion of the reaction, the compound ($2\alpha$) can be collected using the same methods as those described above for the carbodiimide compound A production step, and the collected compound ($2\alpha$) may then be further purified using the same methods as those described above.

The structures of the compound ($2\alpha$), the compound (IV), the compound (IV'), the hydrophilic isocyanate compound, the diisocyanate and the polyisocyanate and the like can each be confirmed using conventional techniques such as nuclear magnetic resonance (NMR) spectroscopy methods, mass spectrometry methods (MS) and infrared spectroscopy methods (IR).

Furthermore, the compound ($2\beta$) described above can be produced, for example, using a production method having a step of reacting a diisocyanate, a polyisocyanate derived from a diisocyanate, or a combination thereof with a hydrophobic group-containing compound in the presence of a catalyst to obtain a carbodiimide compound having hydrophobic groups at the terminals, namely the compound ($2\beta$) (hereafter sometimes referred to as the "compound ($2\beta$) production step").

<Compound ($2\beta$) Production Step>

In the compound ($2\beta$) production step, a diisocyanate, a polyisocyanate derived from a diisocyanate, or a combination thereof is subjected to a decarboxylation condensation reaction in the presence of a catalyst to form a carbodiimide group, and at the same time, the terminal isocyanate groups of the diisocyanate or the polyisocyanate derived from a diisocyanate are reacted with a hydrophobic group-containing compound to introduce hydrophobic groups at the terminals, thus obtaining the compound ($2\beta$). The decarboxylation condensation reaction and the reaction for introducing hydrophobic groups at the terminals are conventionally known reactions.

The reaction temperature may be set, for example, to a temperature of at least 100° C. but not more than 200° C.

The reaction may be conducted in the presence of a solvent or in the absence of a solvent. There are no particular limitations on the solvent, and examples include hydrocarbons, ethers, compounds having an amide linkage, sulfoxides, and halogenated hydrocarbons. Examples of the hydrocarbons include benzene, toluene and xylene. Examples of the ethers include tetrahydrofuran (hereafter sometimes abbreviated as THF) and diethyl ether. Examples of the compounds having an amide linkage include N,N-dimethylformamide. Examples of the sulfoxides include dimethylsulfoxide. Examples of the halogenated hydrocarbons include methylene chloride and chlorobenzene. A single solvent may be used alone, or a combination of two or more solvents may be used, and in the case where a combination of two or more solvents is used, the combination and proportions of the solvents may be selected as appropriate.

Examples of the catalyst include phospholene oxides. Specific examples of these phospholene oxides include 1-phenyl-2-phospholene-1-oxide and 3-methyl-1-phenyl-2-phospholene-1-oxide.

In the compound ($2\beta$) production step, following completion of the reaction, a conventional technique may be used to conduct a post-treatment as necessary, and the compound ($2\beta$) may then be collected. In other words, if necessary, a single post-treatment or a combination of two or more post-treatments such as filtration, washing, extraction, pH adjustment, dewatering or concentration may be conducted, and the compound ($2\beta$) may then be collected by concentration, crystallization, reprecipitation or column chromatography or the like. Further, if necessary, the collected compound ($2\beta$) may be further purified by using one operation or a combination of two or more operations such as crystallization, reprecipitation, column chromatography, extraction, and stirred washing of the crystals in a solvent.

(Diisocyanate)

Examples of the diisocyanate used in the compound ($2\beta$) production step include aliphatic diisocyanates, alicyclic diisocyanates and aromatic diisocyanates.

Examples of the aliphatic diisocyanates include 1,4-tetramethylene diisocyanate, 1,5-pentamethylene diisocyanate, hexamethylene diisocyanate (hereafter sometimes abbreviated as HDI), 2,2,4-trimethyl-1,6-hexamethylene diisocyanate, and lysine diisocyanate.

Examples of the alicyclic diisocyanates include isophorone diisocyanate (hereafter sometimes abbreviated as IPDI), 4,4'-methylenebiscyclohexyl diisocyanate (hereafter sometimes abbreviated as "hydrogenated MDI"), and dimethylcyclohexane diisocyanate (hereafter sometimes abbreviated as "hydrogenated XDI").

Examples of the aromatic diisocyanates include 2,4-tolylene diisocyanate, 2,6-tolylene diisocyanate and mixtures thereof (hereafter sometimes abbreviated as TDIs), diphenylmethane-4,4'-diisocyanate (hereafter sometimes abbreviated as MDI), naphthalene-1,5-diisocyanate hereafter sometimes abbreviated as NDI), 3,3-dimethyl-4,4-diphenylene diisocyanate (hereafter sometimes abbreviated as TODI), crude TDIs, polymethylene polyphenyl diisocyanate, crude MDI, phenylene diisocyanate, xylylene diisocyanate (hereafter sometimes abbreviated as XDI), and tetramethylxylylene diisocyanate (hereafter sometimes abbreviated as TMXDI).

Among these compounds, the diisocyanate is preferably tetramethylene diisocyanate, pentamethylene diisocyanate, hexamethylene diisocyanate, IPDI, hydrogenated MDI, hydrogenated XDI, MDI, XDI or TMXDI.

(Polyisocyanate)

Examples of polyisocyanates that can be used in the compound (2β) production step include the same compounds as those exemplified above in the section entitled "$R^{15}$ and $R^{16}$". Among these compounds, polyisocyanates having an isocyanurate group are preferred as the polyisocyanate.

In those cases where a polyisocyanate is used in the compound (2β) production step, the polyisocyanate is preferably used in combination with a diisocyanate. In such cases, the amount used of the polyisocyanate, expressed as a mass ratio relative to the diisocyanate (polyisocyanate/diisocyanate), may be set, for example, to a ratio of at least 20/80 but not more than 1/99, or a ratio of at least 15/85 but not more than 5/95.

(Hydrophobic Group-Containing Compound)

A hydrophobic group-containing compound is a compound having a hydrophobic group. Examples of the hydrophobic group include hydrocarbon groups. In addition to the hydrophobic group, the hydrophobic group-containing compound preferably also has one functional group capable of reacting with a terminal isocyanate group of a diisocyanate or a polyisocyanate derived from a diisocyanate. Examples of this functional group include an isocyanate group, amino group and hydroxyl group. Specific examples of the hydrophobic group-containing compound include monofunctional isocyanates, primary amine compounds, and monohydric alcohol compounds. Specific examples of the monofunctional isocyanates include compounds represented by general formula (IX-1) shown below. Specific examples of the primary amine compounds include compounds represented by general formula (IX-2) shown below. Specific examples of the monohydric alcohol compounds include compounds represented by general formula (IX-3) shown below.

[Chemical formula 86]

$$R^{911}-NCO \quad (IX-1)$$

$$R^{921}-NH_2 \quad (IX-2)$$

$$R^{931}-OH \quad (IX-3)$$

(In general formula (IX-1), $R^{911}$ is the same as $R^{811}$. In general formula (IX-2), $R^{921}$ is the same as $R^{821}$. In general formula (IX-3), $R^{931}$ is the same as $R^{831}$.

Preferred examples of the compound (IX-1) include tert-butyl isocyanate, cyclohexyl isocyanate, 1-hexyl isocyanate, α,α-dimethylbenzyl isocyanate, (S)-1-phenylethyl isocyanate, benzyl isocyanate, phenyl isocyanate, methyl (S)-(−)-2-isocyanatopropionate, and methyl (S)-(−)-2-isocyanatoacetate.

Preferred examples of the compound (IX-2) include tert-butylamine, cyclohexylamine, N-hexylamine, α,α-dimethylbenzylamine, (S)-1-phenylethylamine, benzylamine, phenylamine, alanine methyl ester, and glycine methyl ester.

Preferred examples of the compound (IX-3) include tert-butyl alcohol, cyclohexanol, 1-hexanol, 2-phenyl-2-propanol, 1-phenylethanol, benzyl alcohol, and phenol.

The structures of the compound (2β), the compound (IX-1), the compound (IX-2), the compound (IX-3), the diisocyanate and the polyisocyanate and the like can each be confirmed using conventional techniques such as nuclear magnetic resonance (NMR) spectroscopy methods, mass spectrometry methods (MS) and infrared spectroscopy methods (IR).

<<Usage Applications>>

The uretonimine group-containing compound or carbodiimide compound of an embodiment of the present invention has hydrophilic groups at the terminals, and therefore has favorable water dispersibility, and exhibits excellent storage stability when used in a resin composition. Accordingly, the compound of an embodiment of the present invention can be used favorably as a curing agent or water-dispersed composition or the like of a coating material composition such as an electrodeposition coating material.

In other words, in one embodiment, the present invention provides a curing agent composition containing an uretonimine group-containing compound or a carbodiimide compound.

(Other Crosslinking Agent)

The curing agent composition may also contain another crosslinking agent in addition to the uretonimine group-containing compound or carbodiimide compound described above. Examples of the other crosslinking agent include oxazoline compounds, epoxy compounds, melamine compounds, isocyanate compounds, hydrazine compounds, and semicarbazide compounds.

Examples of the oxazoline compounds include polymeric compounds having at least two oxazoline groups on side chains, and monomer compounds having at least two oxazoline groups within each molecule. Examples of commercially available oxazoline compounds include EPOCROS WS-500 (product name, manufactured by Nippon Shokubai Co., Ltd.).

The epoxy compound may be any resin having two or more epoxy groups in each molecule. Specific examples of epoxy group-containing compounds include bisphenol-type epoxy group-containing compounds obtained by adding epichlorohydrin to bisphenol, novolac-type epoxy group-containing compounds obtained by adding epichlorohydrin to phenol novolac resins, and polyethylene glycol diglycidyl ether. The epoxy group-containing compound may be in a water-dispersed state if necessary.

Examples of the melamine compounds include partially or fully methylolated melamine resins obtained by a reaction between melamine and an aldehyde.

Examples of the aldehyde include formaldehyde and para-formaldehyde.

Further, compounds obtained by partially or fully etherifying the methylol groups of the methylolated melamine resin with an alcohol may also be used. Examples of the alcohol used for the etherification include methanol, ethanol, n-propanol, isopropanol, n-butanol, isobutanol, 2-ethylbutanol, and 2-ethylhexanol.

Examples of commercially available melamine compounds include CYMEL 303, CYMEL 323, CYMEL 325, CYMEL 327, CYMEL 350, CYMEL 370, CYMEL 380, CYMEL 385, CYMEL 212, CYMEL 251, CYMEL 254, and MYCOAT 776 (all product names, manufactured by the Allnex Group).

The isocyanate compound is a diisocyanate or polyisocyanate having a hydrocarbon group that may be aliphatic, alicyclic or aromatic, and isocyanate groups. Examples of the diisocyanate include tetramethylene diisocyanate (TMDI), pentamethylene diisocyanate (PDI), hexamethylene diisocyanate (HDI), 2,2,4-trimethylhexane-1,6-diisocyanate, 2-methylpentane-1,5-diisocyanate (MPDI), 1,3-bis(isocyanatomethyl)-cyclohexane (1,3-H6-XDI), 3(4)-isocyanatomethyl-1-methylcyclohexyl isocyanate (IMCI), isophorone diisocyanate (IPDI), bis(isocyanatomethyl)-norbomane (NBDI), 1,3-bis(isocyanatomethyl)-benzene, 1,3-bis(2-isocyanatopropyl-2) benzene, 4,4'-dicyclohexylmethane diisocyanate (H12MDI), and lysine diisocyanate (LDI). Among these, from the viewpoints of weather resistance and ease of industrial availability, HDI or IPDI is preferred.

The polyisocyanates mentioned above are compounds obtained by polymerizing an aforementioned diisocyanate using a catalyst or heating, and include an isocyanurate structure, uretdione structure, allophanate structure, iminooxadiazinedione structure, urethane structure, or biuret structure or the like within the molecule. Among these compounds, from the viewpoint of the weather resistance, the polyisocyanate preferably has an isocyanurate structure.

Furthermore, examples of other isocyanate compounds include triisocyanates such as 4-isocyanatomethyl-1,8-octamethylene diisocyanate (NTI), 1,3,6-hexamethylene triisocyanate (HTI), bis(2-isocyanatoethyl) 2-isocyanatoglutarate (GTI), and lysine triisocyanate (LTI).

Combinations of two or more of these isocyanate compounds may also be used.

Moreover, a blocked isocyanate compound obtained by blocking one of these isocyanate compounds using one or more blocking agents selected from the group consisting of conventional active methylene-based blocking agents, conventional oxime-based blocking agents, conventional amine-based blocking agents and conventional pyrazole blocking agents may also be used.

Among the various possibilities, from the viewpoints of ease of industrial availability, low-temperature curability and the coating material storage properties, the other crosslinking agent is preferably a melamine compound or a (blocked) isocyanate compound.

<<Resin Composition>>

The curing agent composition described above can be combined with a compound having a carboxyl group as the main component to form a resin composition.

In other words, in one embodiment, the present invention provides a resin composition containing the curing agent composition described above and a compound having a carboxyl group.

Because the resin composition of an embodiment of the present invention contains the compound described above as the curing agent component, the storage stability is favorable.

Examples of the compound having a carboxyl group include polyesters having a carboxyl group, polyamides having a carboxyl group, polyurethanes having a carboxyl group, acrylics having a carboxyl group, and polyolefins having a carboxyl group and the like. Examples of the polyolefin that constitutes the polyolefin having a carboxyl group include polypropylene, polyethylene, polypropylene-polyethylene (random or block) copolymers, and polyolefins having other repeating units of 4 or more carbon atoms.

One of these compounds having a carboxyl group may be used alone, or a combination of two or more such compounds may be used.

Further, in the resin composition of an embodiment of the present invention, the compound having a carboxyl group may be used in the form of a main agent composition that is a mixture with another component.

In the resin composition of an embodiment of the present invention, the lower limit for the molar equivalence ratio of carbodiimide groups in the compound described above relative to carboxyl groups of the above compound having a carboxyl group (carbodiimide groups/carboxyl groups) is typically 0.1, preferably 0.2, and more preferably 0.5. On the other hand, the upper limit for carbodiimide groups/carboxyl groups is typically 5.0, preferably 2.0, and more preferably 1.5.

In other words, the ratio of carbodiimide groups/carboxyl groups is typically at least 0.1 but not more than 5.0, preferably at least 0.2 but not more than 2.0, and more preferably at least 0.5 but not more than 1.5.

By ensuring that the ratio of carbodiimide groups/carboxyl groups falls within the above range, the water resistance of the obtained resin cured product is superior, and the crosslinking density also tends to be higher.

The resin composition of an embodiment of the present invention may, if necessary, also contain additives such as epoxy resins, catalysts, coating improvers, leveling agents, antifoaming agents, stabilizers such as antioxidants and ultraviolet absorbers, plasticizers, surfactants, pigments, fillers, organic or inorganic microparticles, antifungal agents, and silane coupling agents. The blend amounts of these additives may be determined appropriately in accordance with the intended purpose and application.

<Usage Applications>

The resin composition of an embodiment of the present invention can be used favorably in various fields, including coating materials, adhesive materials (adhesives), pressure-sensitive adhesive materials (pressure-sensitive adhesives), inks, sealants, molding materials, foams, optical materials, and resin modifiers for modifying resins such as polyesters, polylactic acid resins, polyamides and polyimides.

Examples of the coating materials include coating materials for plastics, exterior coating materials for automobiles, interior coating materials for automobiles, coating materials for electrical and electronic materials, coating materials for optical materials, coating materials for building materials, glass coating materials, woodwork coating materials, film coating materials, resins for inks, coating materials (coating agents) for artificial and synthetic leathers, coating materials (coating agents) for cans, and paper coating materials. Examples of the optical materials include lenses and the like.

In other words, in one embodiment, the present invention provides a coating material composition containing the resin composition described above.

Examples of the plastic coating materials include coating materials for molded articles that use plastic materials, with more specific examples including coating materials for casings, coating materials for automobile components, coating materials for household electrical appliances, coating materials for robotic materials, coating materials for furniture, coating materials for stationery, coating materials for molded articles formed from flexible materials, coating materials for eyewear materials, and coating materials (surface coating agents) for optical lenses of electronic equipment. Examples of the plastic materials include all manner of polymer materials such as polyolefins, ABS, polycarbonates, polyamides, polyesters, and composites of these plastics. Examples of the casings include casings for mobile phones, smart phones, computers and tablets. Examples of the automobile components include automobile interior materials and head lamps and the like. Examples of the flexible materials include rubbers, elastomers and gels. Examples of the eyewear materials include lenses and the like.

Further, examples of the exterior coating materials for automobiles include coating materials for new vehicles, coating materials for automobile repair, and coating materials for exterior components. Examples of the coating materials for new vehicles and the coating materials for automobile repair include intermediate coating materials, base coating materials and top coating materials. Examples of the exterior components include aluminum wheels and bumpers. In those cases where the resin composition described above is used as an exterior coating material for an automobile, a water-based resin having a carboxyl group or an oil-based resin having a carboxyl group may be used as the main agent, but the use of a water-based resin having a carboxyl group is preferred.

Examples of preferred water-based resins having a carboxyl group include hydrophilic acrylic resins having a carboxyl group, hydrophilic polyurethane resins having a carboxyl group, and hydrophilic polyester resins having a carboxyl group. Among these, a hydrophilic acrylic resin having a carboxyl group or a hydrophilic polyester resin having a carboxyl group is preferred. One of these water-based resins having a carboxyl group may be used alone, or a combination of two or more such resins may be used.

Examples of the film coating materials include coating materials for optical members, coating materials for optical purposes, fiber coating materials, coating materials for electronic and electrical materials, coating materials for food packaging, coating materials for medical films, coating materials for cosmetics packaging, coating materials for decorative films, and coating materials for release films. Examples of the optical members include optical films and optical sheets and the like.

Examples of the resins for inks include vehicles for various types of inks including typographic inks, screen inks, flexo inks, gravure inks, and inkjet inks.

Examples of the adhesives include adhesives for packaging materials, adhesive for electrical equipment, adhesives for liquid crystal displays (LCD), adhesives for organic EL displays, adhesives for organic EL illumination, adhesives for display devices, adhesives for LEDs, adhesives for interior and exterior automobile components, adhesives for household electrical appliances, adhesives for solar cell back sheets, and adhesives for various batteries. Examples of the display devices include electronic papers and plasma displays and the like. Examples of the various batteries include alkaline manganese batteries and lithium ion batteries.

Furthermore, applications of the resin composition are not limited to those described above, and for example, the resin composition may be added as a solid to polyester-based resins, polyamide-based resins and polylactic acids. Alternatively, the resin composition may be used in liquid form as a hydrolysis inhibitor for polyester polyols and the like. Alternatively, the resin composition may be combined with acid-modified polyolefins such as maleic acid-modified polyolefins, or may be added to polyolefin-based emulsions obtained by water dispersion of an acid-modified polyolefin. Alternatively, the resin composition may be combined with acrylic emulsions containing an acid site, or may be used as a curing agent for these acrylic emulsions. Alternatively, the resin composition may be used as a sizing material for various fibers such as carbon fiber and glass fiber, and may be used as a reinforcing material, sizing material or curing agent in fiber reinforced plastics such as carbon fiber reinforced plastics (CFRP). The resin composition of an embodiment of the present invention is ideal for these applications.

<<Resin Cured Product>>

A resin cured product can be obtained by curing the resin composition described above (or the coating material composition described above).

In other words, in one embodiment, the present invention provides a resin cured product obtained by curing the above resin composition (or the above coating material composition). The resin cured product of this embodiment has favorable weather resistance and water resistance.

There are no particular limitations on the method used for producing the resin cured product, and for example in those cases where the resin composition is a single liquid composition, a method may be used in which the resin composition is simply applied, as is, to the coating target object or adherend. Further, in those cases where the resin composition is a two liquid composition, one possible method involves mixing the curing agent composition described above with a compound having a carboxyl group and any other additives that are necessary, and then applying the thus obtained resin composition to the coating target object or adherend. By subsequently heat curing the resin composition applied to the coating target object or adherend, a resin cured product can be obtained.

The upper limit for the curing temperature for the resin composition is, for example, 140° C., and is preferably 100° C., and more preferably 80° C. On the other hand, the lower limit for the curing temperature is, for example, 20° C., and is preferably 30° C., and more preferably 40° C.

In other words, the curing temperature for the resin composition is typically at least 20° C. but not more than 140° C., preferably at least 30° C. but not more than 100° C., and more preferably at least 40° C. but not more than 80° C.

Examples of the method used for applying the resin composition include roll coating, curtain flow coating, spray coating, bell coating, and electrostatic coating methods.

EXAMPLES

Embodiments of the present invention are described below in further detail using specific examples, but embodiments of the present invention are in no way limited by the following examples, provided they do not exceed the scope of the present invention.

Reference Example 1-1, Examples 1-1 to 1-4

Reference Example 1-1

An SUS316 stirred tank with an internal capacity of 1 L was charged with 300 g of xylene and 500 g of an isocyanate compound, and the mixture was heated to 140° C. Subsequently, 1 g of 1-phenyl-2-phospholene-1-oxide was added to the tank and stirred for 5 hours. The xylene and any excess isocyanate compound were removed by distillation to obtain a polycarbodiimide.

Example 1-1

Using hexamethylene diisocyanate as the isocyanate compound, a carbodiimide compound was produced using the same method as Reference Example 1-1. Subsequently, the obtained carbodiimide compound and phenyl isocyanate were mixed such that the stoichiometric ratio of the isocyanate group of the phenyl isocyanate relative to the carbodiimide group of the carbodiimide compound was 1.05-fold, and the mixture was then heated at 80° C. for 5 hours. Analysis of the reaction product revealed that a compound represented by formula (E-1) shown below had been produced.

[Chemical formula 87]

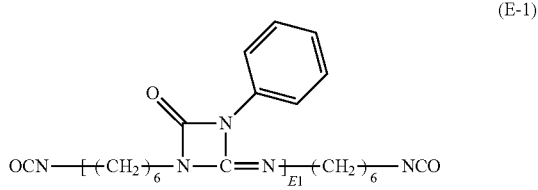

(E-1)

In formula (E-1), the average degree of polymerization E1 was 10.

Example 1-2

Using diphenylmethane diisocyanate as the isocyanate compound, a carbodiimide compound was produced using the same method as Reference Example 1-1. Subsequently, the obtained carbodiimide compound and cyclohexyl isocyanate were mixed such that the stoichiometric ratio of the isocyanate group of the cyclohexyl isocyanate relative to the carbodiimide group of the carbodiimide compound was 1.05-fold, and the mixture was then heated at 80° C. for 5 hours. Analysis of the reaction product revealed that a compound represented by formula (E-2) shown below had been produced.

[Chemical formula 88]

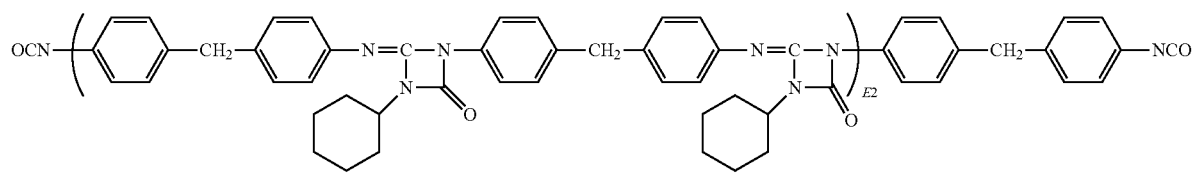

(E-2)

In formula (E-2), the average degree of polymerization E2 was 3.

Example 1-3

Using dicyclohexylmethane diisocyanate as the isocyanate compound, a carbodiimide compound was produced using the same method as Reference Example 1-1. Subsequently, the obtained carbodiimide compound and methyl 2-isocyanato-4-methylvalerate were mixed such that the stoichiometric ratio of the isocyanate group of the methyl 2-isocyanato-4-methylvalerate relative to the carbodiimide group of the carbodiimide compound was 1.05-fold, and the mixture was then heated at 80° C. for 5 hours. Analysis of the reaction product revealed that a compound represented by formula (E-3) shown below had been produced.

[Chemical formula 89]

(E-3)

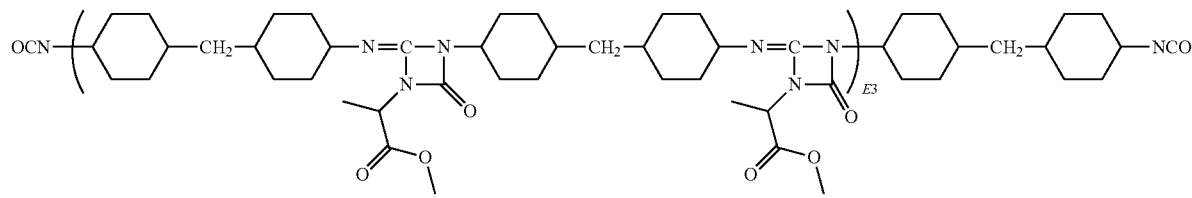

In formula (E-3), the average degree of polymerization E3 was 8.

Example 1-4

Using hydrogenated xylylene diisocyanate as the isocyanate compound, a carbodiimide compound was produced using the same method as Reference Example 1-1. Subsequently, the obtained carbodiimide compound and 1,8-diisocyanato-4-isocyanatomethyloctane were mixed such that the stoichiometric ratio of the isocyanate groups of the 1,8-diisocyanato-4-isocyanatomethyloctane relative to the carbodiimide group of the carbodiimide compound was 3.15-fold, toluene was then added to adjust the substrate concentration to 5% by mass, and the mixture was then heated at 80° C. for 5 hours. Analysis of the reaction product revealed that a compound represented by general formula (E-4) shown below had been produced.

[Chemical formula 90]

(E-4)

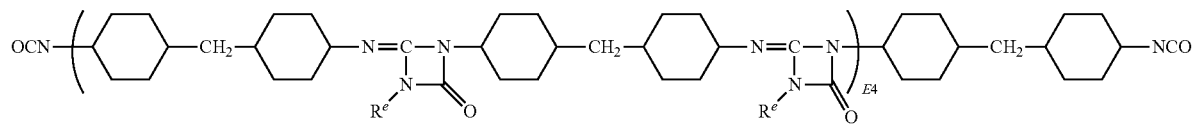

In general formula (E-4), $R^e$ represents a residue obtained by removing one isocyanate group from 1,8-diisocyanato-4-isocyanatomethyloctane (namely, a group represented by formula (E-4-1) shown below, a group represented by formula (E-4-2) shown below, or a group represented by formula (E-4-3) shown below), and the average degree of polymerization E4 was 4.

[Chemical formula 91]

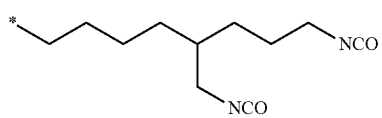
(E-4-1)

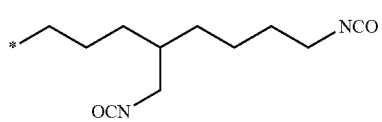
(E-4-2)

-continued

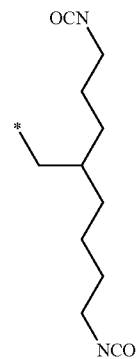
(E-4-3)

(In formulas (E-4-1) to (E-4-3), each asterisk represents a bonding site.)

Examples 2-1 to 2-45, and Comparative Example 2-1

<Evaluation Method>

[Evaluation 2-1] Storage Stability of Resin Composition

Evaluations of the compounds obtained in the examples and comparative example were conducted using the method described below.

Specifically, 1 g of each of the compounds obtained in the examples and comparative example was first dispersed in 10 g of water, and 15 g of an acrylic polyol (SETAQUA 6515 manufactured by Allnex Group) was added and stirred to form a uniform solution (resin composition). This uniform solution (resin composition) was stored at 40° C. for 10 days, and the contents were then inspected visually. The storage stability was evaluated against the following evaluation criteria.

(Evaluation Criteria)

Good: no gelling occurred

Poor: gelling occurred

<Production of Uretonimine Group-Containing Compounds>

Example 2-1

(Step 1)

Dicyclohexylmethane diisocyanate was used as the diisocyanate (hereafter sometimes referred to as "diisocyanate A") for producing a carbodiimide compound. An SUS316 stirred tank with an internal capacity of 1 L was charged with 300 g of xylene and 500 g of the diisocyanate A, and the mixture was heated to 140° C. Subsequently, 1 g of 1-phenyl-2-phospholene-1-oxide was added to the tank and stirred for 5 hours. The obtained reaction liquid was supplied to a thin-film evaporator, the interior of which had been heated to 180° C. and evacuated to a pressure of 0.1 kPa (absolute pressure), thereby removing the xylene and excess isocyanate compound by evaporation to obtain a carbodiimide compound. The average degree of polymerization of the obtained carbodiimide compound was 5. Subsequently, using phenyl isocyanate as the isocyanate compound (hereafter sometimes referred to as "isocyanate compound B") to be reacted with the carbodiimide compound, the carbodiimide compound and the isocyanate compound B were mixed so as to achieve a stoichiometric ratio of the isocyanate group of the isocyanate compound B relative to the carbodiimide group of the carbodiimide compound was 1.05-fold, and the mixture was then heated at 80° C. for 5 hours. Analysis of the reaction product by infrared spectroscopy confirmed absorption near 1720 cm$^{-1}$ attributable to the stretching vibration of uretonimine groups and urethane groups.

(Step 2)

Subsequently, 700 g of a poly(oxyethylene-oxypropylene) glycol monobutyl ether (number average molecular weight: 300, a compound represented by formula (IV-2) shown below (hereafter sometimes referred to as "compound (IV-2)") was added as a compound having a hydrophilic group (hereafter sometimes referred to as the "hydrophilic group-containing compound") to the reaction product obtained above in step 1, and the mixture was heated under stirring at 120° C. for 2 hours. The obtained compound was a compound which, in an infrared spectroscopy spectrum, exhibited a value for the absorbance x near 2020 cm$^{-1}$ attributable to the stretching vibration of carbodiimide groups relative to the absorbance y near 1720 cm$^{-1}$ attributable to the stretching vibration of uretonimine groups and urethane groups, namely a value represented by x/y, of 0.5. Further, evaluation of the resin composition storage stability for the obtained compound using the evaluation method described above yielded a good result.

[Chemical formula 92]

$$C_4H_9-O-(CH_2CH_2O)_{n422}-(CH_2-\underset{CH_3}{\underset{|}{CH}}-O)_{n421}-H \quad (IV-2)$$

(In general formula (IV-2), the ratio of n421 relative to n422 is 1.)

Examples 2-2 to 2-45 and Comparative Example 2-1

With the exceptions of using the combinations of the diisocyanate A, the isocyanate compound B and the hydrophilic group-containing compound shown below in Tables 1 to 4, the same method as that described for Example 2-1 was used to produce compounds, and then evaluate the storage stability when used as resin compositions. The results are shown below in Tables 1 to 4. In Tables 1 to 4, the abbreviations used for the hydrophilic group-containing compounds represent the compounds described below. Further, for the compound (IV-2), compounds having different number average molecular weights of 300, 510 and 1800 (compounds having different degrees of polymerization) were used as appropriate. Further, for the compound (IV-2), random copolymers having number average molecular weights of 300 and 500 were also used as appropriate.

(Hydrophilic Group-Containing Compounds)

MPEG220: polyethylene glycol monomethyl ether (number average molecular weight: 220)

MPEG400: polyethylene glycol monomethyl ether (number average molecular weight: 400)

MPEG550: polyethylene glycol monomethyl ether (number average molecular weight: 550)

TABLE 1

| | Diisocyanate A | Isocyanate compound B | Hydrophilic group-containing compound | x/y | Storage stability of resin composition |
|---|---|---|---|---|---|
| Example 2-1 | OCN—⬡—CH$_2$—⬡—NCO<br>Compound (III-5)-1 | ⬡—NCO | Compound (IV-2)<br>Number average molecular weight: 300<br>Ratio of n421 to n422<br>(n421/n422):1 | 0.5 | good |
| Example 2-2 | OCN—⬡—CH$_2$—⬡—NCO<br>Compound (III-6)-1 | ⬡—NCO | Compound (IV-2)<br>Number average molecular weight: 300<br>Ratio of n421 to n422<br>(n421/n422):1 | 1.0 | good |

TABLE 1-continued

| | Diisocyanate A | Isocyanate compound B | Hydrophilic group-containing compound | x/y | Storage stability of resin composition |
|---|---|---|---|---|---|
| Example 2-3 | 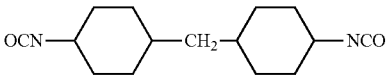<br>Compound (III-5)-1 | OCN−(CH$_2$)$_5$−CH$_3$<br><br>Pentamethylene diisocyanate (PDI) | MPEG220 | 0 | good |
| Example 2-4 | 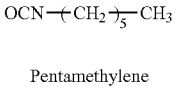<br>Compound (III-5)-1 | OCN−(CH$_2$)$_6$−NCO<br><br>HDI | MPEG550 | 0 | good |
| Example 2-5 | 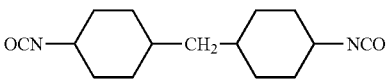<br>Compound (III-4)-1 | 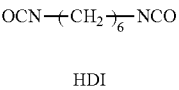 | MPEG400 | 0.5 | good |
| Example 2-6 | 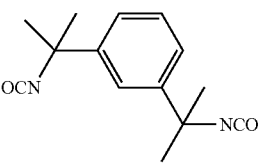<br>Compound (III-4)-1 | OCN−(CH$_2$)$_6$−NCO<br><br>HDI | Compound (IV-2)<br>Number average molecular weight: 510<br>Ratio of n421 to n422 (n421/n422):1 | 0 | good |
| Example 2-7 | 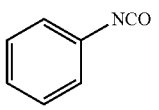<br>Compound (III-2)-1 | 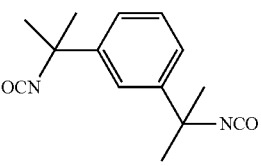 | Diethylene glycol monomethyl ether | 0.1 | good |
| Example 2-8 | 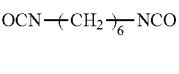<br>Compound (III-6)-1 | 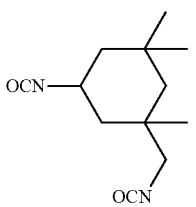 | Triethylene glycol monomethyl ether | 0.5 | good |
| Example 2-9 | 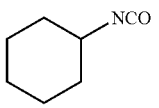<br>Compound (III-6)-1 | 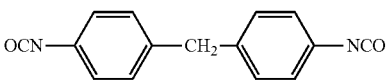 | Compound (IV-2)<br>Number average molecular weight: 300<br>Ratio of n421 to n422 (n421/n422):1 | 1.4 | good |
| Example 2-10 | 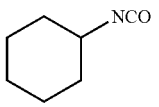<br>Compound (III-5)-1 | 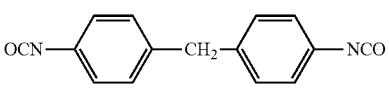 | Compound (IV-2)<br>Number average molecular weight: 300<br>Ratio of n421 to n422 (n421/n422):1 | | |

TABLE 1-continued

| | Diisocyanate A | Isocyanate compound B | Hydrophilic group-containing compound | x/y | Storage stability of resin composition |
|---|---|---|---|---|---|
| Example 2-11 | Compound (III-5)-1 | (methyl ester of leucine isocyanate) | MPEG550 | 0 | good |
| Example 2-12 | Compound (III-5)-1 | (ethyl ester of isoleucine isocyanate) | Diethylene glycol monomethyl ether | 0.1 | good |
| Example 2-13 | Compound (III-5)-1 | (ethyl propyl glutamate isocyanate) | Triethylene glycol monomethyl ether | 0.2 | good |

TABLE 2

| | Diisocyanate A | Isocyanate compound B | Hydrophilic group-containing compound | x/y | Storage stability of resin composition |
|---|---|---|---|---|---|
| Example 2-14 | Compound (III-5)-1 | Nonane triisocyanate (NTI) | Triethylene glycol monomethyl ether | 0.2 | good |
| Example 2-15 | Compound (III-5)-1 | Lysine triisocyanate (LTI) | MPEG400 | 0 | good |
| Example 2-16 | Compound (III-5)-1 | (lysine-derived triisocyanate, ethyl ester) | Compound (IV-2) Number average molecular weight: 1800 Ratio of n421 to n422 (n421/n422):1 | 0 | good |
| Example 2-17 | Compound (III-5)-1 | Compound (III-2)-1 | MPEG550 | 0.3 | good |

TABLE 2-continued

| | Diisocyanate A | Isocyanate compound B | Hydrophilic group-containing compound | x/y | Storage stability of resin composition |
|---|---|---|---|---|---|
| Example 2-18 | Compound (III-5)-1 | Compound (III-6)-1 | Triethylene glycol monomethyl ether | 0.2 | good |
| Example 2-19 | Compound (III-6)-1 | (ethyl isocyanatoacetate) | MPEG550 | 0.3 | good |
| Example 2-20 | Compound (III-6)-1 | (methyl 2-isocyanato-4-methylpentanoate) | Compound (IV-2) Number average molecular weight: 300 Ratio of n421 to n422 (n421/n422):1 | 0 | good |
| Example 2-21 | Compound (III-6)-1 | (ethyl 2-isocyanato-3-methylpentanoate) | MPEG220 | 0 | good |
| Example 2-22 | Compound (III-6)-1 | (1-ethyl 5-propyl 2-isocyanatoglutarate) | MPEG400 | 0.3 | good |
| Example 2-23 | Compound (III-6)-1 | NTI | Triethylene glycol monomethyl ether | 0.5 | good |
| Example 2-24 | Compound (III-6)-1 | LTI | Diethylene glycol monomethyl ether | 0.1 | good |
| Example 2-25 | Compound (III-6)-1 | | Compound (IV-2) Number average molecular weight: 510 Ratio of n421 to n422 (n421/n422):1 | 0 | good |
| Example 2-26 | Compound (III-2)-1 | Compound (III-6)-1 | MPEG220 | 0 | good |

TABLE 3

| | Diisocyanate A | Isocyanate compound B | Hydrophilic group-containing compound | x/y | Storage stability of resin composition |
|---|---|---|---|---|---|
| Example 2-27 | 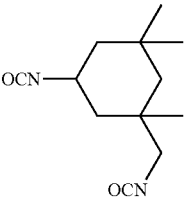<br>Compound (III-2)-1 | 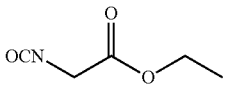 | Diethylene glycol monomethyl ether | 0.1 | good |
| Example 2-28 | 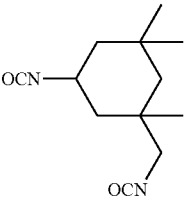<br>Compound (III-2)-1 | 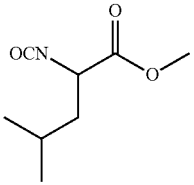 | MPEG550 | 0.3 | good |
| Example 2-29 | 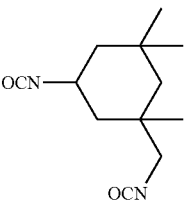<br>Compound (III-2)-1 | 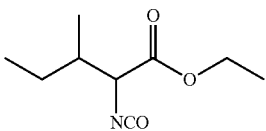 | Compound (IV-2) Number average molecular weight: 1800 Ratio of n421 to n422 (n421/n422):1 | 0 | good |
| Example 2-30 | 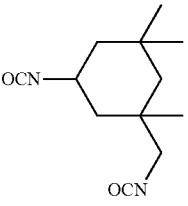<br>Compound (III-2)-1 | 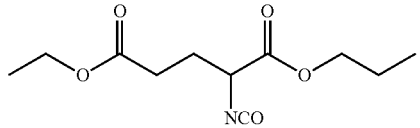 | Compound (IV-2) Number average molecular weight: 300 Ratio of n421 to n422 (n421/n422):1 | 0 | good |
| Example 2-31 | 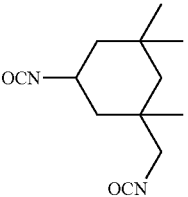<br>Compound (III-2)-1 | 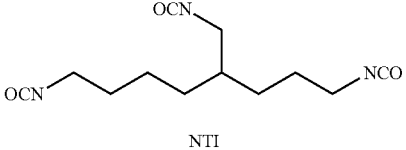<br>NTI | Triethylene glycol monomethyl ether | 0.5 | good |
| Example 2-32 | 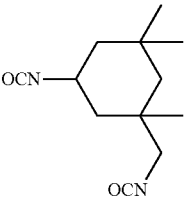<br>Compound (III-2)-1 | 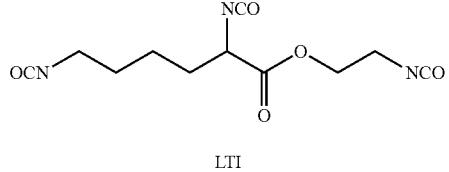<br>LTI | MPEG400 | 0.3 | good |

TABLE 3-continued

| | Diisocyanate A | Isocyanate compound B | Hydrophilic group-containing compound | x/y | Storage stability of resin composition |
|---|---|---|---|---|---|
| Example 2-33 | Compound (III-2)-1 (isophorone diisocyanate structure) | Ethyl 2-isocyanato-6-isocyanatohexanoate (NCO, OCN-...-C(=O)O-ethyl) | Triethylene glycol monomethyl ether | 0.5 | good |
| Example 2-34 | Molar ratio Compound (III-2)-1 : Compound (III-5)-1 = 1:1 | Phenyl isocyanate | Compound (IV-2) Number average molecular weight: 1800 Ratio of n421 to n422 (n421/n422):1 | 0.3 | good |
| Example 2-35 | Molar ratio Compound (III-2)-1 : Compound (III-5)-1 = 1:1 | OCN-C$_6$H$_4$-CH$_2$-C$_6$H$_4$-NCO Compound (III-6)-1 | MPEG220 | 0.1 | good |
| Example 2-36 | Molar ratio Compound (III-5)-1 : Compound (III-6)-1 = 1:1 | NTI (triisocyanate) | Compound (IV-2) Number average molecular weight: 510 Ratio of n421 to n422 (n421/n422):1 | 0.1 | good |
| Example 2-37 | Molar ratio Compound (III-5)-1 : Compound (III-6)-1 = 1:1 | Ethyl isocyanatoacetate (OCN-CH$_2$-C(=O)O-ethyl) | MPEG550 | 0 | good |
| Example 2-38 | Molar ratio Compound (III-5)-1 : Compound (III-6)-1 = 1:1 | 1,3-bis(isocyanatomethyl)benzene | Compound (IV-2) Number average molecular weight: 300 Ratio of n421 to n422 (n421/n422):1 | 0.1 | good |
| Example 2-39 | Molar ratio Compound (III-5)-1 : Compound (III-6)-1 = 1:1 | Ethyl 2-isocyanato-3-methylpentanoate | Compound (IV-2) Number average molecular weight: 510 Ratio of n421 to n422 (n421/n422):1 | 0.2 | good |

TABLE 4

| | Diisocyanate A | Isocyanate compound B | Hydrophilic group-containing compound | x/y | Storage stability of resin composition |
|---|---|---|---|---|---|
| Example 2-40 | Molar ratio Compound (III-5)-1 : Compound (III-6)-1 = 1:1 | Lysine triisocyanate (LTI) | Triethylene glycol monomethyl ether | 0.1 | good |

TABLE 4-continued

| | Diisocyanate A | Isocyanate compound B | Hydrophilic group-containing compound | x/y | Storage stability of resin composition |
|---|---|---|---|---|---|
| Example 2-41 | Molar ratio Compound (III-4)-1: Compound (III-6)-1 = 1:1 | Compound (III-2)-1 | Compound (IV-2) Number average molecular weight: 300 Ratio of n421 to n422 (n421/n422):1 (random copolymer) | 0 | good |
| Example 2-42 | Molar ratio Compound (III-3)-1: Compound (III-6)-1 = 1:1 | DURANATE TPA-100 (manufactured by Asahi Kasei Corporation) | MPEG550 | 0 | good |
| Example 2-43 | Molar ratio Compound (III-3)-1: Compound (III-4)-1 = 1:1 | Mass ratio HDI: DURANATE TPA-100 (manufactured by Asahi Kasei Corporation) = 0.9:0.1 | Compound (IV-2) Number average molecular weight: 300 Ratio of n421 to n422 (n421/n422):1 | 0 | good |
| Example 2-44 | Molar ratio Compound (III-2)-1: Compound (III-6)-1 = 1:1 | Mass ratio HDI:NTI = 0.9:0.1 | Diethylene glycol monomethyl ether | 0 | good |
| Example 2-45 | Molar ratio Compound (III-2)-1: Compound (III-6)-1 = 1:1 | Mass ratio Compound (III-5)-1: NTI = 0.9:0.1 | Compound (IV-2) Number average molecular weight: 500 Ratio of n421 to n422 (n421/n422):1 (random copolymer) | 0 | good |
| Comparative Example 2-1 | Compound (III-6)-1 | 2,6-xylyl isocyanate | Compound (IV-2) Number average molecular weight: 300 Ratio of n421 to n422 (n421/n422):1 | 2.0 | poor |

Based on Tables 1 to 4, it was evident that whereas the compounds produced in Examples 2-1 to 2-45 all exhibited good storage stability when used as resin compositions, the compound produced in Comparative Example 2-1 exhibited poor storage stability when used as a resin composition.

Examples 3-1 to 3-45 and Comparative Example 3-1

<Evaluation Method>
[Evaluation 3-1] Storage Stability of Resin Composition

Evaluations of the compounds obtained in the examples and comparative example were conducted using the method described below.

Specifically, 1 g of each of the compounds obtained in the examples and comparative example was first dispersed in 10 g of water, and 15 g of an acrylic polyol (SETAQUA 6515 manufactured by Allnex Group) was added and stirred to form a uniform solution (resin composition). This solution (resin composition) was stored at 40° C. for 10 days, and the contents were then inspected visually. The storage stability was evaluated against the following evaluation criteria.

(Evaluation Criteria)
Good: no gelling occurred
Poor: gelling occurred

<Production of Uretonimine Group-Containing Compounds>

Example 3-1

(Step 1)

An SUS316 stirred tank with an internal capacity of 1 L was charged with 300 g of xylene and 500 g of hexamethylene diisocyanate, and the mixture was heated to 140° C. Subsequently, 1 g of 1-phenyl-2-phospholene-1-oxide was added to the tank and stirred for 5 hours. The obtained reaction liquid was supplied to a thin-film evaporator, the interior of which had been heated to 180° C. and evacuated to a pressure of 0.1 kPa (absolute pressure), thereby removing the xylene and excess isocyanate compound by evaporation to obtain a compound. Analysis of the obtained compound by infrared spectroscopy confirmed absorption peaks attributable to an uretonimine group and a carbodiimide group.

(Step 2)

Subsequently, 890 g of a poly(oxyethylene-oxypropylene) glycol monobutyl ether (number average molecular weight: 300, a compound represented by formula (IV-2) shown below (hereafter sometimes referred to as "compound (IV-2)") was added as a compound having a hydrophilic group (hereafter sometimes referred to as the "hydrophilic group-containing compound") to the compound obtained above in step 1, and the mixture was heated under stirring at 150° C. for 8 hours. When the obtained compound was analyzed by $^{13}$C-NMR spectroscopy, no peak was observed at a chemical shift corresponding with an uretonimine group.

[Chemical formula 93]

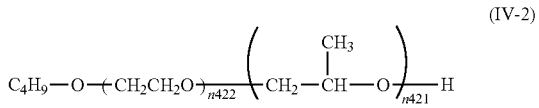

(IV-2)

(In general formula (IV-2), the ratio of n421 relative to n422 is 1.)

(Step 3)

Using phenyl isocyanate as the isocyanate compound (hereafter sometimes referred to as "isocyanate compound B") for reaction with the carbodiimide compound, the isocyanate compound B was mixed with the compound obtained above in step 2 such that the stoichiometric ratio of the isocyanate group of the isocyanate compound B relative to the carbodiimide group of the carbodiimide compound was 1.05-fold, and the mixture was then heated at 80° C. for 5 hours. The obtained compound was a compound which, in an infrared spectroscopy spectrum, exhibited a value for the absorbance x near 2020 cm$^{-1}$ attributable to the stretching vibration of carbodiimide groups relative to the absorbance y near 1720 cm$^{-1}$ attributable to the stretching vibration of uretonimine groups and urethane groups, namely a value represented by x/y, of 0.3. Further, evaluation of the resin composition storage stability for the obtained compound using the evaluation method described above yielded a good result.

Examples 3-2 to 3-45 and Comparative Example 3-1

With the exceptions of using the combinations of the diisocyanate A, the isocyanate compound B and the hydrophilic group-containing compound shown below in Tables 5 to 8, the same method as that described for Example 3-1 was used to produce compounds, and then evaluate the storage stability when used as resin compositions. The results are shown below in Tables 5 to 8. In Tables 5 to 8, the abbreviations used for the hydrophilic group-containing compounds represent the compounds described below. Further, for the compound (IV-2), compounds having different number average molecular weights of 300, 510 and 1800 (compounds having different degrees of polymerization) were used as appropriate. Further, for the compound (IV-2), random copolymers having number average molecular weights of 300 and 500 were also used as appropriate.

(Hydrophilic Group-Containing Compounds)

MPEG220: polyethylene glycol monomethyl ether (number average molecular weight: 220)

MPEG400: polyethylene glycol monomethyl ether (number average molecular weight: 400)

MPEG550: polyethylene glycol monomethyl ether (number average molecular weight: 550)

TABLE 5

| | Diisocyanate A | Isocyanate compound B | Hydrophilic group-containing compound | x/y | Storage stability of resin composition |
|---|---|---|---|---|---|
| Example 3-1 | OCN—(CH$_2$)$_6$—NCO<br><br>Hexamethylene diisocyanate (HDI) | phenyl-NCO | Compound (IV-2)<br>Number average molecular weight: 300<br>Ratio of n421 to n422 (n421/n422):1 | 0.3 | good |
| Example 3-2 | OCN-CH$_2$-(m-phenylene)-CH$_2$-NCO<br><br>Compound (VI-3)-1 | phenyl-NCO | Compound (IV-2)<br>Number average molecular weight: 300<br>Ratio of n421 to n422 (n421/n422):1 | 0.8 | good |
| Example 3-3 | OCN—(CH$_2$)$_6$—NCO<br><br>HDI | isophorone diisocyanate structure (OCN-cyclohexyl-CH$_2$-NCO with methyl substituents) | MPEG220 | 0 | good |
| Example 3-4 | OCN—(CH$_2$)$_6$—NCO<br><br>HDI | OCN-CH$_2$-(m-phenylene)-CH$_2$-NCO | MPEG550 | 0 | good |

TABLE 5-continued

| | Diisocyanate A | Isocyanate compound B | Hydrophilic group-containing compound | x/y | Storage stability of resin composition |
|---|---|---|---|---|---|
| Example 3-5 | OCN—(CH$_2$)$_4$—NCO<br>Tetramethylene diisocyanate | Phenyl-NCO | MPEG400 | 0.1 | good |
| Example 3-6 | OCN—(CH$_2$)$_4$—NCO<br>Tetramethylene diisocyanate | OCN-CH$_2$-cyclohexyl-CH$_2$-NCO | Compound (IV-2)<br>Number average molecular weight: 510<br>Ratio of n421 to n422 (n421/n422):1 | 0 | good |
| Example 3-7 | OCN-CH$_2$-cyclohexyl-CH$_2$-NCO<br>Compound (VI-2)-1 | Cyclohexyl-NCO | Diethylene glycol monomethyl ether | 0.1 | good |
| Example 3-8 | OCN-CH$_2$-(m-phenylene)-CH$_2$-NCO<br>Compound (VI-3)-1 | Cyclohexyl-NCO | Triethylene glycol monomethyl ether | 0.2 | good |
| Example 3-9 | OCN-CH$_2$-(m-phenylene)-CH$_2$-NCO<br>Compound (VI-3)-1 | Phenyl-NCO | Compound (IV-2)<br>Number average molecular weight: 300<br>Ratio of n421 to n422 (n421/n422):1 | 0.5 | good |
| Example 3-10 | OCN—(CH$_2$)$_6$—NCO<br>HDI | OCN-CH$_2$-C(=O)-O-ethyl | Compound (IV-2)<br>Number average molecular weight: 300<br>Ratio of n421 to n422 (n421/n422):1 | 0 | good |
| Example 3-11 | OCN—(CH$_2$)$_6$—NCO<br>HDI | OCN-CH(CH$_2$CH(CH$_3$)$_2$)-C(=O)-O-methyl | MPEG550 | 0 | good |
| Example 3-12 | OCN—(CH$_2$)$_6$—NCO<br>HDI | ethyl-CH(CH$_3$)-CH(NCO)-C(=O)-O-ethyl | Diethylene glycol monomethyl ether | 0 | good |
| Example 3-13 | OCN—(CH$_2$)$_6$—NCO<br>HDI | ethyl-O-C(=O)-CH$_2$-CH$_2$-CH(NCO)-C(=O)-O-propyl | Triethylene glycol monomethyl ether | 0.3 | good |

TABLE 6

| | Diisocyanate A | Isocyanate compound B | Hydrophilic group-containing compound | x/y | Storage stability of resin composition |
|---|---|---|---|---|---|
| Example 3-14 | OCN—(CH₂)₆—NCO<br>HDI | 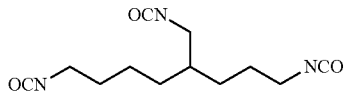<br>Nonane triisocyanate (NTI) | Triethylene glycol monomethyl ether | 0.2 | good |
| Example 3-15 | OCN—(CH₂)₆—NCO<br>HDI | 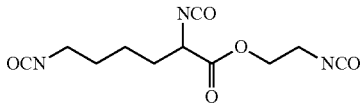<br>Lysine triisocyanate (LTI) | MPEG400 | 0 | good |
| Example 3-16 | OCN—(CH₂)₆—NCO<br>HDI | 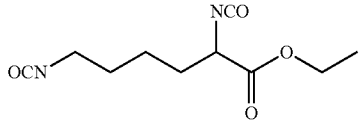 | Compound (IV-2)<br>Number average molecular weight: 1800<br>Ratio of n421 to n422 (n421/n422):1 | 0 | good |
| Example 3-17 | OCN—(CH₂)₆—NCO<br>HDI | 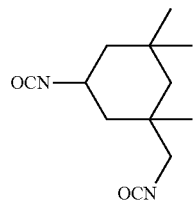 | MPEG550 | 0.3 | good |
| Example 3-18 | OCN—(CH₂)₆—NCO<br>HDI | 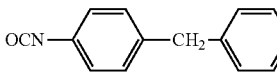<br>Diphenylmethane-4,4'-diisocyanate (MDI) | Triethylene glycol monomethyl ether | 0.2 | good |
| Example 3-19 | 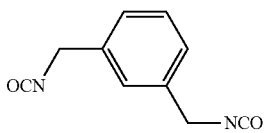<br>Compound (VI-3)-1 | 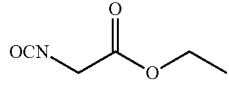 | MPEG550 | 0.2 | good |
| Example 3-20 | 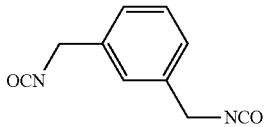<br>Compound (VI-3)-1 | 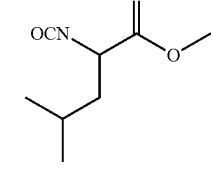 | Compound (IV-2)<br>Number average molecular weight: 300<br>Ratio of n421 to n422 (n421/n422):1 | 0 | good |
| Example 3-21 | 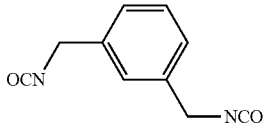<br>Compound (VI-3)-1 | 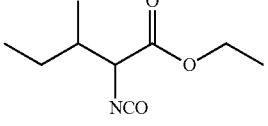 | MPEG220 | 0 | good |

TABLE 6-continued

| | Diisocyanate A | Isocyanate compound B | Hydrophilic group-containing compound | x/y | Storage stability of resin composition |
|---|---|---|---|---|---|
| Example 3-22 | 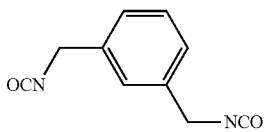<br>Compound (VI-3)-1 | 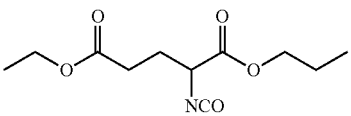 | MPEG400 | 0.3 | good |
| Example 3-23 | 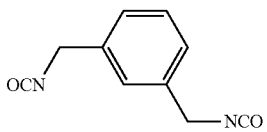<br>Compound (VI-3)-1 | 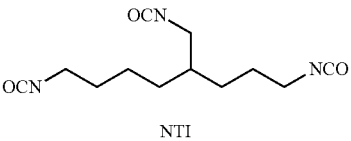<br>NTI | Triethylene glycol monomethyl ether | 0.5 | good |
| Example 3-24 | 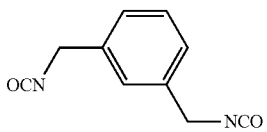<br>Compound (VI-3)-1 | 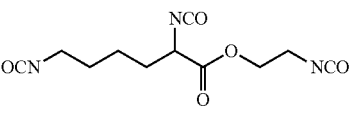<br>LTI | Diethylene glycol monomethyl ether | 0.3 | good |
| Example 3-25 | 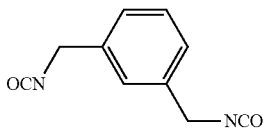<br>Compound (VI-3)-1 | 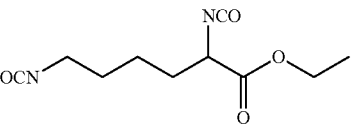 | Compound (IV-2) Number average molecular weight: 510 Ratio of n421 to n422 (n421/n422):1 | 0 | good |
| Example 3-26 | 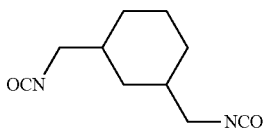<br>Compound (VI-2)-1 | 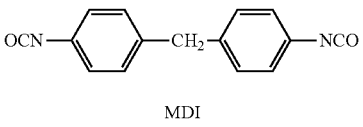<br>MDI | MPEG220 | 0 | good |

TABLE 7

| | Diisocyanate A | Isocyanate compound B | Hydrophilic group-containing compound | x/y | Storage stability of resin composition |
|---|---|---|---|---|---|
| Example 3-27 | 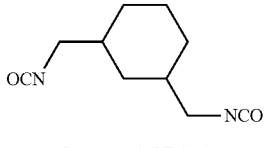<br>Compound (VI-2)-1 | 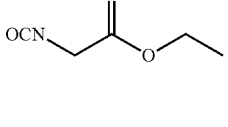 | Diethylene glycol monomethyl ether | 0.1 | good |
| Example 3-28 | 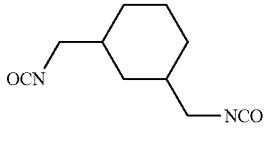<br>Compound (VI-2)-1 | 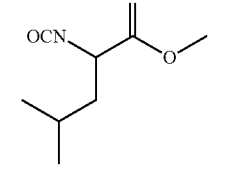 | MPEG550 | 0.4 | good |

TABLE 7-continued

| | Diisocyanate A | Isocyanate compound B | Hydrophilic group-containing compound | x/y | Storage stability of resin composition |
|---|---|---|---|---|---|
| Example 3-29 | Compound (VI-2)-1 | (structure with NCO, ester) | Compound (IV-2) Number average molecular weight: 1800 Ratio of n421 to n422 (n421/n422):1 | 0 | good |
| Example 3-30 | Compound (VI-2)-1 | (diester structure with NCO) | Compound (IV-2) Number average molecular weight: 300 Ratio of n421 to n422 (n421/n422):1 | 0 | good |
| Example 3-31 | Compound (VI-2)-1 | NTI | Triethylene glycol monomethyl ether | 0.3 | good |
| Example 3-32 | Compound (VI-2)-1 | LTI | MPEG400 | 0.3 | good |
| Example 3-33 | Compound (VI-2)-1 | (structure with NCO, ester) | Compound (IV-2) Number average molecular weight: 300 Ratio of n421 to n422 (n421/n422):1 | 0.4 | good |
| Example 3-34 | Molar ratio pentamethylene diisocyanate: HDI = 1:1 | (phenyl NCO) | Compound (IV-2) Number average molecular weight: 1800 Ratio of n421 to n422 (n421/n422):1 | 0.3 | good |
| Example 3-35 | Molar ratio pentamethylene diisocyanate: HDI = 1:1 | MDI | MPEG220 | 0.1 | good |
| Example 3-36 | Molar ratio pentamethylene diisocyanate: HDI = 1:1 | (triisocyanate structure) | Compound (IV-2) Number average molecular weight: 510 Ratio of n421 to n422 (n421/n422):1 | 0.1 | good |
| Example 3-37 | Molar ratio pentamethylene diisocyanate: HDI = 1:1 | (OCN-CH2-C(O)-O-ethyl) | MPEG550 | 0 | good |

TABLE 7-continued

| | Diisocyanate A | Isocyanate compound B | Hydrophilic group-containing compound | x/y | Storage stability of resin composition |
|---|---|---|---|---|---|
| Example 3-38 | Molar ratio Compound (VI-2)-1: HDI = 1:1 | 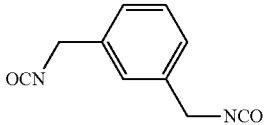 | Compound (IV-2) Number average molecular weight: 300 Ratio of n421 to n422 (n421/n422):1 | 0.1 | good |
| Example 3-39 | Molar ratio Compound (VI-2)-1: HDI = 1:1 | 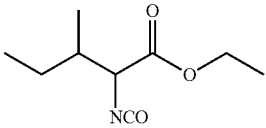 | Compound (IV-2) Number average molecular weight: 1800 Ratio of n421 to n422 (n421/n422):1 | 0.2 | good |

TABLE 8

| | Diisocyanate A | Isocyanate compound B | Hydrophilic group-containing compound | x/y | Storage stability of resin composition |
|---|---|---|---|---|---|
| Example 3-40 | Molar ratio Compound (VI-2)-1 : pentamethylene diisocyanate = 1:1 | 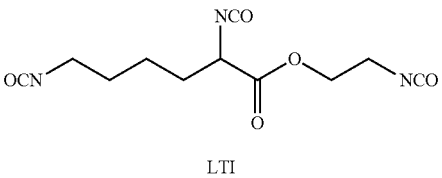<br>LTI | Triethylene glycol monomethyl ether | 0.1 | good |
| Example 3-41 | Molar ratio Compound (VI-2)-1 : pentamethylene diisocyanate = 1:1 | 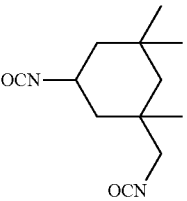 | Compound (IV-2) Number average molecular weight: 300 Ratio of n421 to n422 (n421/n422):1 (random copolymer) | 0 | good |
| Example 3-42 | Molar ratio Compound (VI-2)-1: Compound (VI-3)-1 = 1:1 | DURANATE TPA-100 (manufactured by Asahi Kasei Corporation) | MPEG550 | 0 | good |
| Example 3-43 | Molar ratio Compound (VI-2)-1: Compound (VI-3)-1 = 1:1 | Mass ratio HDI : DURANATE TPA-100 (manufactured by Asahi Kasei Corporation) = 0.9:0.1 | Compound (IV-2) Number average molecular weight: 300 Ratio of n421 to n422 (n421/n422):1 | 0 | good |
| Example 3-44 | Molar ratio Compound (VI-2)-1: Compound (VI-3)-1 = 1:1 | Mass ratio MDI:NTI = 0.9:0.1 | Diethylene glycol monomethyl ether | 0 | good |
| Example 3-45 | Mass ratio Compound (VI-2)-1: DURANATE TPA-100 (manufactured by Asahi Kasei Corporation) = 0.9:0.1 | Mass ratio MDI:NTI = 0.9:0.1 | Compound (IV-2) Number average molecular weight: 500 Ratio of n421 to n422 (n421/n422):1 (random copolymer) | 0 | good |

TABLE 8-continued

| | Diisocyanate A | Isocyanate compound B | Hydrophilic group-containing compound | x/y | Storage stability of resin composition |
|---|---|---|---|---|---|
| Comparative Example 3-1 | Compound (VI-3)-1 (OCN–CH2–C6H4–CH2–NCO) | 2,6-xylyl isocyanate | Compound (IV-2) Number average molecular weight: 300 Ratio of n421 to n422 (n421/n422):1 | 1.7 | poor |

Based on Tables 5 to 8, it was evident that whereas the compounds produced in Examples 3-1 to 3-45 all exhibited good storage stability when used as resin compositions, the compound produced in Comparative Example 3-1 exhibited poor storage stability when used as a resin composition.

Examples 4-1 to 4-24 and Comparative Example 4-1

<Evaluation Method>
[Evaluation 4-1] Storage Stability of Resin Composition
Evaluations of the compounds obtained in the examples and comparative example were conducted using the method described below.

Specifically, 1 g of each of the compounds obtained in the examples and comparative example was first dispersed in 10 g of water, and 15 g of an acrylic polyol (SETAQUA 6515 manufactured by Allnex Group) was added and stirred to form a uniform solution (resin composition). This uniform solution (resin composition) was stored at 40° C. for 10 days, and the contents were then inspected visually. The storage stability was evaluated against the following evaluation criteria.
(Evaluation Criteria)
Good: no gelling occurred
Poor: gelling occurred
<Production of Carbodiimide Compounds>

Example 4-1

(Step 1)
An SUS316 stirred tank with an internal capacity of 1 L was charged with 300 g of xylene and 500 g of hexamethylene diisocyanate, and the mixture was heated to 140° C. Subsequently, 1 g of 1-phenyl-2-phospholene-1-oxide was added to the tank and stirred for 5 hours. The obtained reaction liquid was supplied to a thin-film evaporator, the interior of which had been heated to 180° C. and evacuated to a pressure of 0.1 kPa (absolute pressure), thereby removing the xylene and excess isocyanate compound by evaporation to obtain a compound. Analysis of the obtained compound by infrared spectroscopy confirmed absorption peaks attributable to an uretonimine group and a carbodiimide group.
(Step 2)
Subsequently, 890 g of a poly(oxyethylene-oxypropylene) glycol monobutyl ether (number average molecular weight: 300, a compound represented by formula (IV-2) shown below (hereafter sometimes referred to as "compound (IV-2)") was added as a compound having a hydrophilic group (hereafter sometimes referred to as the "hydrophilic group-containing compound") to the compound obtained above in step 1, and the mixture was heated under stirring at 150° C. for 8 hours. When the obtained compound was analyzed by $^{13}$C-NMR spectroscopy, no peak was observed at a chemical shift corresponding with an uretonimine group.

[Chemical formula 94]

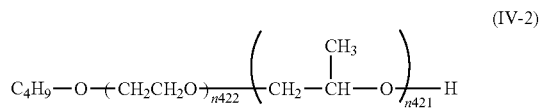

$$C_4H_9-O+(CH_2CH_2O)_{n422}(CH_2-CH(CH_3)-O)_{n421}H \quad (IV-2)$$

(In general formula (IV-2), the ratio of n421 relative to n422 is 1.)

Examples 4-2 to 4-23, and Comparative Example 4-1

With the exceptions of using the combinations of the diisocyanate and the hydrophilic group-containing compound shown below in Tables 9 and 10, the same method as that described for Example 4-1 was used to produce compounds, and then evaluate the storage stability when used as resin compositions. The results are shown below in Tables 9 and 10. In Tables 9 and 10, the abbreviation used for the hydrophilic group-containing compound represents the compounds described below. Further, for the compound (IV-2), compounds having different number average molecular weights of 300, 510 and 1800 (compounds having different degrees of polymerization) were used as appropriate. Further, for the compound (IV-2), random copolymers having number average molecular weights of 300 and 500 were also used as appropriate.
(Hydrophilic Group-Containing Compound)
MPEG400: polyethylene glycol monomethyl ether (number average molecular weight: 400)

Example 4-24

An SUS316 stirred tank with an internal capacity of 1 L was charged with 84.1 g of hydrogenated XDI (the compound (VI-2)-1) and 82.5 g of the compound (IV-2) (number average molecular weight: 300, ratio of n421 to n422 in general formula (IV-2) of 1), the mixture was stirred at 120°

C. for one hour, 13.1 g of 4,4'-diphenylmethane diisocyanate (the compound (III-6)-1) and 1.94 g of 3-methyl-1-phenyl-2-phospholene-1-oxide were added, and the resulting mixture was stirred under a stream of nitrogen at 185° C. for a further 5 hours, thus obtaining a compound. Analysis of the reaction liquid using an infrared spectrometer revealed that the isocyanate group absorption at 2200 $cm^{-1}$ to 2300 $cm^{-1}$ had disappeared.

Further, when the obtained compound was analyzed by $^{13}$C-NMR spectroscopy, no peak was observed at a chemical shift corresponding with an uretonimine group.

TABLE 9

| | Diisocyanate | Hydrophilic group-containing compound | Storage stability of resin composition |
|---|---|---|---|
| Example 4-1 | OCN—(CH$_2$)$_6$—NCO<br><br>Hexamethylene diisocyanate (HDI) | Compound (IV-2)<br>Number average molecular weight: 300<br>Ratio of n421 to n422 (n421/n422):1 | good |
| Example 4-2 | 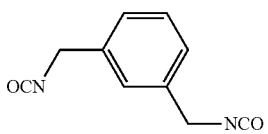<br>Compound (VI-3)-1 | Compound (IV-2)<br>Number average molecular weight: 300<br>Ratio of n421 to n422 (n421/n422):1 | good |
| Example 4-3 | OCN—(CH$_2$)$_4$—NCO<br><br>Tetramethylene diisocyanate | Compound (IV-2)<br>Number average molecular weight: 510<br>Ratio of n421 to n422 (n421/n422):1 | good |
| Example 4-4 | 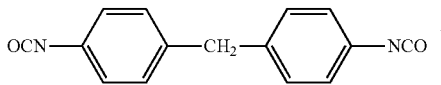<br>Compound (III-6)-1 | Compound (IV-2)<br>Number average molecular weight: 300<br>Ratio of n421 to n422 (n421/n422):1 | good |
| Example 4-5 | 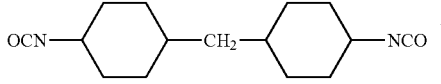<br>Compound (III-5)-1 | Compound (IV-2)<br>Number average molecular weight: 300<br>Ratio of n421 to n422 (n421/n422):1 | good |
| Example 4-6 | 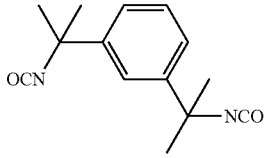<br>Compound (III-4)-1 | Compound (IV-2)<br>Number average molecular weight: 510<br>Ratio of n421 to n422 (n421/n422):1 | good |
| Example 4-7 | 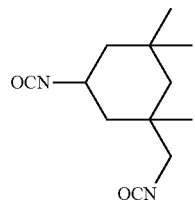<br>Compound (III-2)-1 | Compound (IV-2)<br>Number average molecular weight: 510<br>Ratio of n421 to n422 (n421/n422):1 | good |
| Example 4-8 | OCN—(CH$_2$)$_6$—NCO<br><br>HDI | Compound (IV-2)<br>Number average molecular weight: 1800<br>Ratio of n421 to n422 (n421/n422):1 | good |
| Example 4-9 | 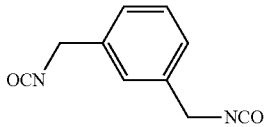<br>Compound (VI-3)-1 | Compound (IV-2)<br>Number average molecular weight: 1800<br>Ratio of n421 to n422 (n421/n422):1 | good |

TABLE 9-continued

| | Diisocyanate | Hydrophilic group-containing compound | Storage stability of resin composition |
|---|---|---|---|
| Example 4-10 | 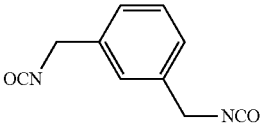<br>Compound (VI-3)-1 | Compound (IV-2)<br>Number average molecular weight: 510<br>Ratio of n421 to n422 (n421/n422):1 | good |
| Example 4-11 | 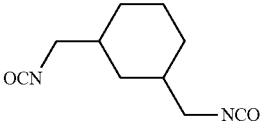<br>Compound (VI-2)-1 | Compound (IV-2)<br>Number average molecular weight: 1800<br>Ratio of n421 to n422 (n421/n422):1 | good |
| Example 4-12 | 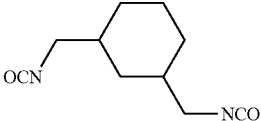<br>Compound (VI-2)-1 | Compound (IV-2)<br>Number average molecular weight: 300<br>Ratio of n421 to n422 (n421/n422):1 | good |

TABLE 10

| | Diisocyanate | Hydrophilic group-containing compound | Storage stability of resin composition |
|---|---|---|---|
| Example 4-13 | Molar ratio<br>pentamethylene diisocyanate:HDI = 1:1 | Compound (IV-2)<br>Number average molecular weight: 300<br>Ratio of n421 to n422 (n421/n422):1 | good |
| Example 4-14 | Molar ratio<br>Compound (VI-3)-1:HDI = 1:1 | Compound (IV-2)<br>Number average molecular weight: 300<br>Ratio of n421 to n422 (n421/n422):1 | good |
| Example 4-15 | Molar ratio<br>Compound (VI-2)-1:Compound (VI-3)-1 = 1:1 | Compound (IV-2)<br>Number average molecular weight: 510<br>Ratio of n421 to n422 (n421/n422):1 | good |
| Example 4-16 | Molar ratio<br>Compound (III-6)-1:Compound (VI-3)-1 = 1:1 | Compound (IV-2)<br>Number average molecular weight: 300<br>Ratio of n421 to n422 (n421/n422):1 | good |
| Example 4-17 | Molar ratio<br>Compound (III-5)-1:Compound (VI-2)-1 = 1:1 | Compound (IV-2)<br>Number average molecular weight: 300<br>Ratio of n421 to n422 (n421/n422):1<br>(random copolymer) | good |
| Example 4-18 | Molar ratio<br>Compound (III-4)-1:Compound (III-6)-1 = 1:1 | Compound (IV-2)<br>Number average molecular weight: 500<br>Ratio of n421 to n422 (n421/n422):1<br>(random copolymer) | good |
| Example 4-19 | Molar ratio<br>Compound (III-2)-1: HDI = 1:1 | Compound (IV-2)<br>Number average molecular weight: 510<br>Ratio of n421 to n422 (n421/n422):1 | good |
| Example 4-20 | Mass ratio<br>DURANATE TPA-100 (manufactured by Asahi Kasei Corporation):Compound (III-5)-1 = 0.1:0.9 | Compound (IV-2)<br>Number average molecular weight: 1800<br>Ratio of n421 to n422 (n421/n422):1 | good |
| Example 4-21 | Molar ratio<br>pentamethylene diisocyanate:HDI = 1:1 | Compound (IV-2)<br>Number average molecular weight: 1800<br>Ratio of n421 to n422 (n421/n422):1 | good |
| Example 4-22 | Mass ratio<br>DURANATE TPA-100 (manufactured by Asahi Kasei Corporation):HDI = 0.1:0.9 | Compound (IV-2)<br>Number average molecular weight: 500<br>Ratio of n421 to n422 (n421/n422):1<br>(random copolymer) | good |
| Example 4-23 | Mass ratio<br>DURANATE TPA-100 (manufactured by Asahi Kasei Corporation):pentamethylene diisocyanate = 0.1:0.9 | Compound (IV-2)<br>Number average molecular weight: 1800<br>Ratio of n421 to n422 (n421/n422):1 | good |

TABLE 10-continued

| | Diisocyanate | Hydrophilic group-containing compound | Storage stability of resin composition |
|---|---|---|---|
| Example 4-24 | Molar ratio Compound (III-6)-1:Compound (VI-2)-1 = 1:1 | Compound (IV-2) Number average molecular weight: 300 Ratio of n421 to n422 (n421/n422):1 | good |
| Comparative Example 4-1 | 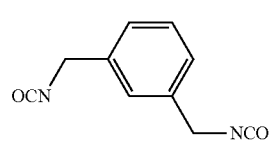<br>Compound (VI-3)-1 | MPEG400 | poor |

Based on Tables 9 and 10, it was evident that whereas the compounds produced in Examples 4-1 to 4-24 all exhibited good storage stability when used as resin compositions, the compound produced in Comparative Example 4-1 exhibited poor storage stability when used as a resin composition.

Examples 5-1 to 5-71

<Evaluation Method>
[Evaluation 5-1] Storage Stability of Resin Composition

Evaluations of the compounds obtained in the examples were conducted using the method described below.

Specifically, 1 g of each of the compounds obtained in the examples was first dispersed in 10 g of butyl acetate, and 15 g of an acrylic polyol (STALAX 1152 manufactured by Allnex Group) was added and stirred to form a uniform solution (resin composition). This uniform solution (resin composition) was stored at 40° C. for 10 days, and the contents were then inspected visually. The storage stability was evaluated against the following evaluation criteria.

(Evaluation Criteria)
Good: the viscosity after storage at 40° C. for 10 days was less than 1.5 times the viscosity immediately after production
Poor: the viscosity after storage at 40° C. for 10 days was at least 1.5 times the viscosity immediately after production <Production of Carbodiimide Group-Containing Compound>

Example 5-1

An SUS316 stirred tank with an internal capacity of 2 L and fitted with a reflux condenser was charged with 600 g of xylene, 500 g of hexamethylene diisocyanate and 118 g of tert-butyl isocyanate, and the mixture was heated to 140° C. Subsequently, 1 g of 1-phenyl-2-phospholene-1-oxide was added to the tank and stirred for 30 hours. The obtained reaction liquid was supplied to a thin-film evaporator, the interior of which had been heated to 180° C. and evacuated to a pressure of 0.1 kPa (absolute pressure), thereby removing the xylene by evaporation to obtain a compound. Analysis of the obtained compound by infrared spectroscopy confirmed an absorption peak attributable to a carbodiimide group.

Evaluation of the resin composition storage stability for the obtained compound using the evaluation method described above yielded a good result.

Examples 5-2 to 5-71

With the exceptions of using the combinations of diisocyanates and hydrophilic group-containing compounds shown below in Tables 11 to 18, the same method as that described for Example 5-1 was used to produce compounds, and then evaluate the storage stability when used as resin compositions.

TABLE 11

| | Diisocyanate | Hydrophilic group-containing compound | Storage stability of resin composition |
|---|---|---|---|
| Example 5-1 | OCN—(CH₂)₆—NCO<br>Hexamethylene diisocyanate (HDI) | tert-butyl isocyanate | good |
| Example 5-2 | OCN—(CH₂)₆—NCO<br>Hexamethylene diisocyanate (HDI) | Cyclohexyl isocyanate | good |

TABLE 11-continued

| | Diisocyanate | Hydrophilic group-containing compound | Storage stability of resin composition |
|---|---|---|---|
| Example 5-3 | OCN─(CH$_2$)$_6$─NCO<br>Hexamethylene diisocyanate (HDI) | 1-hexyl isocyanate | good |
| Example 5-4 | OCN─(CH$_2$)$_6$─NCO<br>Hexamethylene diisocyanate (HDI) | α,α-dimethylbenzyl isocyanate | good |
| Example 5-5 | OCN─(CH$_2$)$_6$─NCO<br>Hexamethylene diisocyanate (HDI) | (S)-1-phenylethyl isocyanate | good |
| Example 5-6 | OCN─(CH$_2$)$_6$─NCO<br>Hexamethylene diisocyanate (HDI) | Benzyl isocyanate | good |
| Example 5-7 | OCN─(CH$_2$)$_6$─NCO<br>Hexamethylene diisocyanate (HDI) | Phenyl isocyanate | good |
| Example 5-8 | OCN─(CH$_2$)$_6$─NCO<br>Hexamethylene diisocyanate (HDI) | Methyl (S)-(−)-2-isocyanatopropionate | good |
| Example 5-9 | OCN─(CH$_2$)$_6$─NCO<br>Hexamethylene diisocyanate (HDI) | | good |

TABLE 12

| | Diisocyanate | Hydrophilic group-containing compound | Storage stability of resin composition |
|---|---|---|---|
| Example 5-10 | OCN─(CH$_2$)$_4$─NCO<br>Tetramethylene diisocyanate | 1-hexyl isocyanate | good |

TABLE 12-continued

| | Diisocyanate | Hydrophilic group-containing compound | Storage stability of resin composition |
|---|---|---|---|
| Example 5-11 | Isophorone diisocyanate (IPDI) | 1-hexyl isocyanate | good |
| Example 5-12 | Hydrogenated MDI | 1-hexyl isocyanate | good |
| Example 5-13 | XDI | 1-hexyl isocyanate | good |
| Example 5-14 | TMXDI | 1-hexyl isocyanate | good |
| Example 5-15 | MDI | 1-hexyl isocyanate | good |
| Example 5-16 | Molar ratio Pentamethylene diisocyanate: HDI = 1:1 | 1-hexyl isocyanate | good |
| Example 5-17 | Molar ratio Hydrogenated XDI: Hydrogenated MDI = 1:1 | 1-hexyl isocyanate | good |
| Example 5-18 | Molar ratio XDI:HDI = 1:1 | 1-hexyl isocyanate | good |
| Example 5-19 | Molar ratio Hydrogenated XDI:XDI = 1:1 | 1-hexyl isocyanate | good |

TABLE 13

| | Diisocyanate | Hydrophilic group-containing compound | Storage stability of resin composition |
|---|---|---|---|
| Example 5-20 | Molar ratio Hydrogenated XDI :TMXDI = 1:1 | 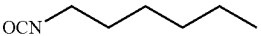 1-hexyl isocyanate | good |
| Example 5-21 | Molar ratio MDI:XDI = 1:1 |  1-hexyl isocyanate | good |
| Example 5-22 | Molar ratio Hydrogenated XDI:MDI = 1:1 | 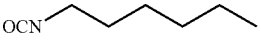 1-hexyl isocyanate | good |
| Example 5-23 | Molar ratio TMXDI:MDI = 1:1 |  1-hexyl isocyanate | good |
| Example 5-24 | Molar ratio IPDI:HDI = 1:1 |  1-hexyl isocyanate | good |
| Example 5-25 | Mass ratio DURANATE TPA-100 (manufactured by Asahi Kasei Corporation):HDI = 0.1:0.9 |  1-hexyl isocyanate | good |
| Example 5-26 | Mass ratio DURANATE TPA-100 (manufactured by Asahi Kasei Corporation): pentamethylene diisocyanate = 0.1:0.9 |  1-hexyl isocyanate | good |
| Example 5-27 | Mass ratio DURANATE TPA-100 (manufactured by Asahi Kasei Corporation): Hydrogenated MDI = 0.1:0.9 |  1-hexyl isocyanate | good |

TABLE 14

| | Diisocyanate | Hydrophilic group-containing compound | Storage stability of resin composition |
|---|---|---|---|
| Example 5-28 |  Hexamethylene diisocyanate (HDI) |  tert-butylamine | good |
| Example 5-29 |  Hexamethylene diisocyanate (HDI) |  Cyclohexylamine | good |
| Example 5-30 | 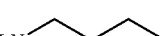 Hexamethylene diisocyanate (HDI) | 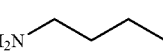 N-hexylamine | good |

TABLE 14-continued

| | Diisocyanate | Hydrophilic group-containing compound | Storage stability of resin composition |
|---|---|---|---|
| Example 5-31 | OCN—(CH₂)₆—NCO<br><br>Hexamethylene diisocyanate (HDI) | 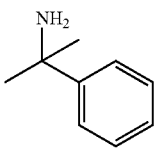<br>α,α-dimethylbenzylamine | good |
| Example 5-32 | OCN—(CH₂)₆—NCO<br><br>Hexamethylene diisocyanate (HDI) | 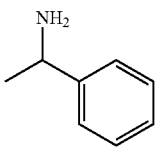<br>(S)-1-phenylethylamine | good |
| Example 5-33 | OCN—(CH₂)₆—NCO<br><br>Hexamethylene diisocyanate (HDI) | 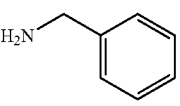<br>Benzylamine | good |
| Example 5-34 | OCN—(CH₂)₆—NCO<br><br>Hexamethylene diisocyanate (HDI) | 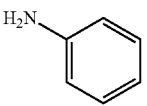<br>Phenylamine | good |
| Example 5-35 | OCN—(CH₂)₆—NCO<br><br>Hexamethylene diisocyanate (HDI) | 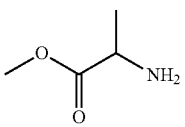<br>Alanine methyl ester | good |
| Example 5-36 | OCN—(CH₂)₆—NCO<br><br>Hexamethylene diisocyanate (HDI) | <br>Glycine methyl ester | good |

TABLE 15

| | Diisocyanate | Hydrophilic group-containing compound | Storage stability of resin composition |
|---|---|---|---|
| Example 5-37 | OCN—(CH₂)₄—NCO<br><br>Tetramethylene diisocyanate | 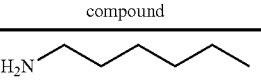<br>N-hexylamine | good |
| Example 5-38 | 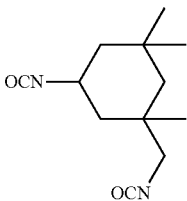<br>IPDI | 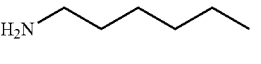<br>N-hexylamine | good |

TABLE 15-continued

| | Diisocyanate | Hydrophilic group-containing compound | Storage stability of resin composition |
|---|---|---|---|
| Example 5-39 | Hydrogenated MDI | N-hexylamine | good |
| Example 5-40 | XDI | N-hexylamine | good |
| Example 5-41 | TMXDI | N-hexylamine | good |
| Example 5-42 | MDI | N-hexylamine | good |
| Example 5-43 | Molar ratio Pentamethylene diisocyanate: HDI = 1:1 | N-hexylamine | good |
| Example 5-44 | Molar ratio Hydrogenated XDI: Hydrogenated MDI = 1:1 | N-hexylamine | good |
| Example 5-45 | Molar ratio XDI:HDI = 1:1 | N-hexylamine | good |
| Example 5-46 | Molar ratio Hydrogenated XDI:XDI = 1:1 | N-hexylamine | good |

TABLE 16

| | Diisocyanate | Hydrophilic group-containing compound | Storage stability of resin composition |
|---|---|---|---|
| Example 5-47 | Molar ratio Hydrogenated XDI:TMXDI = 1:1 | N-hexylamine | good |
| Example 5-48 | Molar ratio MDI:XDI = 1:1 | N-hexylamine | good |

TABLE 16-continued

| | Diisocyanate | Hydrophilic group-containing compound | Storage stability of resin composition |
|---|---|---|---|
| Example 5-49 | Molar ratio Hydrogenated XDI:MDI = 1:1 | H₂N~~~ N-hexylamine | good |
| Example 5-50 | Molar ratio TMXDI:MDI = 1:1 | H₂N~~~ N-hexylamine | good |
| Example 5-51 | Molar ratio IPDI:HDI = 1:1 | H₂N~~~ N-hexylamine | good |
| Example 5-52 | Mass ratio DURANATE TPA-100 (manufactured by Asahi Kasei Corporation):HDI = 0.1:0.9 | H₂N~~~ N-hexylamine | good |
| Example 5-53 | Mass ratio DURANATE TPA-100 (manufactured by Asahi Kasei Corporation): pentamethylene diisocyanate = 0.1:0.9 | H₂N~~~ N-hexylamine | good |
| Example 5-54 | Mass ratio DURANATE TPA-100 (manufactured by Asahi Kasei Corporation): Hydrogenated MDI = 0.1:0.9 | H₂N~~~ N-hexylamine | good |

TABLE 17

| | Diisocyanate | Hydrophilic group-containing compound | Storage stability of resin composition |
|---|---|---|---|
| Example 5-55 | OCN—(CH₂)₆—NCO Hexamethylene diisocyanate (HDI) | tert-butyl alcohol | good |
| Example 5-56 | OCN—(CH₂)₆—NCO Hexamethylene diisocyanate (HDI) | Cyclohexanol | good |
| Example 5-57 | OCN—(CH₂)₆—NCO Hexamethylene diisocyanate (HDI) | 1-hexanol | good |
| Example 5-58 | OCN—(CH₂)₆—NCO Hexamethylene diisocyanate (HDI) | 2-phenyl-2-propanol | good |

TABLE 17-continued

| | Diisocyanate | Hydrophilic group-containing compound | Storage stability of resin composition |
|---|---|---|---|
| Example 5-59 | OCN—(CH$_2$)$_6$—NCO<br>Hexamethylene diisocyanate (HDI) | 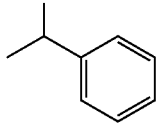<br>1-phenylethanol | good |
| Example 5-60 | OCN—(CH$_2$)$_6$—NCO<br>Hexamethylene diisocyanate (HDI) | 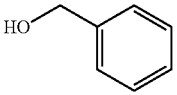<br>Benzyl alcohol | good |
| Example 5-61 | OCN—(CH$_2$)$_6$—NCO<br>Hexamethylene diisocyanate (HDI) | 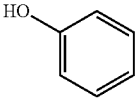<br>Phenol | good |

TABLE 18

| | Diisocyanate | Hydrophilic group-containing compound | Storage stability of resin composition |
|---|---|---|---|
| Example 5-62 | OCN—(CH$_2$)$_4$—NCO<br>Tetramethylene diisocyanate | 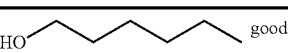<br>1-hexanol | good |
| Example 5-63 | 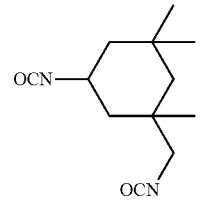<br>IPDI | 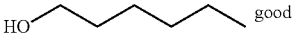<br>1-hexanol | good |
| Example 5-64 | <br>Hydrogenated MDI | 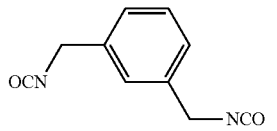<br>1-hexanol | good |
| Example 5-65 | 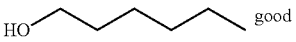<br>XDI | 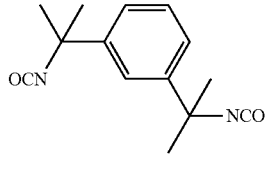<br>1-hexanol | good |
| Example 5-66 | 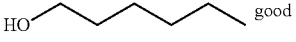<br>TMXDI | HO~~~~~<br>1-hexanol | good |

TABLE 18-continued

| | Diisocyanate | Hydrophilic group-containing compound | Storage stability of resin composition |
|---|---|---|---|
| Example 5-67 | OCN—⌬—CH₂—⌬—NCO<br>MDI | HO~~~~~~ <br>1-hexanol | good |
| Example 5-68 | Molar ratio<br>Pentamethylene diisocyanate:<br>HDI = 1:1 | HO~~~~~~ <br>1-hexanol | good |
| Example 5-69 | Molar ratio<br>Hydrogenated XDI:<br>Hydrogenated MDI = 1:1 | HO~~~~~~ <br>1-hexanol | good |
| Example 5-70 | Molar ratio<br>XDI:HDI = 1:1 | HO~~~~~~ <br>1-hexanol | good |
| Example 5-71 | Molar ratio<br>Hydrogenated XDI:XDI = 1:1 | HO~~~~~~ <br>1-hexanol | good |

Based on Tables 11 to 18, it was evident that the compounds produced in Examples 5-1 to 5-71 all exhibited good storage stability when used as resin compositions.

Examples 6-1 to 6-21, Comparative Examples 6-1 and 6-2

<Evaluation Methods>
[Evaluation 6-1] Storage Stability Evaluation (Resin Composition Evaluation 1)

Using the method described below, the storage stability was evaluated by measuring the gelling time of the resin compositions that used the compounds obtained in the examples and comparative examples.

Specifically, 2 g of each of the compounds obtained in the examples and comparative examples was first dispersed in 5 g of water, and the resulting dispersion was added to 20 g of a polyurethane water dispersion (SUPERFLEX 150, manufactured by DKS Co., Ltd.) to form a uniform solution (resin composition). This uniform solution (resin composition) was heated to 40° C., the contents were inspected visually every 5 hours to confirm the presence or absence of gelling, and the time elapsed until gelling was confirmed was recorded as the gelling time. Subsequently, using the obtained gelling time, the storage stability was evaluated against the following evaluation criteria.
(Evaluation Criteria)
 Good: gelling time of 10 hours or longer
 Poor: gelling time of less than 10 hours
[Evaluation 6-2] Evaluation of Reactivity with Main Agent (Resin Composition Evaluation 2)

Evaluations of the reactivity with the main agent were conducted by measuring the increase in the gel fraction of the resin composition formed using each of the compounds obtained in the examples and comparative examples using the method described below.

Specifically, 5 g of water was first added to 20 g of a polyurethane water dispersion (SUPERFLEX 150, manufactured by DKS Co., Ltd.) and stirred to obtain a uniform solution. This uniform solution was coated onto a polypropylene sheet (hereafter sometimes abbreviated as "PP sheet") and cured inside a dryer at 100° C. Subsequently, the coating film was cut from the PP sheet, placed in a woven wire mesh and immersed in an acetone solution for 16 hours, and the coating film and the woven wire mesh were then removed from the acetone and dried using a dryer. The change in the mass of the coating film from before immersion to after immersion in the acetone solution was measured, and the value obtained by dividing the change in the mass of the coating film by the mass of the coating film before immersion was calculated as the reference gel fraction.

Subsequently, 2 g of each of the compounds obtained in the examples and comparative examples was dispersed in 5 g of water, and the resulting dispersion was added to 20 g of a polyurethane water dispersion (SUPERFLEX 150, manufactured by DKS Co., Ltd.) and stirred to form a uniform solution (resin composition). This uniform solution (resin composition) was coated onto a PP sheet and cured in the same manner as described above, the gel fraction was then measured in the same manner as described above, and the increase in the gel fraction was determined from the difference relative to the reference gel fraction. Based on the thus obtained increase in the gel fraction, the reactivity with the main agent was evaluated against the following evaluation criteria.
(Evaluation Criteria)
 Good: increase in gel fraction of at least 10%
 Poor: increase in gel fraction of less than 10%
[Evaluation 6-3] Water Resistance of Coating Film (Coating Film Evaluation 1)

Evaluations of the water resistance of the coating films formed using the compounds obtained in the examples and comparative examples were conducted using the method described below. Specifically, 5 g of water was first added to 20 g of a polyurethane water dispersion (SUPERFLEX 150, manufactured by DKS Co., Ltd.) and stirred to obtain a uniform solution. This uniform solution (resin composition) was coated onto a PP sheet and cured in a dryer at 100° C. Subsequently, an O-ring (inner diameter: 1.78 mm, wire diameter: 1.78 mm) was placed on top of the coating film, and 1 mL of ion-exchanged water was dripped inside the O-ring. Subsequently, the coating film was left to stand for 5 hours at room temperature, and the degree of whitening of the coating film was then confirmed visually as a reference.

Subsequently, 2 g of each of the compounds obtained in the examples and comparative examples was dispersed in 5 g of water, and the resulting dispersion was added to 20 g of a polyurethane water dispersion (SUPERFLEX 150, manufactured by DKS Co., Ltd.) and stirred to form a uniform solution (resin composition). This uniform solution (resin composition) was coated onto a PP sheet and cured in the same manner as described above, and the degree of whitening of the coating film was confirmed visually using the same method as described above and compared with the reference. Based on the obtained visual results, the water resistance of the coating film was evaluated against the following evaluation criteria.
(Evaluation Criteria)
Good: the degree of whitening was less than the reference, indicating superior water resistance
Poor: the degree of whitening was at least as great as the reference, indicating low water resistance Comparative Example 6-1

(Step 1)
Hexamethylene diisocyanate was used as the diisocyanate (hereafter sometimes referred to as "diisocyanate A") for producing a carbodiimide compound. An SUS316 stirred tank with an internal capacity of 1 L was charged with 300 g of xylene and 500 g of the diisocyanate A, and the mixture was heated to 140° C. Subsequently, 1 g of 1-phenyl-2-phospholene-1-oxide was added to the tank and stirred for 5 hours. The xylene and excess isocyanate compound were removed from the reaction liquid by evaporation using a thin-film evaporator, thus obtaining a compound. Analysis of the obtained compound by infrared spectroscopy confirmed absorption peaks attributable to an uretonimine group and a carbodiimide group.
(Step 2)
Subsequently, 890 g of a poly(oxyethylene-oxypropylene) glycol monobutyl ether (number average molecular weight: 970, a compound represented by formula (IV-2) shown below (hereafter sometimes referred to as "compound (IV-2)") was added as a compound having a hydrophilic group (hereafter sometimes referred to as the "hydrophilic group-containing compound") to the compound obtained above in step 1, and the mixture was heated under stirring at 150° C. for 8 hours. When the obtained compound was analyzed by $^{13}$C-NMR spectroscopy, no peak was observed at a chemical shift corresponding with an uretonimine group.

[Chemical formula 95]

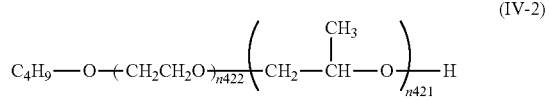

(IV-2)

(In general formula (IV-2), the ratio of n421 relative to n422 is 1.)
(Step 3)
Using phenyl isocyanate as the isocyanate compound (hereafter sometimes referred to as "isocyanate compound B") reacted with the carbodiimide group, the compound obtained above in step 2 and phenyl isocyanate were mixed such that the stoichiometric ratio of the isocyanate group of the isocyanate compound B relative to the carbodiimide group of the carbodiimide compound was 1.05-fold, and the mixture was then heated at 80° C. for 5 hours. The obtained compound was a compound which, in an infrared spectroscopy spectrum, exhibited a value for the absorbance x near 2020 cm$^{-1}$ attributable to the stretching vibration of carbodiimide groups relative to the absorbance y near 1720 cm$^{-1}$ attributable to the stretching vibration of uretonimine groups and urethane groups, namely a value represented by x/y, of 0.3.

Comparative Example 6-2, Examples 6-1 to 6-20

With the exceptions of using the combinations of the diisocyanate A, the isocyanate compound B and the hydrophilic group-containing compound shown below in Tables 19 and 20, the same method as that described for Comparative Example 6-1 was used to produce compounds, and then evaluate the storage stability when used as a resin composition, the reactivity with the main agent, and the water resistance when used to form a coating film. In Tables 19 and 20, the compound X among the isocyanate compounds B is shown below. Further, the abbreviations used for the hydrophilic group-containing compounds represent the compounds described below. Furthermore, for the compound (IV-2), compounds having different number average molecular weights of 300, 510, 970 and 1800 (compounds having different degrees of polymerization) were used as appropriate.
(Isocyanate Compound B)
The compound X is a compound represented by formula (X) shown below, and represents a compound obtained by conventional methods in which one terminal isocyanate group of hexamethylene diisocyanate has been modified with a monofunctional polyalkylene oxide poly ether alcohol.

[Chemical formula 96]

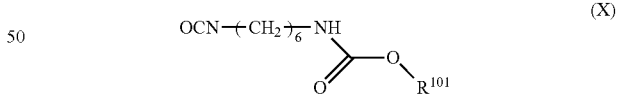

(X)

(In formula (X), R$^{101}$ is a group represented by formula (X-1) shown below.)

[Chemical formula 97]

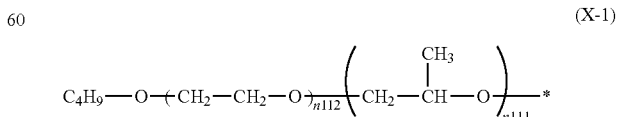

(X-1)

(In general formula (X-1), the ratio of n111 relative to n112 is 1.)

(Hydrophilic Group-Containing Compounds)

MPEG220: polyethylene glycol monomethyl ether (number average molecular weight: 220)

MPEG550: polyethylene glycol monomethyl ether (number average molecular weight: 550)

TABLE 19

| | Diisocyanate A | Isocyanate compound B | Hydrophilic group-containing compound | x/y | Storage stability of resin composition | Reactivity with main agent | Curability of coating film |
|---|---|---|---|---|---|---|---|
| Example 6-1 | OCN—(CH$_2$)$_6$—NCO<br>Hexamethylene diisocyanate (HDI) | OCN-CH$_2$-C(=O)-O-CH$_2$CH$_3$ | Compound (IV-2)<br>Number average molecular weight: 300<br>Ratio of n421 to n422 (n421/n422):1 | 0.0 | good | good | good |
| Example 6-2 | OCN—(CH$_2$)$_6$—NCO<br>Hexamethylene diisocyanate (HDI) | OCN-CH$_2$-C(=O)-O-CH$_2$CH$_3$ | Compound (IV-2)<br>Number average molecular weight: 970<br>Ratio of n421 to n422 (n421/n422):1 | 0.0 | good | good | good |
| Example 6-3 | OCN—(CH$_2$)$_6$—NCO<br>Hexamethylene diisocyanate (HDI) | OCN-CH$_2$-C(=O)-O-CH$_2$CH$_3$ | Compound (IV-2)<br>Number average molecular weight: 1800<br>Ratio of n421 to n422 (n421/n422):1 | 0.0 | good | good | good |
| Example 6-4 | OCN—(CH$_2$)$_6$—NCO<br>Hexamethylene diisocyanate (HDI) | OCN-CH$_2$-C(=O)-O-CH$_2$CH$_3$ | MPEG550 | 0.0 | good | good | good |
| Example 6-5 | OCN—(CH$_2$)$_6$—NCO<br>Hexamethylene diisocyanate (HDI) | OCN-CH$_2$-C(=O)-O-CH$_2$CH$_3$ | MPEG220 | 0.0 | good | good | good |
| Example 6-6 | OCN—(CH$_2$)$_6$—NCO<br>Hexamethylene diisocyanate (HDI) | OCN-CH$_2$-C(=O)-O-CH$_2$CH$_3$ | Triethylene glycol monomethyl ether | 0.0 | good | good | good |
| Example 6-7 | OCN—(CH$_2$)$_6$—NCO<br>Hexamethylene diisocyanate (HDI) | OCN-CH$_2$-C(=O)-O-CH$_2$CH$_3$ | Diethylene glycol monomethyl ether | 0.0 | good | good | good |
| Example 6-8 | OCN—(CH$_2$)$_4$—NCO<br>Tetramethylene diisocyanate | OCN-CH$_2$-C(=O)-O-CH$_2$CH$_3$ | Compound (IV-2)<br>Number average molecular weight: 300<br>Ratio of n421 to n422 (n421/n422):1 | 0.0 | good | good | good |
| Example 6-9 | OCN—⌬—CH$_2$—⌬—NCO<br>Compound (III-5)-1 | OCN-CH$_2$-C(=O)-O-CH$_2$CH$_3$ | Compound (IV-2)<br>Number average molecular weight: 970<br>Ratio of n421 to n422 (n421/n422):1 | 0.0 | good | good | good |
| Example 6-10 | (cyclohexane with OCN-CH$_2$ and CH$_2$-NCO)<br>Compound (VI-2)-1 | OCN-CH$_2$-C(=O)-O-CH$_2$CH$_3$ | Compound (IV-2)<br>Number average molecular weight: 510<br>Ratio of n421 to n422 (n421/n422):1 | 0.1 | good | good | good |

TABLE 20

| | Diisocyanate A | Isocyanate compound B | Hydrophilic group-containing compound | x/y | Storage stability of resin composition | Reactivity with main agent | Curability of coating film |
|---|---|---|---|---|---|---|---|
| Example 6-11 | OCN—(CH₂)₆—NCO<br>HDI | Methyl 2-isocyanato-4-methylpentanoate | Compound (IV-2)<br>Number average molecular weight: 1800<br>Ratio of n421 to n422 (n421/n422):1 | 0.0 | good | good | good |
| Example 6-12 | OCN—(CH₂)₆—NCO<br>HDI | Ethyl 2-isocyanato-3-methylpentanoate | Compound (IV-2)<br>Number average molecular weight: 510<br>Ratio of n421 to n422 (n421/n422):1 | 0.1 | good | good | good |
| Example 6-13 | OCN—(CH₂)₆—NCO<br>HDI | Diethyl/dipropyl 2-isocyanatoglutarate | MPEG550 | 0.2 | good | good | good |
| Example 6-14 | OCN—(CH₂)₆—NCO<br>HDI | Cyclohexyl isocyanate | Compound (IV-2)<br>Number average molecular weight: 970<br>Ratio of n421 to n422 (n421/n422):1 | 0.0 | good | good | good |
| Example 6-15 | OCN—(CH₂)₆—NCO<br>HDI | Isophorone diisocyanate-type structure with two OCN groups | Compound (IV-2)<br>Number average molecular weight: 970<br>Ratio of n421 to n422 (n421/n422):1 | 0.2 | good | good | good |
| Example 6-16 | Isophorone diisocyanate (IPDI) | Ethyl isocyanatoacetate | Compound (IV-2)<br>Number average molecular weight: 510<br>Ratio of n421 to n422 (n421/n422):1 | 0.1 | good | good | good |
| Example 6-17 | Molar ratio<br>Pentamethylene diisocyanate: HDI = 1:1 | Cyclohexyl isocyanate | Compound (IV-2)<br>Number average molecular weight: 970<br>Ratio of n421 to n422 (n421/n422):1 | 0.2 | good | good | good |

TABLE 20-continued

| | Diisocyanate A | Isocyanate compound B | Hydrophilic group-containing compound | x/y | Storage stability of resin composition | Reactivity with main agent | Curability of coating film |
|---|---|---|---|---|---|---|---|
| Example 6-18 | OCN—⬡—CH₂—⬡—NCO<br>Hydrogenated MDI | OCN—CH₂CH₂CH₂CH₃<br>1-butyl isocyanate | Compound (IV-2)<br>Number average molecular weight: 970<br>Ratio of n421 to n422 (n421/n422):1 | 0.0 | good | good | good |
| Example 6-19 | Hydrogenated XDI | OCN—CH₂—C(=O)—O—CH₂CH₃ | Compound (IV-2)<br>Number average molecular weight: 510<br>Ratio of n421 to n422 (n421/n422):1 | 0.1 | good | good | good |
| Example 6-20 | Molar ratio<br>Hydrogenated MDI:<br>Hydrogenated XDI = 1:1 | OCN—CH₂—C(=O)—O—CH₂CH₃ | Compound (IV-2)<br>Number average molecular weight: 1800<br>Ratio of n421 to n422 (n421/n422):1 | 0.1 | good | good | good |
| Comparative Example 6-1 | OCN—(CH₂)₆—NCO<br>HDI | OCN—C₆H₅<br>Phenyl isocyanate | Compound (IV-2)<br>Number average molecular weight: 970<br>Ratio of n421 to n422 (n421/n422):1 | 0.3 | poor | good | good |
| Comparative Example 6-2 | OCN—(CH₂)₆—NCO<br>HDI | Compound (X) | Compound (IV-2)<br>Number average molecular weight: 970<br>Ratio of n421 to n422 (n421/n422):1 | 0.0 | good | poor | poor |

Based on Tables 19 and 20, it was evident that the compounds produced in Examples 6-1 to 6-20 all exhibited good results for the storage stability when used as a resin composition, the reactivity with the main agent, and the water resistance when used to form a coating film. In contrast, although the compound produced in Comparative Example 6-1 exhibited good results for the reactivity with the main agent and the water resistance when used to form a coating film, the storage stability when used as a resin composition was poor. Further, although the compound produced in Comparative Example 6-2 exhibited good storage stability when used as a resin composition, the reactivity with the main agent and the water resistance when used to form a coating film were poor.

INDUSTRIAL APPLICABILITY

The compound of an embodiment of the present invention is able to provide a novel compound having an uretonimine group. Further, the compound of an embodiment of the present invention is able to provide a novel carbodiimide compound. The compounds of embodiments of the present invention exhibit excellent water dispersibility, and can be used favorably as curing agent components for water-based resin compositions.

The invention claimed is:

1. A compound having an uretonimine group, the compound of general formula (1α):

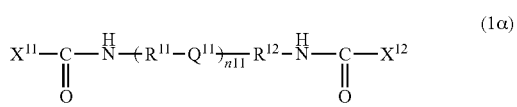

wherein in general formula (1α), n11 is an integer of at least 1 but not more than 100, each of $X^{11}$ and $X^{12}$ is independently a residue obtained by removing a hydrogen atom from a terminal hydroxyl group of a mono-functional polyalkylene oxide polyether alcohol, $Q^{11}$ is a group of general formula (1-a) shown below or a group of general formula (1-b) shown below, when n11 is 1, $Q^{11}$ is a group of general formula (1-b) shown below, and when n11 is 2 or greater, plural $Q^{11}$ may be identical to or different from each other, and each of $R^{11}$ and $R^{12}$ is independently a residue obtained by removing two isocyanate groups from a diisocyanate, $$*-N=C=N-* \quad (1\text{-a})$$

(1-b)

wherein in the formulas, each asterisk indicates a bonding site, in general formula (1-b), $Y^{11}$ is a residue obtained by removing one isocyanate group from an isocyanate compound, and the diisocyanate and the isocyanate compound are different compounds.

2. The compound according to claim 1, wherein in a spectrum measured by infrared spectroscopy, a ratio of an absorbance attributable to carbodiimide groups relative to an absorbance attributable to uretonimine groups and urethane groups is at least 0 but less than 1.5.

3. The compound according to claim 1, wherein the monofunctional polyalkylene oxide polyether alcohol is a polyethylene glycol monoalkyl ether, a polypropylene glycol monoalkyl ether, or a copolymer thereof.

4. The compound according to claim 1, wherein each of $X^{11}$ and $X^{12}$ is independently a group of general formula (II-1) shown below or a group of general formula (II-2) shown below:

(II-1)

(II-2)

wherein in general formula (II-1),
each of n21 and n22 is independently an integer of at least 1 but not more than 30, and
$R^{21}$ is an alkyl group of at least 1 but not more than 12 carbon atoms that may contain a carbonyl group,
in general formula (II-2),
each of n23 and n24 is independently an integer of at least 1 but not more than 30, and
$R^{22}$ is an alkyl group of at least 1 but not more than 12 carbon atoms that may contain a carbonyl group, and
each asterisk indicates a bonding site.

5. The compound according to claim 1, wherein
each of $R^{11}$ and $R^{12}$ is independently a group of general formula (III-1), a group of general formula (III-2), a group of general formula (III-3), a group of general formula (III-5), a group of general formula (III-6), or a group of general formula (VI):

(III-1)

(III-2)

(III-3)

(III-5)

(III-6)

$$*-CH_2-R^{61}-CH_2-* \quad (VI)$$

wherein each asterisk indicates a bonding site, $R^{61}$ is an alkylene group of at least 1 but not more than 18 carbon atoms, or an arylene group of at least 6 but not more than 18 carbon atoms, and the alkylene group and the arylene group may each have at least one functional group selected from the group consisting of an isocyanurate group, an allophanate group, a biuret group, an uretdione group, an iminooxadiazinedione group and a urethane group.

6. The compound according to claim 5, wherein $R^{11}$ and $R^{12}$ are groups of the general formula (VI).

7. The compound according to claim 6, wherein each of $R^{11}$ and $R^{12}$ is independently at least one group selected from the group consisting of groups of general formula (VI-1) shown below, a group of general formula (VI-2) shown below and a group of general formula (VI-3) shown below:

(VI-1)

(VI-2)

(VI-3)

wherein in the formulas, each asterisk indicates a bonding site, and in general formula (VI-1), n61 is an integer of at least 1 but not more than 10.

8. The compound according to claim 7, wherein each of $R^{11}$ and $R^{12}$ is independently a group of the general formula (VI-1), and the isocyanate compound is an aliphatic isocyanate compound.

9. The compound according to claim 8, wherein among a carbon atom that is bonded to the uretonimine group in $Y^{11}$, and a carbon atom that is bonded to the uretonimine group in $R^{11}$ or $R^{12}$,
one carbon atom is a primary carbon atom or a primary carbon atom to which an electron-withdrawing group is bonded, and another carbon atom is a secondary carbon atom, or
one carbon atom is a primary carbon atom to which an electron-withdrawing group is bonded, and another carbon atom is a primary carbon atom to which an electron-withdrawing group is not bonded.

10. The compound according to claim 1, wherein the isocyanate compound is at least one of an isocyanate derived from an amino acid and a trifunctional or higher isocyanate.

11. The compound according to claim 10, wherein the trifunctional or higher isocyanate is a trifunctional isocyanate.

12. The compound according to claim 11, wherein the trifunctional isocyanate is a compound of general formula (1-B)-3c shown below:

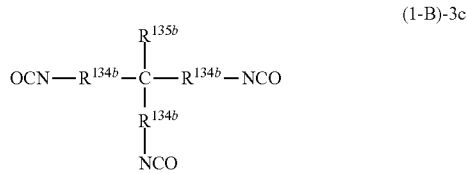

(1-B)-3c wherein in general formula (1-B)-3c, each of a plurality of $R^{134b}$ groups is independently a single bond, or a divalent hydrocarbon group of at least 1 but not more than 20 carbon atoms that may contain at least one group selected from the group consisting of an ester group and an ether group, and $R^{135b}$ is a hydrogen atom or a monovalent hydrocarbon group of at least 1 but not more than 12 carbon atoms.

13. The compound according to claim 10, wherein the isocyanate having a group derived from an amino acid is an isocyanate having a group of formula (5) shown below:

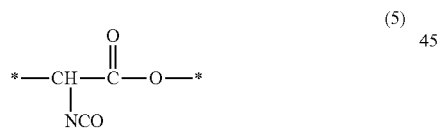

(5)

wherein in formula (5), each asterisk indicates a bonding site.

14. A method for producing a compound of claim 1, the method comprising:
producing a compound having an uretonimine group of general formula (1α) by reacting a carbodiimide compound of general formula (2β) shown below and an isocyanate compound of general formula (3) shown below:

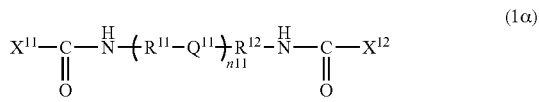

(1α)

wherein in general formula (1α), n11 is an integer of at least 1 but not more than 100, each of $X^{11}$ and $X^{12}$ is independently a residue obtained by removing a hydrogen atom from a terminal hydroxyl group of a monofunctional polyalkylene oxide polyether alcohol, $Q^{11}$ is a group of formula (1-b) shown below, when n11 is 1, $Q^{11}$ is a general formula (1-b) shown below, and when n11 is 2 or greater, plural $Q^{11}$ may be identical to or different from each other, and each of $R^{11}$ and $R^{12}$ is independently a residue obtained by removing two isocyanate groups from a diisocyanate,

(1-a)

(1-b)

wherein in the formulas, each asterisk indicates a bonding site, in general formula (1-b), $Y^{11}$ is a residue obtained by removing one isocyanate group from an isocyanate compound, and the diisocyanate and the isocyanate compound are different compounds,

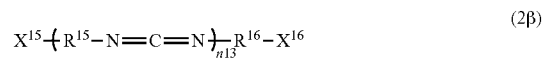

(2β)

wherein in general formula (2β), n13 is an integer of at least 1 but not more than 100, each of $X^{15}$ and $X^{16}$ is independently a group of general formula (VIII) shown below, each of $R^{15}$ and $R^{16}$ is independently a residue obtained by removing two isocyanate groups from a diisocyanate or a polyisocyanate derived from a diisocyanate,

(VIII)

wherein in general formula (VIII), $Y^{81}$ is a carbodiimide group, a urea group or a urethane group, $R^{81}$ is a monovalent hydrocarbon group of at least 1 but not more than 12 carbon atoms that may include a carbonyl group or an ester linkage, and an asterisk indicates a bonding site,

(3)

wherein in general formula (3), $R^3$ is a residue obtained by removing one isocyanate group from an isocyanate compound.

15. A curing agent composition, comprising a compound of claim 1.

16. A resin composition, comprising a curing agent composition of claim 15 and a compound having a carboxyl group.

17. A coating material composition, comprising a resin composition of claim 16.

18. A resin cured product, obtained by curing a coating material composition of claim 17.

* * * * *